United States Patent
Leydon

(10) Patent No.: US 10,869,638 B2
(45) Date of Patent: Dec. 22, 2020

(54) SYSTEMS, DEVICES AND METHODS FOR RENDERING KEY RESPIRATORY MEASUREMENTS ACCESSIBLE TO MOBILE DIGITAL DEVICES

(71) Applicant: Krispin Johan Leydon, Salida, CO (US)

(72) Inventor: Krispin Johan Leydon, Salida, CO (US)

(*) Notice: Subject to any disclaimer, the term of this patent is extended or adjusted under 35 U.S.C. 154(b) by 483 days.

(21) Appl. No.: 15/799,863

(22) Filed: Oct. 31, 2017

(65) Prior Publication Data

US 2018/0064402 A1 Mar. 8, 2018

Related U.S. Application Data

(63) Continuation-in-part of application No. 15/267,108, filed on Sep. 15, 2016, which is a continuation-in-part
(Continued)

(51) Int. Cl.
*A61B 5/00* (2006.01)
*A61B 5/097* (2006.01)
(Continued)

(52) U.S. Cl.
CPC .......... *A61B 5/7278* (2013.01); *A61B 5/0015* (2013.01); *A61B 5/0022* (2013.01);
(Continued)

(58) Field of Classification Search
CPC ...... A61B 5/087; A61B 5/0002; A61B 5/0871
See application file for complete search history.

(56) References Cited

U.S. PATENT DOCUMENTS 2,794,341 A * 6/1957 Vonnegut ................. G01L 7/00
73/861.32
3,367,324 A 2/1968 De Bono
(Continued)

FOREIGN PATENT DOCUMENTS

WO 2016079336 A1 5/2016

OTHER PUBLICATIONS

Kaiser et al., Design and Learnability of Vortex Whistles for Managing Chronic Lunch Function via Smartphones, UBISOMP '16, Sep. 12-16, 2016, Pleidelberg, Germany (Year: 2016).*
(Continued)

*Primary Examiner* — Etsub D Berhanu
*Assistant Examiner* — Michael A Catina
(74) *Attorney, Agent, or Firm* — The Marbury Law Group, PLLC

(57) ABSTRACT

An acoustic device for spirometric measurement is provided. The acoustic device includes an inlet conduit configured to receive an airflow and a central cavity in communication with the inlet conduit. The central cavity includes a channel configured to guide at least a portion of the airflow into a vorticial flow about a central axis of the central cavity. The acoustic device further includes an outlet conduit configured to receive at least a portion of the vorticial flow and transduce at least a portion of kinetic energy of the vorticial flow into an acoustic emission. A frequency of the acoustic emission varies based on a rate of the airflow provided to the inlet conduit. In addition, the acoustic device includes a flow controller configured to modify at least a portion of the airflow provided to the inlet conduit.

17 Claims, 24 Drawing Sheets

Related U.S. Application Data of application No. 14/857,241, filed on Sep. 17, 2015, which is a continuation of application No. 12/924,245, filed on Sep. 22, 2010, now Pat. No. 9,138,167.

(60) Provisional application No. 62/430,011, filed on Dec. 5, 2016, provisional application No. 62/415,639, filed on Nov. 1, 2016, provisional application No. 61/246,058, filed on Sep. 25, 2009.

(51) Int. Cl.
*A61B 5/087* (2006.01)
*A61M 15/00* (2006.01)

(52) U.S. Cl.
CPC ............ *A61B 5/0026* (2013.01); *A61B 5/087* (2013.01); *A61B 5/0871* (2013.01); *A61B 5/097* (2013.01); *A61B 5/6898* (2013.01); *A61B 5/742* (2013.01); *A61M 15/009* (2013.01); *A61M 15/0021* (2014.02); *A61M 2205/3334* (2013.01); *A61M 2205/3375* (2013.01); *A61M 2205/3553* (2013.01); *A61M 2205/3584* (2013.01); *A61M 2205/3592* (2013.01); *A61M 2205/43* (2013.01); *A61M 2205/505* (2013.01); *A61M 2205/52* (2013.01); *A61M 2205/583* (2013.01); *A61M 2206/14* (2013.01); *A61M 2206/16* (2013.01)

(56) References Cited

U.S. PATENT DOCUMENTS

| | | | |
|---|---|---|---|
| 3,473,377 | A | 10/1969 | Reinecke |
| 3,714,328 | A | 2/1973 | Durkan |
| 4,182,172 | A | 1/1980 | Lennart et al. |
| 4,244,212 | A | 1/1981 | Stignani |
| 4,930,357 | A | 6/1990 | Thurston et al. |
| 5,003,828 | A | 4/1991 | Van Den Burg |
| 5,363,842 | A * | 11/1994 | Mishelevich ........ A61B 8/0875 128/200.14 |
| 5,518,002 | A | 5/1996 | Wolf et al. |
| 5,732,709 | A | 3/1998 | Tacklind et al. |
| 5,864,067 | A | 1/1999 | Ligneul et al. |
| 6,289,313 | B1 | 9/2001 | Heinonen et al. |
| 6,968,375 | B1 | 11/2005 | Brown |
| 7,063,669 | B2 | 6/2006 | Brawner et al. |
| 7,093,501 | B2 | 8/2006 | Kuo et al. |
| 7,094,208 | B2 | 8/2006 | Williams et al. |
| 7,264,591 | B2 | 9/2007 | Brown |
| 7,383,740 | B2 | 6/2008 | Krasilchikov et al. |
| 8,109,266 | B2 | 2/2012 | Addington et al. |
| 9,138,167 | B1 | 9/2015 | Leydon |
| 2005/0183725 | A1 | 8/2005 | Gumaste et al. |
| 2006/0100537 | A1 | 5/2006 | Williams et al. |
| 2006/0206036 | A1 | 9/2006 | Quinn |
| 2006/0253045 | A1 | 11/2006 | Coifman |
| 2007/0179347 | A1 | 8/2007 | Tarassenko et al. |
| 2007/0239058 | A1 | 10/2007 | Krasilchikov |
| 2008/0017097 | A1 | 1/2008 | Eventoff |
| 2009/0084380 | A1 | 4/2009 | Gieschen et al. |
| 2009/0112114 | A1 | 4/2009 | Ayyagari et al. |
| 2009/0270751 | A1 | 10/2009 | Peng et al. |
| 2009/0314292 | A1 | 12/2009 | Overfield et al. |
| 2011/0092840 | A1 | 4/2011 | Forbes et al. |
| 2013/0066225 | A1 | 3/2013 | Kojouri |
| 2013/0190641 | A1 | 7/2013 | Gonnen et al. |
| 2015/0126889 | A1 | 5/2015 | Frey et al. |

OTHER PUBLICATIONS

U.S. Appl. No. 15/267,108.
U.S. Appl. No. 14/857,241.
U.S. Appl. No. 12/924,245.
H. Sato et al., Experimental Study on the Use of a Vortex Whistle as a Flowmeter, IEEE Transactions on Instrumentation and Measurement, vol. 49, No. 1, pp. 200-205. Feb. 2000.
T. Togawa et al., Biomedical Transducers and Instruments, CRC Press excerpt, pp. 162-164, May 21, 1997.
R.C. Chanaud, Experiments Concerning the Vortex Whistle, J. Acoust., Soc. Amer., vol. 37, No. 7, pp. 953-960, 1963.
B. Vonnegut, A Vortex Whistle, J. Acoust. Soc. Amer., vol. 26, No. 1, pp. 18-20, 1954.
H. Sato et al., Application of the Vortex Whistle to the Spirometer, Transactions of the Society of Instrument and Control Engineers, pp. 840-845, V35, N7, Japan, 1999.
Written Opinion for International Application No. PCT/EP2015/077295 dated Jan. 2015.
Digidoc Technologies, medGadget, Dumb Asthma Whistle and Smartphone Measure Asthmatics' Peak Expiratory Flow, http://www.medgadget.com/2015/03/dumb-asthma-whistle-and-smartphone-measure-asthmatics-peak-expiratory-flow.html, Mar. 18, 2015.
Sato et al., Application of the Vortex Whistle to the Spirometer, U.S. Pat. No. 7,840,845, vol. 35, 1999.
DigiDoc Technologies, Mastering Asthma, http://www.asthmawhistle.com/, 2013.
Internet Medicine, The Asthma Whistle, https://youtube.com/watch?v=yU57-xLnPNY, Mar. 20, 2015.
The Economist, Heath without Wealth, https://www.youtube.com/watch?v=hmqaW4VSSHI, Nov. 24, 2015.
Intellectual Property Office Request for Grant of a Patent for GB Application 1420669.2 and International Application No. PCT/EP2015/077295, date of receipt at the International Bureau Dec. 1, 2015.
Intellectual Property Office Request for Grant of a Patent for GB Application 1515172.3 and International Application No. PCT/EP2015/077295, date of receipt at the International Bureau Dec. 1, 2015.
Goel, et al., "SprioCall: Measuring Lung Function over a Phone Call", CHI'16, ACM, San Jose, CA, 11 pages, (May 7-12, 2016).
Kaiser, et al., "Design and Learnability of Vortex Whistles for Managing Chronic Lung Function via Smartphones", UBICOMP'16, Hieidelberg, Germany, 12 pages, (Sep. 12-16, 2016).
Feldman, et al., "Prediction of peak flow values followed by feedback improves perception of lung function and adherence to inhaled corticosteroids in children with asthma", thorax.bmj.com, Thorax 2012; 67, pp. 1040-1045, (Nov. 15, 2012).
Notification of Transmittal of the International Search Report and Written Opinion of the International Searching Authority, or the Declaration for International Application No. PCT/US2016/052058 dated Dec. 8, 2016.
Kaiser et al., Design and Learnability of Vortex Whistles for Managing Chronic Lunch Function via Smartphone, UBISOMP'16, Sep. 12-16, 2016, Heidelberg, Germany.
Sato et al. Application of the Vortex Whistle to the Spirometer, vol. 35, No. 7, 840-845, 1999.
Watanabe, Vortex Whistle as a Flow Meter, Instrument and Control Engineering Department, College of Engineering Hosei University, Japan, THMP 1-6, IMTC '94, May 10-12.

* cited by examiner

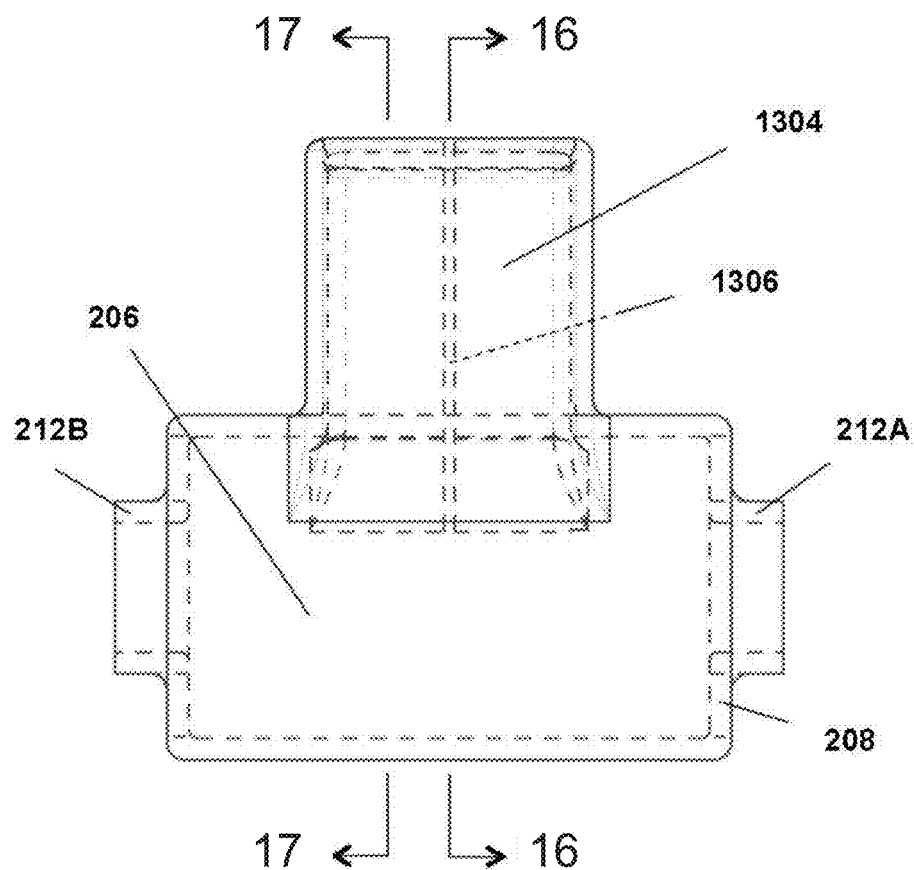
FIG. 15
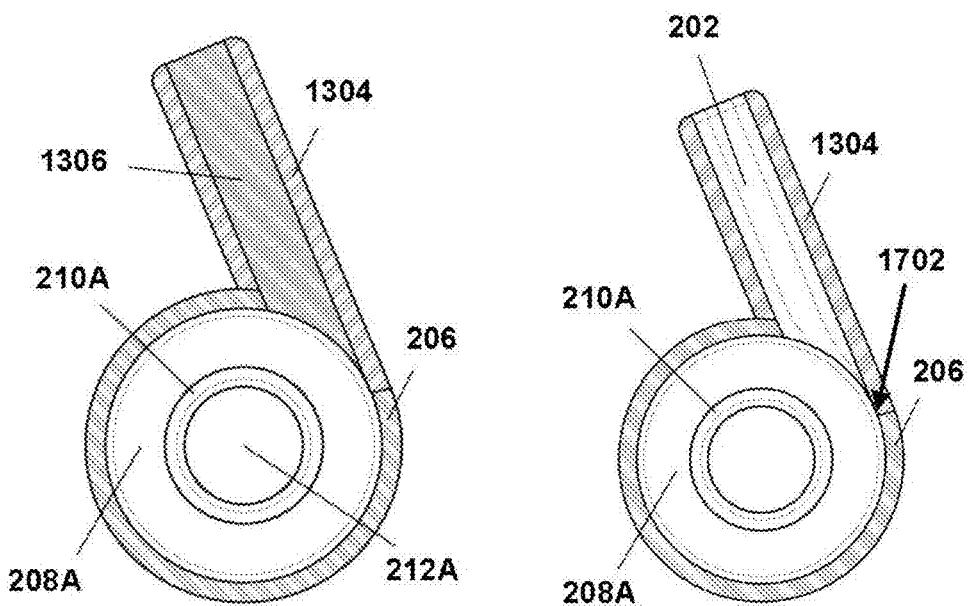
FIG. 16  FIG. 17

SYSTEMS, DEVICES AND METHODS FOR RENDERING KEY RESPIRATORY MEASUREMENTS ACCESSIBLE TO MOBILE DIGITAL DEVICES

RELATED APPLICATIONS

The application is a continuation-in-part of U.S. patent application Ser. No. 15/267,108 titled "Systems, Devices And Methods For Rendering Key Respiratory Measurements Accessible To Mobile Digital Devices" filed Sep. 15, 2016, which is a continuation-in-part of U.S. patent application Ser. No. 14/857,241 titled "Means For Rendering Key Respiratory Measurements Accessible To Mobile Digital Devices" filed Sep. 17, 2015, which is a continuation of U.S. patent application Ser. No. 12/924,245 titled "Means For Rendering Key Respiratory Measurements Accessible To Mobile Digital Devices" filed Sep. 22, 2010, now U.S. Pat. No. 9,138,167, which claims the benefit of U.S. Provisional Application No. 61/246,058 filed Sep. 25, 2009, the entire contents of all of which are hereby incorporated by reference.

This application also claims the benefit of priority to each of U.S. Provisional Application No. 62/430,011 titled "Systems, Devices And Methods For Rendering Key Respiratory Measurements Accessible to Mobile Digital Devices" filed Dec. 5, 2016, and U.S. Provisional Application No. 62/415,639 titled "Systems, Devices And Methods For Rendering Key Respiratory Measurements Accessible to Mobile Digital Devices" filed Nov. 1, 2016, the entire contents of all of which are hereby incorporated by reference.

BACKGROUND

Spirometers—devices that monitor respiration—may be used in range of clinical, domestic, and vocational situations. For example, spirometers may be used to diagnose and monitor common respiratory conditions such as asthma and chronic obstructive pulmonary disease (COPD), screen for occupational health hazards such as silicosis and black lung disease, and assist athletes and lung transplant recipients to monitor lung performance.

There are two general categories of spirometers—diagnostic spirometers and monitoring spirometers—each with its own set of requirements. Diagnostic spirometers are used in clinical settings, and are typically used to measure a number of respiratory parameters with high accuracy and precision. Monitoring spirometers are more frequently used in domestic and vocational settings; they should be cost-effective for individual users, compact, convenient, robust, low-maintenance, and designed for routine use.

Monitoring spirometers typically measure a person's peak expiratory flow rate (PEF, or PEFR), defined as the maximum volumetric airflow rate recorded during a voluntary forced expiration of air from the lungs. In addition to PEFR, another parameter measured by some monitoring spirometers is one-second forced expiratory volume ($FEV_1$): the volume of air a person can forcibly exhale over the course of one second following a deep inhalation. (The subscript in the abbreviation "$FEV_1$" indicates the duration of exhalation, in seconds.) Monitoring spirometers may also measure forced vital capacity (FVC), which may be defined as the total volume of breath exhaled during an FEV test, and forced expiratory flow (FEF) over a specified interval, e.g. $FEF_{25\%-75\%}$, the forced expiratory flow over the middle half of an FVC measurement). Portable, compact monitoring spirometers that enable a user to monitor peak expiratory flow rate are commonly referred to as "peak flow monitors." Peak flow monitors that facilitate measurement of peak expiratory flow are often referred to as "peak flow meters."

Monitoring spirometers and peak flow meters hold particular promise in the domain of asthma management. Asthma's prevalence world-wide has increased by approximately 50% per decade in recent history, and according to the World Health Organization (WHO), the human and economic burden associated with asthma surpasses that of AIDS and tuberculosis combined (2006). Approximately 300 million people world-wide suffer from asthma, and each year, asthma results in over 200,000 deaths (International Union against Tuberculosis and Lung Disease, 2005). In America alone, asthma affects 20 million people, and accounts for $14 billion in health expenditures and lost productivity each year. Asthma is the most common chronic illness among children (National Institute of Health, 2006).

Asthma is a considerable problem, and peak flow meters play a role in the asthma management strategies that physicians and medical institutions recommend. According to the National Institute of Health (NIH): "A peak flow meter can tell you when an episode is coming—even before you feel the symptoms. Taking medicine before you feel symptoms can stop the episode. People over the age of 4 with moderate or severe asthma should use a peak flow meter at least daily" (NIH Publication No. 91-2664). The "Pocket Guide to Asthma Management" (2004) published by the Global Initiative for Asthma (GINA) recommends that patients monitor peak flow "as much as possible." The National Asthma Education Program's (NAEP) 2007 Expert Panel Report highlights the value of regular PEFR readings in evaluating medications, detecting "early warning" signs, and precluding hospital visits (NIH Publication No. 07-4051). The American Thoracic Society (ATS) and National Heart, Lung and Blood Institute (NHLBI) recommend that patients with known respiratory disease regularly monitor their lung function. When a patient is able to routinely monitor his/her condition, the chances of successful management are improved.

Despite the recommendations of medical authorities, use of peak flow meters is far from ubiquitous. According to Allan H. Goroll, MD and Albert G. Mulley, MD, authors of the 2009 edition of "Primary Care Medicine", only 20% of asthma patients who stand to benefit from using a peak flow meter actually use one. In practice, availability, adoption and adherence all strongly influence the impact that existing monitoring solutions have on asthma management outcomes worldwide.

While leading physicians and medical institutions are encouraging self-care through routine peak airflow monitoring, they are not recommending that the entire burden of asthma management fall on the shoulders of individual patients. Rather, medical authorities such as the NAEP are advocating for a network-based approach to self-care, characterized by collaborative relationships between patients, physicians and family members. Within such a network-based approach, the timely sharing of health information among concerned parties is of particular importance.

There are several classes of peak flow monitoring devices. One early type of device renders a threshold expiratory airflow perceptible to end-users by means of a whistle. If the whistle sounds when the user blows into the device, the user is meant to conclude that their peak airflow is above this threshold airflow rate. The threshold can be adjusted, usually by enlarging or contracting a leak orifice situated between a mouthpiece and the whistle section of the device. The leak orifice diverts a portion of incoming airflow so that this portion does not pass through the whistle. While such devices are inexpensive, simple to use, and reward their users sonically for exhaling as forcefully as possible, their threshold values must be set properly prior to use in order to achieve valid results. Further, as threshold devices, they do not facilitate routine measurement in the manner that leading physicians and medical institutions now recommend.

The majority of peak flow meters currently available are mechanical devices with an enclosed moving element (such as a piston) connected to an externally visible pointer, positioned in close relation to a measurement scale. When a user blows into such a device, the force of his/her breath repositions the moving element, and its associated pointer points to a location on the measurement scale to indicate the user's peak expiratory flow. While such mechanical peak flow meters are simple and relatively inexpensive, friction, inertia, gravity, and other artifacts of mechanical implementation can compromise their accuracy. The need for at least one enclosed moving part has implications for reliability, ease of cleaning, and ease of sterilization. Since mechanical peak flow meters typically only display the result of the most recent measurement trial, they do not facilitate presentation of multiple trial results simultaneously—much less the visualization or exploration of trial data over a range of time scales.

In response to some of the limitations of threshold-whistle monitors and mechanical peak flow meters, electronic peak flow meters have been devised. Electronic peak flow meters typically incorporate some form of sensor, microprocessor, non-volatile memory and an LCD display. Approaches to sensing vary; some devices sense the rate at which a rotor spins in response to breath-generated airflow. Other devices sense a difference in pressure between two points along an air passageway, or the extent of Doppler shift in an ultrasound signal as it passes across an air passageway. Sensed values are usually translated into peak airflow rate values by a microprocessor, stored in non-volatile memory, and presented on an LCD display for a user to view. Electronic peak flow meters tend to be more accurate than their mechanical counterparts, and are able to store and display measurements (in some cases $FEV_1$, FVC, and other metrics, in addition to PEFR) from multiple trials. Some electronic peak flow meters also have the capability of sending measurement data to a personal computer via an attached cable or a wireless (radio-wave based) connection.

Although electronic peak flow meters typically offer greater measurement accuracy than mechanical peak flow meters, this accuracy comes at a price. Electronic peak flow meters tend to be significantly more expensive, and are also frequently less intuitive to use. To keep manufacturing costs down, user interface elements (buttons and LCD display symbols, symbol-sections and or pixels) are usually kept to a minimum—a factor that restricts ease of use. The electronic communication capabilities that some electronic peak flow meters offer are basic, and typically only possible with significant additional expense in the form of data cables, memory cards and personal computer software. Significantly, electronic peak flow meters do little at present to capitalize on advantages that software applications can provide within mobile contexts of use.

Electronic peak flow meters currently require batteries, and can run out of energy at inopportune moments—further eroding ease of use and reliability. The need for battery-powered electronics restricts how easily electronic peak flow meters can be washed and sterilized without risk of damage. While electronic peak flow meters are frequently sufficiently portable, they can become yet another battery-powered electronic device a patient must carry around on their person. In comparison with alternatives, electronic peak flow meters are more complex to manufacture and more difficult to recycle. They regularly contain toxic materials incongruous with their function as health-monitoring devices.

Some types of airflow sensors/transducers can generate acoustic oscillation solely through their static structure and fluid dynamic interactions, such as fluidic oscillators and fluidic whistles. Such devices have been designed to accommodate human spirometric measurement, as evident from the disclosures in U.S. Pat. No. 3,714,828 (1973); U.S. Pat. No. 4,182,172 (1980); U.S. Pat. No. 7,094,208 (2006); and U.S. Pat. No. 7,383,740 (2008). The spirometry solutions put forward in these patents share the advantage of minimal need for calibration. Because, however, these solutions employ fluidic oscillators as components within or attached to dedicated electronic peak flow measurement devices or systems, they typically have many of the previously discussed limitations typical of electronic peak flow meters. Further, since these solutions are ultrasonic (above the range of human hearing), they do not capitalize on audible feedback as a means to reward a user for exhaling as forcefully as possible.

One type of airflow sensor-transducer that has only been cursorily explored in the context of spirometry is that of the vortex whistle. Vortex whistles have the property that the fundamental frequency of sound waves they emit varies reliably and repeatably with the rate of fluid flow passing through them. This property makes it possible to derive a vortex whistle's through-passing airflow rate from its frequency emissions. Vortex whistles were first characterized by Bernard Vonnegut at General Electric Research Laboratory during the 1950s, and their principle of operation explained within his 1954 article "A Vortex Whistle", published by the Journal of the Acoustic Society of America (Volume 26, Number 1). Essentially, a vortex whistle channels flowing fluid (liquid or gas) into a swirling vortex, and then through an outlet tube. As the vortex exits the outlet tube, it becomes unstable, and whips around with an angular velocity comparable to its rotational velocity. It is believed that the instability of the vortex as it exits the outlet tube creates the vortex whistle's sound. Vonnegut's whistles were introduced for the application of ship and airplane speed monitoring, and have subsequently been used within the domain of industrial process control. One attempt to apply the principle of the vortex whistle within the domain of spirometery is documented in "Application of the Vortex Whistle to the Spirometer" by Hiroshi Sato, et al. in Japan's 1999 Transactions of the Society of Instrument and Control Engineers. This research probe employed a whistle of Vonnegut's design, with the aim of measuring expiratory airflow on a stationary workstation computer equipped with a microphone. While this preliminary investigation introduced the idea of using a whistle operating on the basic principle of the vortex whistle with the aim of measuring expiratory airflow, the investigation did not consider or address the requirements of a portable spirometric monitoring solution for use in mobile contexts, nor did this work overcome limitations inherent in Vonnegut's whistle design with respect to measurement of peak expiratory airflow.

While a range of monitoring spirometry solutions exists, there remains significant room for improvement, particularly in the following areas:

Communication: At present, peak flow meters are predominantly stand-alone devices that do little or nothing to support timely, convenient flow of health information throughout a patient's network of family members and physicians. In an age when networked mobile information services are commonplace, the lack of convenient mobile connectivity and structured channels of digital communication are notable shortcomings.

Visualization: Existing portable monitoring spirometry solutions frequently fail to provide concise graphical reports designed to facilitate quick, sound interpretation and effective medical treatment decisions. Further, the user interfaces for existing portable monitoring solutions do little to support exploration of trends over multiple timescales.

Ease of Use: Existing monitoring solutions currently fail to minimize the inconvenience and awkwardness of routine monitoring regimens—not only for patients, but also for family members and physicians.

Annotation: Existing peak flow monitoring devices for the most part do not assist patients to supplement automated quantitative measurement with self-reported contextual details. The ability to annotate a trial record with information such as whether the trial was performed following medication, what medication(s) were used, and other information pertaining to the trial would be of value in subsequent reviews of trial data by patients, physicians and family members.

Motivation: Operation of a peak flow meter is effort-dependent. If a patient does not routinely exhale as forcefully as they are able, or does not adhere to a measurement regimen, the most precise of measurement solutions cannot ensure accurate results. Contemporary solutions do little to reward the consistent effort required for routine expiratory airflow measurement—nor do they frame the activity of measurement in ways that invite enjoyment. Present solutions typically frame peak flow measurement as a task to be completed, when it could alternatively be framed as a game to be played, a competition to be won, a media/entertainment "snack", or the price of admission for some other form of rewarding experience administered in periodic installments.

Social Acceptability: The aesthetic/industrial design of available peak flow monitoring devices is usually clinical and utilitarian; for the most part, available devices and systems cannot easily be construed as fun, cool, elegant or fashionable. If an asthma patient feels reluctant or embarrassed to carry, hold or use a monitoring solution, it is of little value to them.

Correlation: Identifying the factors that exacerbate symptoms is a significant aspect of asthma management. Existing portable peak flow monitoring solutions do little to help patients correlate their own lung function with a range of potentially relevant environmental variables, such as local pollen count and geographic location. The ability to facilitate correlation could be beneficial not only for patients and their networks, but also for public health and medical research institutions in their efforts to understand asthma on a larger scale.

Reminding: The vast majority of monitoring solutions do not provide patients with the option of configuring and activating automated reminders that could support the routine monitoring regimens that medical authorities recommend.

Although the frequently-competing constraints of low cost, ergonomics, intuitiveness, accuracy, and reliability have been considered in the past, these constraints have not historically been balanced in ways that leverage the mobile technologies that millions of people already carry on their persons.

Adherence: State of the art spirometric monitoring solutions frequently fail to frame the activity of peak flow measurement in a manner that motivates patients to adhere to their peak flow measurement regimens. While there have been significant advances in peak flow meter design over time, none of these advances can help a patient who does not use their peak flow meter. Historically, the challenge of adherence has been chronically under-appreciated.

For all the forgoing reasons, new and improved devices and solutions for collecting, sensing, gathering, interpreting, organizing, analyzing and/or using respiratory measurements will be beneficial to consumers (e.g., athletes, patients, etc.), health-care professionals, and medical device manufacturers.

SUMMARY

The various embodiments include an acoustic device for spirometric measurement. The acoustic device includes an inlet conduit configured to receive an airflow and a central cavity in communication with the inlet conduit. The central cavity includes a channel configured to guide at least a portion of the airflow into a vorticial flow about a central axis of the central cavity. The acoustic device further includes an outlet conduit configured to receive at least a portion of the vorticial flow and transduce at least a portion of kinetic energy of the vorticial flow into an acoustic emission. A frequency of the acoustic emission varies based on a rate of the airflow provided to the inlet conduit. In addition, the acoustic device includes a flow controller configured to modify at least a portion of the airflow provided to the inlet conduit such that a relationship between the frequency of the acoustic emission and the rate of the airflow provided to the inlet conduit is non-linear.

In an embodiment, the flow controller includes one or more of a valve, a vent, an obstructor, and a force exerting element. In a further embodiment, the flow controller includes one or more of a pressure relief valve, a spillover valve, an umbrella valve, a duckbill valve, an elastomeric valve, a fluidic valve, a valve including no moving parts, an opening leading to an exterior of the acoustic device, a passageway leading to the exterior of the acoustic device, a flexible obstructor, a spring, a pivot, a hinge, a linear sliding constraint, a plug, a magnet, a weight, and a compressible gas reservoir. In another embodiment, the flow controller is further configured to dynamically alter a portion of the airflow to the outlet conduit and a vent outlet based on at least one of a flow rate, a pressure, a resistance, and an amplitude of the acoustic emissions.

In an embodiment, the acoustic device further includes a housing and the housing comprises the inlet conduit and the outlet conduit. In another embodiment, the acoustic device further includes a secondary acoustic transducer configured to receive expiratory airflow from at least one of a user's nose and mouth. The secondary acoustic transducer includes at least one of a Galton, Hartmann, Jet Edge whistle, free reed, bell, and clapper. In an embodiment, the flow controller comprises at least one of a rotational, sliding, or flexing constraint or joint. In another embodiment, the flow controller is a mechanical flow controller. In another embodiment, the flow controller comprises a fluidic flow controller, and the fluidic flow controller is configured to control the airflow through fluidic interactions.

In an embodiment, the flow controller is configured to modify at least a portion of the airflow provided to the inlet conduit without moving parts. In another embodiment, the acoustic device includes no moving parts.

In an embodiment, the flow controller is manually configurable. In a further embodiment, the manually configurable flow controller comprises at least one of a socket or hole configured to receive a key or driver, a mechanical lock configured to prevent reconfiguration, and a plug.

In an embodiment, the acoustic device further comprises one or more of a visual indicator, a human readable identifier, and a machine readable identifier corresponding to at least one characteristic or parameter of the acoustic device. In a further embodiment, the machine readable identifier comprises one or more of an RFID, NFC, QR, or bar code, a writable memory, a feature corresponding to the acoustic emission of the acoustic device.

In an embodiment, the acoustic device is configured to produce an acoustic emission having a frequency in the ultrasonic or audible range. In another embodiment, the acoustic device further comprises a second outlet conduit in fluid communication with the central cavity, wherein the second outlet conduit is configured to transduce a second acoustic emission based on the airflow provided at the inlet conduit.

In some embodiments, the acoustic device further comprises an inhaler dispenser or a dosage counter. In another embodiment, the flow controller is configured to dynamically alter an allocation of the airflow provided at the inlet conduit through the outlet conduit and a vent, such that a change in the frequency of the acoustic emission per unit change in a rate of the airflow is higher at a lower airflow rate than at a higher airflow rate.

In various embodiments, a whistle configured to generate an acoustic emission having a frequency that varies in response to a rate of an airflow for spirometric measurement is provided. The whistle includes an inlet conduit configured to receive the airflow at a first rate and a vortex chamber in fluid communication with the inlet conduit. The vortex chamber comprises a channel configured to guide at least a portion of the airflow into a vortical flow about a central axis of the vortex chamber. The whistle further includes an acoustic outlet conduit configured to receive at least a portion of the vortical flow and transduce at least a portion of kinetic energy of the vortical flow into an acoustic emission having a frequency that varies in response to a rate of the airflow provided to the inlet conduit. In addition, the whistle includes a flow controller in fluid communication with at least one of the inlet conduit, the vortex chamber, and the acoustic outlet conduit. The flow controller is configured allocate at least a portion of the airflow provided to the inlet conduit between a plurality of routes. The plurality of routes including a first route passing through the acoustic outlet conduit and a second route passing through a vent outlet.

In various embodiments, an acoustic device configured to emit an acoustic emission having a frequency that varies based on a rate of an incoming fluid flow is provided. The acoustic device includes an inlet conduit configured to receive the incoming fluid flow and a central cavity in fluid communication with the inlet conduit. The central cavity is configured to channel at least a portion of the incoming fluid flow into a vortical flow about a central axis of the central cavity. The acoustic device further includes an outlet conduit configured to receive at least a portion of the vortical flow exiting the central cavity. The outlet conduit converts at least a portion of kinetic energy of the vortical flow into an acoustic emission having a frequency that varies based on a rate of the incoming fluid flow. In addition, the acoustic device includes a flow controller in fluid communication with the inlet conduit. The flow controller is configured to receive at least a portion of the incoming fluid flow and allocate at least a portion of the received incoming fluid flow between a plurality of routes. The plurality of routes includes a first route passing through the outlet conduit and a second route passing through a vent outlet.

In various embodiments, a system that ncludes a whistle or acoustic device having a flow controller that generates an acoustic emission having a frequency in response to an airflow provided to the whistle or acoustic device having the flow controller and a hand-held mobile electronic device including a memory, a microphone, an electronic display, and a processor coupled to the memory, the microphone, and the electronic display. In some embodiments, the processor may be configured with processor-executable instructions to perform operations that include determining a baseline acoustic context, recording samples via the memory based on information received via the microphone, determining a frequency value for an acoustic signal included in the recorded samples, determining an expiratory airflow rate value based on the determined frequency value, determining a respiratory parameter based on the determined expiratory airflow rate value, generating spirometric information based on one or more of the determined frequency value, the recorded samples, the determined expiratory airflow rate value, and the determined respiratory parameter, and rendering the generated spirometric information.

In an embodiment, the processor may be configured with processor-executable instructions to perform operations that further include determining whether the acoustic signal corresponds to an acoustic emission that is generated by a user performing a forceful exhalation through the whistle or acoustic device having a flow controller based on at least one of the recorded samples, the determined frequency value, and the determined baseline acoustic context. In a further embodiment, the processor may be configured with processor-executable instructions to perform operations such that determining the baseline acoustic context further includes determining at least one of an acoustic feature of the whistle, an acoustic feature of a user performing a forceful exhalation through the whistle, an acoustic environment, and a recording device feature. In a further embodiment, the processor may be configured with processor-executable instructions to perform operations that further include determining active noises of the recorded samples based on the determined baseline acoustic context. In a further embodiment, the processor may be configured with processor-executable instructions to perform operations that further include receiving an identifier, and at least one of the operations of performing a validation based on the received identifier and identifying the correlation of the whistle based on the received identifier.

Further embodiments include methods of spirometric measurement using a whistle or acoustic device having a flow controller which may include determining, via a processor of a mobile electronic device, a baseline acoustic context, recording samples based on information received via a microphone of the mobile electronic device, determining a frequency value for an acoustic signal included in the recorded samples, determining an expiratory airflow rate value based on the determined frequency value, determining a respiratory parameter based on the determined expiratory airflow rate value, generating spirometric information based on one or more of the recorded samples, the determined frequency value, the determined expiratory airflow rate value, and the determined respiratory parameter, and rendering the generated spirometric information.

In an embodiment, the method may include using at least one of the determined frequency value, the determined baseline acoustic context, and the recorded samples to determine whether the acoustic signal corresponds to an acoustic emission that is generated by a user performing a forceful exhalation through the whistle, in which determining the expiratory airflow rate value based on the determined frequency value includes determining the expiratory airflow rate value in response to determining that the acoustic signal corresponds to the acoustic emission of the whistle or acoustic device having a flow controller. In a further embodiment, the method may include determining a physical location of the mobile electronic device, in which at least one of the operations of determining whether the acoustic signal corresponds to the acoustic emission, determining the expiratory airflow rate value, and generating the spirometric information are performed based on the determined physical location of the mobile electronic device. In a further embodiment, determining the baseline acoustic context further includes determining at least one of an acoustic feature of the whistle, an acoustic feature of a user performing a forceful exhalation through the whistle, an acoustic environment, and a recording device feature.

In a further embodiment, the method may include determining active noises of the recorded samples based on the baseline acoustic context. In a further embodiment, the method may include receiving an identifier at the mobile electronic device, and at least one of the operations of performing a validation based on the received identifier, and identifying the correlation of the whistle based on the received identifier. In a further embodiment, the method may include determining whether to limit execution of at least one of the operations of determining the frequency value for the acoustic signal included in the recorded samples, determining the expiratory airflow rate value based on the determined requency value, determining the respiratory parameter based on the determined expiratory airflow rate value, and rendering the generated spirometric information based on a result of the validation. In a further embodiment, the method may include rendering a representation of the received identifier, receiving a user input in response to rendering the representation of the received identifier, and updating at least one of the validation and the correlation based on the received user input. In a further embodiment, the method may include adding the received identifier as a valid identifier for the whistle. In a further embodiment, the method may include transmitting information to a processing and storage resource via a wireless network, the transmitted information including at least one of a recorded sample, the determined frequency value, the determined expiratory airflow rate value, the determined respiratory parameter, and a portion of the generated spirometric information. In another embodiment, the method may include transmitting the recorded samples to a processing and storage resource via a wireless network such that the processing and storage resource determines at least one of the determined frequency value, the determined expiratory airflow rate value, the determined respiratory parameter, and a portion of the generated spirometric information.

Further embodiments include a hand-held mobile electronic device that includes a memory, a microphone for receiving signals or acoustic emissions from a whistle or acoustic device having a flow controller, an electronic display, and a processor coupled to the memory, the microphone, and the electronic display. The processor may be configured with processor-executable instructions to perform operations that include determining a baseline acoustic context, recording samples via the memory based on information received via the microphone, determining a frequency value for an acoustic signal included in the recorded samples, determining an expiratory airflow rate value based on die determined frequency value, determining a respiratory parameter based on the determined expiratory airflow rate value, generating spirometric information based on one or more of the recorded samples, the determined frequency value, the determined expiratory airflow rate value, and the determined respiratory parameter, and rendering the generated spirometric information.

In an embodiment, the processor may be configured with processor-executable instructions to perform operations that further include using at least one of the determined frequency value, the determined baseline acoustic context, and the recorded samples to determine whether the acoustic signal corresponds to an acoustic emission that is generated by a user performing a forceful exhalation through the whistle or acoustic device having a flow controller, in which determining the expiratory airflow rate value based on the determined frequency value includes determining the expiratory airflow rate value in response to determining that the acoustic signal corresponds to the acoustic emission. In a further embodiment, the processor may be configured with processor-executable instructions to perform operations that further include determining a physical location of the mobile electronic device, and the processor may be configured with processor-executable instructions to perform operations such that at least one of the operations of determining whether the acoustic signal corresponds to the whistle signal, determining the expiratory airflow rate value, and generating the spirometric information are performed based on the determined physical location of the mobile electronic device. In a further embodiment, the processor may be configured with processor-executable instructions to perform operations such that determining the baseline acoustic context further includes determining at least one of an acoustic feature of the whistle, an acoustic feature of the user performing the forceful exhalation through the whistle, an acoustic environment, and a recording device feature. In a further embodiment, the processor may be configured with processor-executable instructions to perform operations that further include determining active noises of the recorded samples based on the baseline acoustic context.

In a further embodiment, the processor may be configured with processor-executable instructions to perform operations that further include receiving an identifier, and at least one of the operations of performing a validation based on the received identifier, and identifying the correlation of the whistle based on the received identifier. In a further embodiment, the processor may be configured with processor-executable instructions to perform operations that further include determining whether to limit execution of at least one of the operations of determining the frequency value for the acoustic signal included in the recorded samples, determining the expiratory airflow rate value based on the determined frequency value, determining the respiratory parameter based on the determined expiratory airflow rate value, and rendering the generated spirometric information based on a result of the validation. In a further embodiment, the processor may be configured with processor-executable instructions to perform operations that further include rendering a representation of the received identifier, receiving a user input in response to rendering the representation of the received identifier, and updating at least one of the validation and the correlation, based on the received user input. In a further embodiment, the processor may be configured with processor-executable instructions to perform operations that further include adding the received identifier as a valid identifier for the whistle. In a further embodiment, the processor may be configured with processor-executable instructions to perform operations that further include transmitting information to a processing and storage resource via a wireless network, the transmitted information including at least one of a recorded sample, the determined frequency value, the determined expiratory airflow rate value, the determined respiratory parameter, and a portion of the generated spirometric information.

Further embodiments include a non-transitory computer readable storage medium having stored thereon processor-executable software instructions configured to cause a processor in a hand-held mobile electronic device to perform operations for spirometric measurement using a whistle or acoustic device having a flow controller, the operations including determining a baseline acoustic context, recording samples based on information received via a microphone of the mobile electronic device, determining a frequency value for an acoustic signal included in the recorded samples, determining an expiratory airflow rate value based on the determined frequency value, determining a respiratory parameter based on the determined expiratory airflow rate value, generating spirometric information based on one or more of the recorded samples, the determined frequency value, the determined expiratory airflow rate value, and the determined respiratory parameter, and rendering the generated spirometric information.

In an embodiment, the stored processor-executable software instructions may be configured to cause a processor to perform operations that further include determining whether the acoustic signal corresponds to a whistle signal that is generated by a user performing a forceful exhalation through the whistle based on at least one of the recorded samples, the determined frequency value, and the determined baseline acoustic context. In a further embodiment, the stored processor-executable software instructions may be configured to cause a processor to perform operations such that determining the baseline acoustic context further includes determining at least one of an acoustic feature of the whistle, an acoustic feature of a user performing a forceful exhalation through the whistle, an acoustic environment, and a recording device feature. In a further embodiment, the stored processor-executable software instructions may be configured to cause a processor to perform operations that further include determining active noises of the recorded samples based on the determined baseline acoustic context. In a further embodiment, the stored processor-executable software instructions may be configured to cause a processor to perform operations that further include receiving an identifier, and at least one of the operations of performing a validation based on the received identifier, and identifying the correlation of the whistle based on the received identifier.

Further embodiments may include a computing device having a processor configured with processor-executable instructions to perform various operations corresponding to the methods discussed above.

Further embodiments may include a computing device having various means for performing functions corresponding to the method operations discussed above.

Further embodiments may include a non-transitory processor-readable storage medium having stored thereon processor-executable instructions configured to cause a processor to perform various operations corresponding to the method operations discussed above.

BRIEF DESCRIPTION OF THE DRAWINGS

The accompanying drawings, which are incorporated herein and constitute part of this specification, illustrate exemplary embodiment of the invention, and together with the general description given above and the detailed description given below, serve to explain the features of the invention.

FIG. 15 shows a top view of a whistle, in accordance with one or more embodiments.

FIG. 16 shows a sectional side view of a whistle, in accordance with one or more embodiments.

FIG. 17 shows a sectional side view of a whistle, in accordance with one or more embodiments.

DETAILED DESCRIPTION

Figure 1:
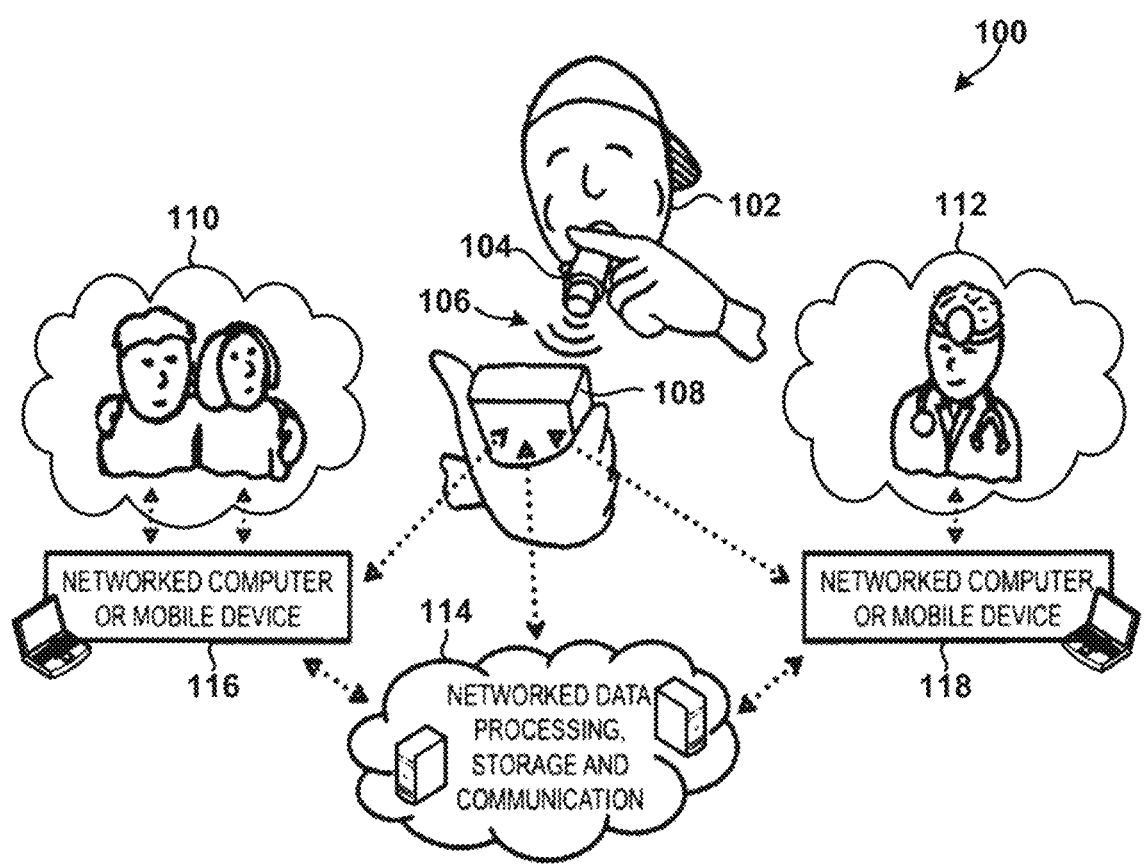
FIG. 1 is a system diagram that illustrates a spirometric measurement system for capturing, recording, and intelligently utilizing a user's expiratory measurements in accordance with various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

In overview, the various embodiments include methods, and devices configured to implement the methods, of collecting and using spirometric measurements via a whistle having a pre-determined correlation between through-flowing airflow per unit time and frequency of acoustic emissions from the whistle. A processor in a hand-held mobile electronic device may be configured to determine a baseline acoustic context, record samples in memory (e.g., based on information received via a microphone of the hand-held mobile electronic device), determine frequency value for an acoustic signal included in the recorded samples, and determine whether the acoustic signal corresponds to a whistle signal that is generated by a user performing a forceful exhalation through the whistle based on the recorded samples, the determined frequency value and/or the determined baseline acoustic context. The processor may determine an expiratory airflow rate value based on the determined frequency value (e.g., in response to determining that the acoustic signal corresponds to a whistle signal), and determine a respiratory parameter based on the determined expiratory airflow rate value. The processor may generate spirometric information based on the recorded samples, the determined frequency value, the determined expiratory airflow rate value and/or the determined respiratory parameter, and cause an electronic display of the hand-held mobile electronic device to render the generated spirometric information.

The embodiments disclosed and described in this application provide a non-conventional and non-generic arrangement of pieces/components, which are arraigned and/or configured so as to collect more accurate and more reliable spirometric measurements. As compared to conventional solutions, the particular arrangements and configurations of the various embodiments disclosed herein may increase the efficiency of collecting spirometric measurements or measuring the respiratory system of a user. The embodiments also reduce the number or quantity of resources (e.g., processing resources, battery resources, communication resources, etc.) used or consumed when collecting spirometric measurements, and generate more accurate and more reliable measurement results than most existing or conventional solutions. For all these reasons, the various embodiments improve the performance and functioning of the devices in which they are implemented. Additional benefits and improvements provided by the embodiments described in this application will be evident from the disclosures below.

The terms "hand-held mobile electronic device," "mobile electronic device," "mobile device," "portable digital device," are used generically and interchangeably herein, and may to refer to any one or all of cellular telephones, mobile phones, smartphones, personal or mobile multimedia players, personal data assistants (PDA's), tablet computers, palm-top computers, wireless electronic mail receivers, multimedia Internet enabled cellular telephones, wireless gaming controllers, personal digital assistants, mobile gaming platforms, digital watches, electronic dose counters or dispensers, electronic inhalers, and similar personal electronic devices that include a programmable processor, a memory, communications circuitry, and an acoustic input unit such as an integrated microphone, plugged-in microphone, Bluetooth wireless microphone, or electromechanical vibration transducer.

As used in this application, the terms "component," "system," "manager" and the like are intended to include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on a computing device and the computing device may be referred to as a component.

The various embodiments include/provide spirometric measurement systems for capturing, generating, measuring, determining, or making human expiratory airflow-related measurements accessible to hand-held mobile electronic devices. An embodiment spirometric measurement system may include a compact portable whistle and a physically separate hand-held mobile electronic device. The compact portable whistle may be a whistle having a pre-determined correlation between through-flowing airflow per unit time and frequency of acoustic emissions from the whistle. The hand-held mobile electronic device may be configured with processor executable instructions to perform various operations for capturing, recording, processing, analyzing and/or evaluating information and sounds generated by the compact portable whistle.

The compact portable whistle may be configured, equipped, designed or arranged to produce acoustic emissions with a frequency that varies with airflow rate. The hand-held mobile electronic device may be equipped with an acoustic input unit (e.g., an integrated microphone, plugged-in microphone, Bluetooth wireless microphone, electromechanical vibration transducer, etc.). The compact portable whistle may be configured to generate and/or send information that is suitable for deriving airflow-based measurements to the acoustic input unit of the hand-held mobile digital device. The hand-held mobile electronic device may be configured to receive, collect, and/or use information collected by the acoustic input unit to generate, compute, or determine human expiratory airflow-related measurements in a manner that is rapid, convenient, wireless, energy efficient, and battery-less (or not reliant on the whistle including a non-rechargeable or primary battery), all without any need for manual recording or data entry by a human user.

In the various embodiments, the hand-held mobile electronic device may include a processor that is configured with processor executable instructions to perform operations that include determining a user's expiratory airflow rate (e.g., PEFR, $FEV_1$, etc.) based on inputs received from the compact portable whistle (e.g., via the acoustic input unit), encoding the user's expiratory airflow rate as an acoustic frequency of emissions (or receiving encoded information), decoding the acoustic frequency of emissions to regain the expiratory airflow rate, and/or deriving respiratory parameters based on the expiratory airflow rate. The processor/device may also include circuitry for executing or performing software applications and/or any of the methods discussed in this application.

In some embodiments, the hand-held mobile electronic device may be configured to transmit or communicate captured, determined, generated or computed information (e.g., acoustic input, expiratory airflow rate, acoustic frequency of emissions, etc.) to a network server. The network server may include a processor that is configured to perform any or all of the operations discussed above. For example, the network server processor may be configured to receive raw data (e.g., acoustic frequency or emission information, etc.) from a mobile device, store the raw data in memory, and use the raw data to derive respiratory parameters (e.g., based on the captured or computed expiratory airflow rate). Thus, in some embodiments, some or all of the operations described with respect to the hand-held mobile electronic device may be performed remotely on a network (via a processor in a network server computing device, etc.) having access to data from the mobile device. In some embodiments, the operations may be performed in a distributed or co-operative fashion, such as partially on the mobile device and partially on the network server.

In some embodiments, the network server may store the computed or derived parameters and other information (e.g., human expiratory airflow-related measurements, etc.) in a network server or the "cloud" so that it is accessible to a plurality or multitude of remote users and devices. By storing such information in a central or distributed system (e.g., a database, server in the "cloud," etc.) and enabling user computing devices to access and use the information stored in this database, the various aspects enable users and devices to better identify and react to emergency conditions (e.g., asthma attacks, etc.).

In some embodiments, the spirometric measurement system and/or the hand-held mobile electronic device may be configured to perform any or all of the operations performed by a conventional dedicated portable spirometry device. In addition, the system/device may be configured to provide connectivity for inter-personal communications and data transfer; generate reminders through audio, vibrotactile and graphical means; display information through sophisticated graphical, audio and vibrotactile means; provide manual control of the spirometry operations via buttons, inertial, and/or touch screens; provide interactive feedback for motivational, instructional, editorial, aesthetic and enjoyment purposes; provide data recording, processing and storage; provide juxtaposition, combination and correlation of information from local and remote sources; provide the ability to download and incorporate additional/alternate sounds, graphics, animations and software applications; determine a baseline acoustic context; record samples; determine frequency values for acoustic signals included in the recorded samples; determine expiratory airflow rate values based on frequency values; determine respiratory parameters (e.g., based on expiratory airflow rate values, etc.); and generate/render spirometric information based on recorded samples, determined frequency values, determined expiratory airflow rate values, and determined respiratory parameters.

In some embodiments, the spirometric measurement system may be configured to present, provide, or frame the activity of peak flow measurement in a manner that motivates patients to adhere to their peak flow measurement regimens.

In some embodiments, the compact portable whistle may be configured, equipped, or arranged to reduce or minimize resistance to airflow, which improves the accuracy of the airflow-based or airflow-related measurements. For example, the compact portable whistle may be equipped with an inlet passageway having a cross-sectional area that is sized (e.g., is made sufficiently large, etc.) so that the whistle/passageway does not restrict (or does not significantly restrict, does not significantly alter, does not impact, etc.) the expiratory airflow as it passes through the whistle. The cross-sectional area may also be sized (e.g., made small enough, etc.) so as to produce acoustic emissions having an acoustic frequency within a select frequency range, so that the frequency of the generated acoustic emissions correlates with airflow rate, etc.

In some embodiments, the compact portable whistle may be configured, equipped, or arranged to have a pre-determined correlation between the through-flowing airflow per unit time and the frequency of the acoustic emissions generated by the whistle.

In some embodiments, the compact portable whistle may be configured, equipped, or arranged to transmit an acoustic signal through electrically passive means for reception by the acoustic input unit of the hand-held mobile electronic device.

An embodiment of a system and method for performing spirometric measurements will be described with reference to FIGS. 1-7.

FIG.1 illustrates an example system 100 suitable for capturing, recording, and intelligently utilizing a user's expiratory measurements in accordance with various embodiments. In particular, FIG. 1 depicts a user 102, and a whistle 104 that, when blown through forcefully by the user 102, emits sound waves 106 having a frequency that varies with the user's expiratory airflow rate in a reliable and repeatable manner. In some embodiments, the whistle 104 may be configured to emit a continuous tone with a fundamental frequency that varies with the user's expiratory airflow rate. In other embodiments, the whistle 104 may be configured to emit a series of pulses such that the pulse frequency correlates with the user's expiratory airflow rate.

FIG.1 additionally depicts a hand-held mobile electronic device 108, which may include a microphone, a display, the capability of running the process or performing the method described below with reference to FIG. 3, and the ability to communicate data (including acoustic data) over at least one wireless network. Also, in the example illustrated in FIG. 1, family members 110 and a physician 112 represent the user's asthma care network. A networked data processing, storage and communication resource 114, and computers or mobile devices owned and or operated by one or more family member(s) and physician(s) (116, 118) are also depicted in FIG. 1.

Figure 2A:
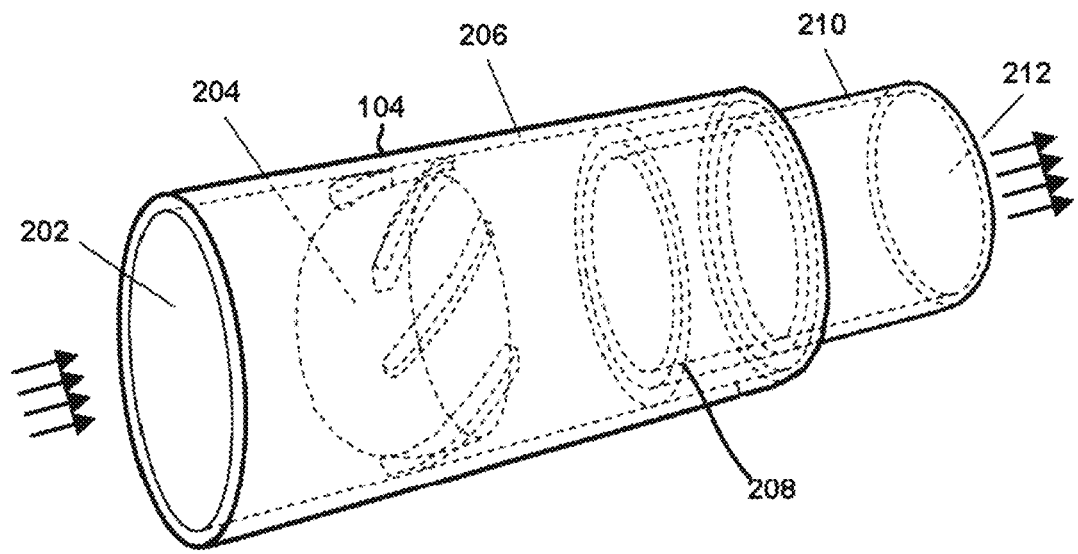
FIG. 2A is diagram illustrating an embodiment whistle that is suitable for use for capturing and intelligently utilizing a user's expiratory measurements in accordance with the various embodiments.

FIG. 2A illustrates an example whistle 104 that is suitable for use with the various embodiments. In the example illustrated in FIG. 2A, the whistle 104 includes an inlet 202, an airflow guide 204, a hollow main tube 206, an airflow constrictor ring 208, an outlet tube 210, and an outlet 212. The airflow guide 204 is situated within the whistle's hollow main tube 206 between inlet 202 and outlet 212. The airflow guide 204, together with the inner wall of the main tube 206, define several airflow passageways or channels. In other embodiments, the whistle 104 may include an airflow guide 204 in the form of one or more vanes and/or smoothly transitional surface (discussed in detail further below).

The airflow constrictor ring 208 may be configured, arranged and/or positioned to create a transition between the main tube 206 and the outlet tube 210. The outlet tube 210 may be of a decreased diameter relative to the main tube 206. In some aspects, the cylindrical cavity within the main tube 206 between the airflow guide 204 and the outlet tube 210 may be referred to as the central cavity. In some embodiments, the inlet 202 and outlet 212 of the whistle 104 may be coaxially aligned so that the net direction of airflow into the whistle 104 (e.g., into the inlet 202) is substantially the same as the net direction of airflow out of the whistle 104 (e.g., out of the outlet 212). In some embodiments, inlet 202 and outlet 212 of the whistle 104 may be perpendicularly aligned.

Figure 2B:
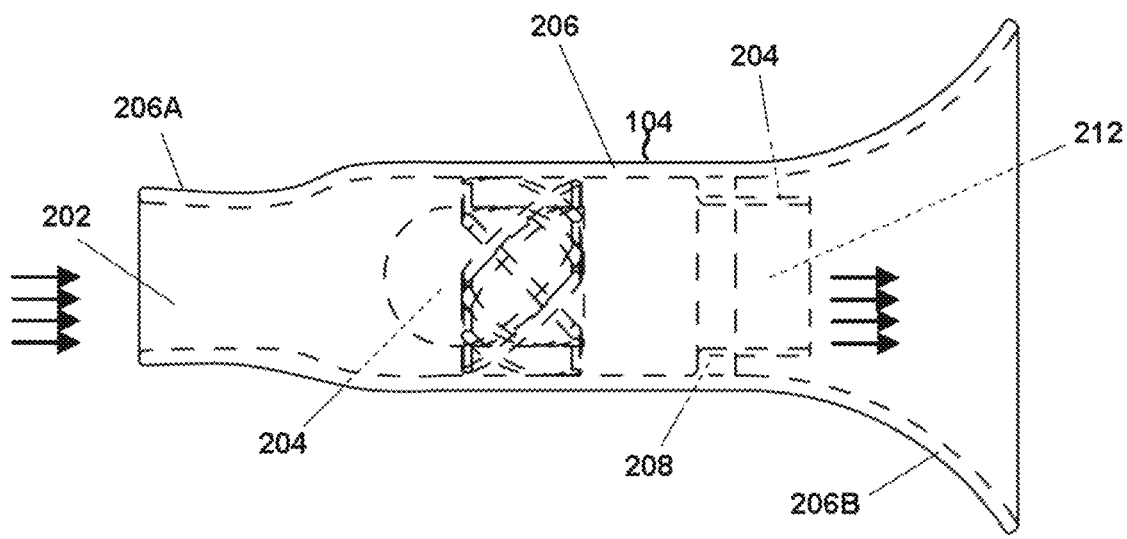
FIG. 2B is diagram illustrating another embodiment whistle that is suitable for use for capturing and intelligently utilizing a user's expiratory measurements in accordance with the various embodiments.

FIG. 2B illustrates another example whistle 104 that is suitable for use with the various embodiments. In particular, FIG. 2B illustrates that a portions or sections of the whistle 104 may be formed, shaped or tapered. The section 206A of the main tube 206 stretching from the inlet 202 to the airflow guide 204 may be formed, shaped or tapered. In some aspects, this section 206A may be referred to as the inlet-region of the main tube, the inlet tube, or the mouthpiece. FIG. 2B also illustrates that the main tube 206 may include a horn region 206B, and that the "true" outlet 212 of the whistle may be recessed inside the horn region 206B.

The horn region 206B may be shaped, formed or tapered so as to identify (e.g., via comparison) the inlet 202 of the whistle 104, and clarify which end of the whistle a user must blow through. The horn region 206B may also identify the portion (or end) of the whistle 104 that should be aimed at a mobile device (e.g., hand-held mobile electronic device 108 illustrated in FIG. 1, etc.) in order for the device to accurately capture, record, and utilize the user's expiratory measurements in accordance with various embodiments.

In some embodiments, the horn region 206B may be shaped or formed so as to provide an engaging metaphor for user interaction. The horn region 206B may be horn-shaped in some embodiments, and shaped in any of a variety of different ways in other embodiments. In addition, in some embodiments, rather than including a "horn" similar to that which is illustrated in FIG. 2B, the horn region 206B may include any of a variety of different structures, forms or shapes that function, operate or serve as a physical constraint or barrier. Therefore, nothing in this application should be used to limit the whistle 104 and/or horn region 206B to a particular structure, shape or form unless the specific structure, shape or form is expressly recited in the claims In some embodiments, the horn region 206B may be formed or shaped so as to facilitate the whistle's 104 use with the hand-held mobile electronic device 108. For example, the distance between the "true" outlet 212 of the whistle 104 and the input capture mechanism (e.g., microphone, etc.) of the mobile device may have a significant impact on the quality of the acoustic communications between whistle 104 and a hand-held mobile electronic device 108. As such, in some embodiments, the horn region 206B may be shaped or formed so as to serve as a physical constraint or barrier that prevents or discourages a user from placing the microphone of a mobile digital device too close to the "true" outlet 212.

In some embodiments, the whistle 104 may include a barrier (e.g., via the horn region 206B, etc.) that prevents or discourages a user from positioning the microphone of the mobile digital device 108 closer than about 3 mm away from the "true" outlet 212. In some embodiments, the barrier may be configured or arranged to cause or encourage a user to position the microphone of the mobile digital device 108 further than 3 mm away from the "true" outlet 212.

Thus, the shape and size of horn region 206B may be selected so that the horn region 206B operates to control the manner in which the user positions the outlet 212 relative to the microphone of a mobile device. The shape and size of horn region 206B may also be selected to ensure that the acoustic communications between whistle 104 and the handheld mobile electronic device 108 are not negatively impacted.

Generally, any interference or tampering with the airflow exiting the whistle 104 through the outlet 212 could significantly degrade the quality of acoustic communication between whistle 104 and a hand-held mobile electronic device 108 (illustrated in FIG. 1). As such, the horn region 206B also may be shaped or formed so as to serve as a physical constraint or barrier that prevents or discourages a user from touching the outlet 212 with his or her hands and/or otherwise manually interfering with airflow exiting the whistle through the outlet 212. That is, the shape and size of horn region 206B may be selected so as to ensure proper use and/or that the acoustic communications between whistle 104 and hand-held mobile electronic device 108 are not negatively impacted due to improper use.

Figure 3:
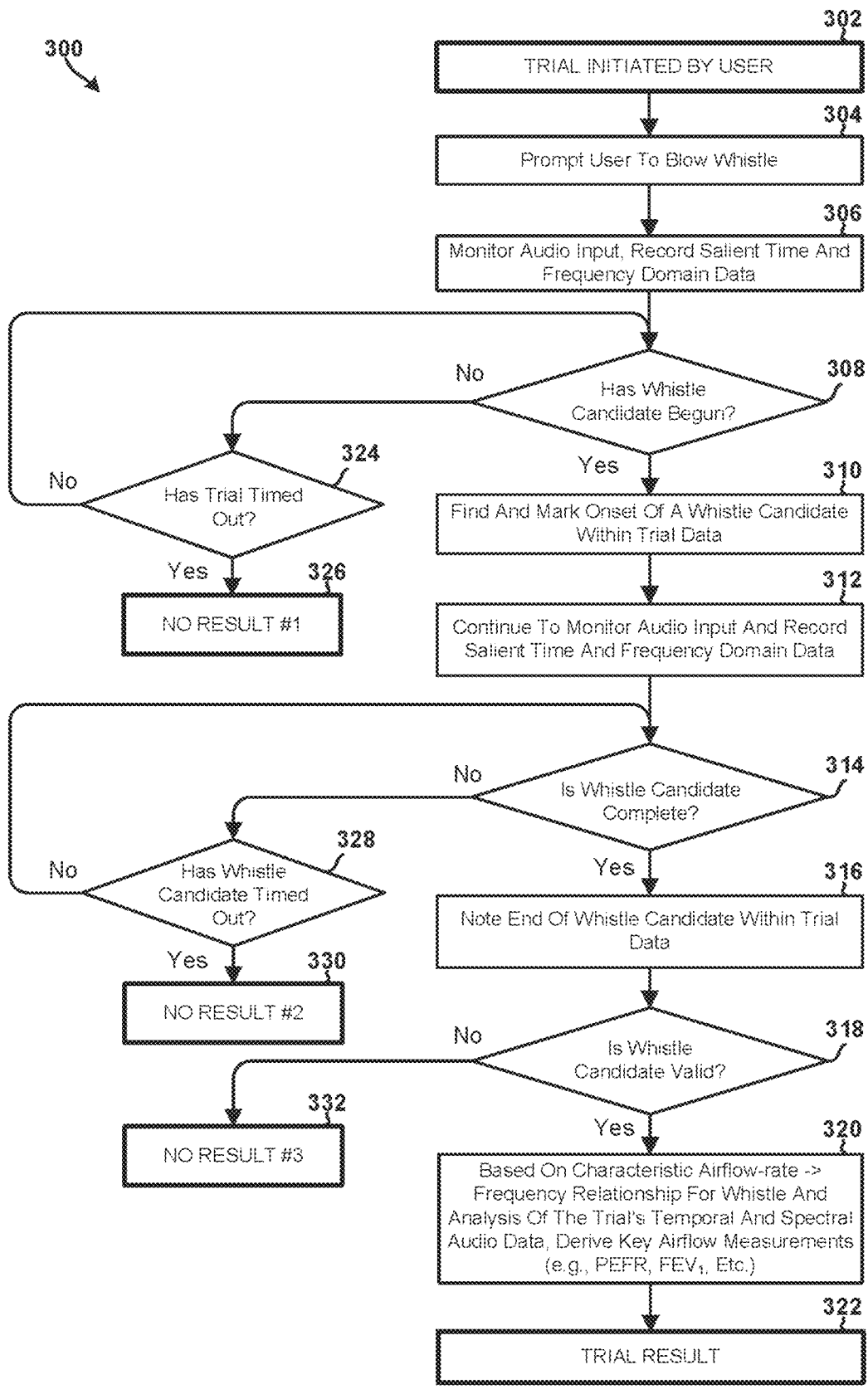
FIG. 3 is a process flow diagram illustrating a method for capturing, recording, and intelligently utilizing a user's expiratory measurements in accordance with one or more embodiments.

FIG. 3 illustrates a method 300 for performing spirometric measurements and capturing, recording, and intelligently utilizing a user's expiratory measurements in accordance with an embodiment. Method 300 may be performed by one or more processors in a mobile device (such as a mobile phone, personal digital assistant, mobile gaming system, tablet, hand-held mobile electronic device 108 illustrated in FIG. 1, etc.) or any personal electronic device that is equipped with acoustic input and networking capabilities. For example, one or more of the processors in the hand-held mobile electronic device 108 may be configured with processor-executable software instructions to perform the operations illustrated in blocks 302-332 and/or other operations for implementing method 300. The hand-held mobile electronic device may include a microphone, a display, a data recording unit, processing and storage capabilities, and an ability to communicate data over a wireless network with an external data processing and storage resource.

In block 302, a processor in a hand-held mobile electronic device may detect or receive user inputs, determine that a trial has been initiated based on the detected/received user inputs, and start a timer to record the length of the current trial. The processor may receive the user inputs in block 302 via an antenna coupled to the processor, communications circuitry of the mobile digital device, a microphone of the mobile digital device, from the actuation of user input elements, such as pressing a button or touching a virtual touch-screen button by the user, or other similar components. The processor may also receive the user inputs from the whistle in a variety of different or alternative ways (e.g., the user blowing the whistle to generate acoustic emissions, the user tapping the whistle against the screen, the user holding the whistle close to the mobile digital device, the user pressing a button on the whistle, etc.).

In block 304, the processor may prompt the user to blow a whistle (e.g., by performing operations to cause the hand-held mobile electronic device to render a prompt on its electronic display screen, etc.). For example, in block 304, the processor may cause the hand-held mobile electronic device to play a sound, display an icon, generate a vibrating alert, etc. Alternatively, in block 304, the processor may perform any of a variety of operations to communicate to the user that the device is ready to receive acoustic input (i.e., that the system is ready for the user to blow the whistle and commence a trial.

In block 306, the processor may monitor acoustic input, and collect, record and/or compute various time and frequency-domain acoustic data. As part of these operations, the processor may capture, record, or collect one set of consecutive audio samples and/or regular sets of consecutive audio samples (known as "frames"). In an embodiment, the processor may generate a collected sample information structure (e.g., data field, vector, array, table, map, etc.), and store the collected audio samples and/or frames via the collected sample information structure. Frames may be overlapping or non-overlapping. As such, the processor may record overlapping frames, non-overlapping frames, or a combination of overlapping and non-overlapping frames in block 306.

As part of the operations in block 306, the processor may determine various characteristics of the collected audio samples or frames. For example, the processor may perform "time-domain" operations, "lag domain" operations, "frequency domain" operations, filtering operations, smoothing operations, interpolation operations, sorting operations, statistical operations, etc.

In some embodiments, the processor may be configured to perform "time-domain" operations on the recorded samples in block 306. The time-domain operations may include zero-crossing detection operations and/or operations for threshold-detection with hysteresis. The processor may use the results generated from performing the time-domain operations to determine or compute a period value for a sampled audio waveform (or audio sample, frame, etc.). The processor may invert the determined period value to obtain a frequency value for the waveform. The processor may store the obtained period value or frequency value in memory.

In some embodiments, the processor may be configured to perform "lag domain" transformation operations on the recorded samples or frames in block 306. Performing the lag domain transformation operations may include performing correlation operations and/or auto-correlation operations.

The processor may use the results generated from performing the lag domain transformation operations to determine a lag value (or lag period value) corresponding to a period of the sampled audio waveform (or audio sample, frame, etc.). The processor may invert the determined lag value to obtain a frequency value for the sampled audio waveform. The processor may store the obtained lag value, period value, and/or frequency value in memory.

In some embodiments the processor may be configured to perform "frequency domain" operations and transforms in block 306. For example, the processor may be configured to perform one or more fast fourier transform ("FFT") operations in block 306. The processor may use the results of performing the frequency domain operations (e.g., FFT operations, etc.) to determine spectra corresponding to a sampled audio waveform, use the determined spectra to determine a frequency value for the sampled audio waveform, and store the determined frequency value in memory.

In some embodiments, as part the operations in block 306, the processor may perform hardware or software filtering operations or smoothing operations. These operations may be performed with respect to the time domain (e.g., by calculating a moving average, or convolving a sampled signal with a filter window, etc.) and/or with respect to the frequency domain (e.g., multiplying spectra by a filter "window," etc.).

In some embodiments, as part the operations in block 306, the processor may utilize the frequency domain transform results (e.g., results generated via the performance of FFT operations, etc.) to more rapidly perform time-domain calculations, or vice-versa (e.g., using an FFT to more rapidly calculate an autocorrelation).

In some embodiments, the processor may perform any or all of the operations discussed in this application to generate intermediate values or data that may be used for determining whether the onset of a "whistle-sound candidate"—a sound that might prove to be a valid whistle sound—has begun.

In some embodiments, the processor may poll a register or an input port of a microphone in the hand-held mobile electronic device (or any microphone coupled to the processor via direct or indirect communication links), detect the existence of sound waves or microphone input, identify various characteristics of the detected sound waves/input, determine whether the detected sound waves/input comply with select requirements (e.g., minimum requirements for a candidate, threshold requirements, etc.) based on the identified characteristics, classify the sound waves/input as a "whistle-sound candidate" in response to determining that the sound waves/input comply with the select/minimum/threshold requirements. The processor may also record or store (e.g., in a memory of the hand-held mobile electronic device via a record, table, map, etc.) one or more time values (e.g., silent time, current time, onset time, etc.) in association with the collected or determined frequency-domain acoustic data (or audio samples, frames, period values, sampled audio waveform, frequency values, etc.), and/or perform other similar operations. Such time values may be recorded or stored as values of variables, as offsets from a given time or sample, etc.

In determination block 308, the processor may determine whether a whistle-sound candidate has begun based on the collected/recorded time and frequency-domain acoustic data. In an embodiment, the processor may determine that the whistle-sound candidate has begun in response to determining that detected sound waves (or a recorded sample, frame, etc.) comply with the select or minimum requirements of a "whistle-sound candidate."

In response to determining that a whistle-sound candidate has begun (i.e., determination block 308="Yes"), in block 310, the processor may identify the whistle-sound candidate (e.g., by selecting a recorded sample classified as a potential candidate in block 306, based on the collected/recorded time and frequency-domain acoustic data, etc.), and find, identify, compute or determine the onset of the identified whistle-sound candidate. The processor may determine the onset based on detecting increases in spectral energy, based on identifying changes in the spectral energy distribution, based on comparing the captured sound waves/input (or stored data) to spectral patterns or models, etc.

In block 310, the processor may store the determined onset in memory. The onset may include information that identifies the beginning portion of a candidate sound waveform (or sample, frame, whistle-sound candidate, etc.). In some embodiments, the onset may be an information structure that includes an absolute or relative time value, a value that identifies an absolute or relative offset from a recorded sample, an index into an array of samples, an index into a data structure (e.g., collected sample information structure, etc.), and/or other similar information.

In some embodiments, as part of the operations in block 310, the processor may mark the determined onset within the recorded data (e.g., data recorded for a whistle-sound candidate or for the current measurement trial, etc.). In some embodiments, this may be accomplished by identifying and recording the approximate time, index or offset corresponding to the relevant sample or frame. Alternatively or in addition, the processor may mark the onset by setting a flag within a data structure (e.g., collected sample information structure, etc.) that includes or references the relevant sample or frame.

As mentioned above, the processor may mark the identified/determined onset within the data recorded for a trial. A "trial" may be an information structure and/or include any state, context or information that could be used by the processor to identify, request, wait for, and/or evaluate a flow-related transmission (e.g., whistle sound, collected audio samples, frames, sampled audio waveform, etc.) generated by a user or the whistle. For example, the processor could generate a "trial" information structure that includes a trial start time value, a trial end time value, a trial duration value, a collected sample, a collected frame, time and frequency-domain acoustic data, etc.

In some embodiments, the processor may be configured to evaluate only one whistle-sound candidate per trial. In other embodiments, the processor may be configured to evaluate multiple whistle-sound candidates during each trial. Certain kinds of spurious sounds may occur during the trial, even before user begins to blow the whistle. As such, the processor may evaluate multiple whistle-sound candidates during a single trial so as to prevent a spurious sound from prematurely or unexpectedly terminating the trial. Evaluating multiple whistle sound candidates during a single trial may increase the chances of successfully recognizing a valid whistle sound. As such, the processor may evaluate multiple whistle sound candidates during a single trial so as to reduce recognition errors. The processor may evaluate multiple whistle sound candidates serially, one after another, or in parallel, with a plurality of whistle sound candidates overlapping in time.

The processor may determine that a "current trial" has begun in response to determining that the whistle-sound candidate has begun, in response to determining/marking the onset of a whistle-sound candidate, or in response to receiving or detecting user input. While a trial is under way, the processor may designate any or all of the time, lag, and frequency-domain acoustic data collected for whistle-sound candidate as being part of the "current trial." In some embodiments, the processor may create a "current trial" information structure, and populate the information structure with data collected during the current trial.

The processor may determine that current trial has ended in response to determining that a whistle candidate is valid or invalid. The processor may also determine that current trial has ended in response to determining that the trial has timed out, or has been aborted, (e.g., by user input, or as a result of an event such as a phone call). After the trial is complete, the processor may mark, designate, store or reference data corresponding to the completed trial as a "previous trial." For example, the processor may generate a "previous trial" information structure, populate the "previous trial" information structure with the data collected during the (now completed) trial.

In some embodiments, consecutive trials may be managed together in sets, or "sessions"; for example, a session may consist of three consecutive trials, with the session's result being a "best of three" result. In some embodiments, trials and sessions may be represented as (independent) data objects. In some embodiments, the processor may store and increment a "trial count" value. The processor may reset the trial count value at the beginning of a session and/or after a session times out. In some embodiments, the beginning of a session may be based on the elapsed time since user activity within the context of a trial. In some embodiments, the number of trials and or sessions may be limited by a maximum number for a given time interval (e.g., 1 session per day).

Returning to FIG. 3, in block 312, the processor may continue monitoring acoustic inputs and recording relevant time and/or frequency-domain data. In determination block 314, the processor may determine whether the whistle-sound candidate has reached completion or timed out. For example, in determination block 314, the processor may compare a time value (e.g., maximum candidate time, etc.) associated with the whistle-sound candidate to a threshold value, determine whether the time value exceeds (e.g., is greater than or equal to, is less than, etc.) the threshold value, and determine that the whistle-sound candidate has reached completion or has timed out in response to determining that the time value exceeds the threshold value.

In response to determining that a whistle-sound candidate has reached completion or timed out (i.e., determination block 314="Yes"), in block 316, the processor may note/mark the end of a whistle-sound candidate with respect to the trial's time and frequency-domain data (e.g., data recorded in block 306, etc.), and generate a corresponding cessation value for the whistle-sound candidate.

Thus, after the operations in block 316, the processor has computed, determined and/or stored in memory both an onset value and a cessation value. As mentioned above, the onset value may be a numerical value that identifies the beginning of the whistle-sound candidate. Similarly, the cessation value may be a numerical value that identifies the end of the whistle-sound candidate. In some embodiments, the processor may also determine or compute a whistle-sound candidate duration value. The whistle-sound candidate duration value may be a numerical value that identifies the difference between the cessation value and the onset value, or the length of the whistle-sound candidate.

In determination block 318, the processor may determine whether the whistle-sound candidate represents a valid whistle sound or otherwise complies with various requirements of a "whistle-sound candidate." In some embodiments, this may be accomplished by computing or determining a whistle-sound candidate duration value (e.g., difference between the whistle-sound candidate cessation and onset values), identifying collected or stored time and frequency-domain acoustic data that corresponds to the determined whistle-sound candidate duration value (e.g., data recorded within the duration of the whistle-sound candidate, etc.), and examining, evaluating or analyzing the identified data to determine whether the whistle-sound candidate represents a valid whistle sound. In some embodiments, parameters derived from the whistle-sound candidate may be compared to a parametric model representing a valid whistle sound candidate. For example, a parameter of "whistle duration" may be derived from the difference between the whistle-sound candidate cessation and onset time values, and subsequently compared against a model's range of acceptable whistle durations. If the actual derived whistle duration does not fit within the model's range of acceptable whistle durations, the processor may determine that whistle-sound candidate is invalid.

In various embodiments, the processor may use any of a range of models and approaches to comparison. In some embodiments, a model for a valid whistle candidate may incorporate not only a parameter for whistle duration, but also a relative ratio between a) the average magnitude of pre-onset samples, and b) the average magnitude of samples corresponding to an interval between onset and cessation. In some embodiments, comparison between a whistle-sound candidate and a parametric model may require that some percentage of parameters match the model. In some embodiments, a determination of validity in block 318 may be made in whole or in part based on inexplicit or hidden models or parameters. For example, an artificial neural network trained on a data-set comprising valid and invalid whistle sounds may be employed to classify or support classification of a given whistle-sound candidate as valid or invalid, without relying on an explicit model of a valid whistle sound.

In response to determining that the whistle-sound candidate represents a valid whistle sound (i.e., determination block 318="Yes"), in block 320, the processor may map a frequency value derived from a whistle sound to an airflow rate, based on the whistle's characteristic relationship, or correlation, between airflow rate and frequency. The whistle's characteristic relationship (correlation) between airflow rate and frequency may be determined previous to, and outside of, the performance of method 300 (i.e. the correlation may be a pre-determined). The correlation may be stored in memory as a look-up table, array, vector, map, slope coefficient of a linear equation, a set of polynomial coefficients for a polynomial equation, etc.

In one or more embodiments, multiple pre-determined correlations between airflow rate and frequency, each corresponding to a different type or model of whistle, may be stored in memory, so as to support airflow measurement from more than one type of whistle (since each type of whistle may have its own characteristic correlation between airflow rate and frequency). In one or more embodiments, the mobile device may receive an identifier for a whistle (e.g. a serial number of the whistle manually entered by the user via a keypad, a menu entry corresponding to a type of whistle manually selected by the user via a touchscreen, a bar code on the whistle read by the mobile device, etc.) and determine, based on this identifier, which correlation (from among a set of stored, pre-determined correlations) is the appropriate correlation to use for the whistle. In this way, alternate models or types of whistles may be accommodated.

In some embodiments, once a frequency has been mapped to airflow rate within block 320 this airflow rate, or "airflow rate measurement" may be stored in memory. In some embodiments, data required to reconstruct the airflow rate measurement (e.g., a frequency, in conjunction with a known correlation between frequency and airflow rate that enables mapping frequency to airflow rate) may also or alternately be stored in memory. Also in block 320, the processor may use the airflow rate measurements to derive, determine or compute key respiratory metrics or parameters such as PEFR and $FEV_1$, and store the key respiratory metrics or parameters in memory.

In block 322, the processor may generate results (e.g. spirometric information) for the trial (which may include, or be based on, the key respiratory metrics or parameters determined in block 320). Also in block 322, the processor may make the generated trial results accessible to other entities. For example, the processor may make the trial results available to the user by causing the device (or another device) to render the results on its electronic display. The processor may also make the trial results available to the operating system, another software process/application operating on the hand-held mobile electronic device, to another mobile device, etc., whereby spirometric information may be rendered on the other mobile device. Thus, in an embodiment, the processor may render the trial results by sending the results to another component or device that receives and displays the trial results (e.g., via its electronic display, etc.).

As discussed above, in determination block 308, the processor may use the collected/recorded data (e.g., time and frequency-domain acoustic data) to determine whether a whistle-sound candidate has begun. In response to determining that a whistle-sound candidate has not yet begun (i.e., determination block 308="No"), in determination block 324, the processor may determine whether the current trial has continued for longer than a certain maximum allowed duration. For example, in determination block 324, the processor may determine whether a time value that identifies the elapsed duration of the current trial exceeds a "maximum allowed trial duration" threshold value. The processor may determine that the trial has continued for longer than the certain maximum allowed duration when the time value exceeds the "maximum allowed trial duration" threshold value.

In response to determining that the trial has not continued for longer than the maximum allowed duration (i.e., determination block 324="No"), the processor may perform the operations in block 308 and determine whether another or different whistle-sound candidate has begun (e.g., based on additional monitoring of acoustic inputs, etc.).

In response to determining that the trial has continued for longer than the maximum allowed duration (i.e., determination block 324="Yes"), in block 326, the processor may communicate to the user (e.g., by causing the hand-held mobile electronic device to display a prompt, etc.) that the trial has timed out before the onset of any whistle-sound candidate has been identified. In some embodiments, the processor may also be configured to provide the user with other feedback of a corrective, instructional, and/or motivational nature in block 326.

As mentioned above, in determination block 314 the processor may determine whether the whistle-sound candidate has reached completion or timed out. In response to determining that a whistle-sound candidate has not reached completion or timed out (i.e., determination block 314="No"), the processor may determine whether a whistle-sound candidate has continued for longer than a certain maximum allowed duration (e.g., 0.2 seconds, 0.5 seconds, 3 seconds, 5 seconds, 10 seconds, etc.) in determination block 328. For example, in determination block 328, the processor may compare a time value that identifies the duration that the whistle-sound candidate has continued (or the difference between the onset and cessation values, difference between the current time and a time when the whistle-sound candidate began, etc.) to a maximum allowed whistle-sound candidate duration value, and determine whether whistle-sound candidate has continued for longer than a certain maximum allowed duration based on the comparison results.

In response to determining that the whistle-sound candidate has not continued for longer than a certain maximum allowed duration (i.e., determination block 328="No"), the processor may return to performing the operations in block 314 to again determine whether a whistle-sound candidate has reached completion or timed out.

In response to determining that the whistle-sound candidate has continued for longer than a certain maximum allowed duration (i.e., determination block 328="Yes"), in block 330, the processor may communicate to the user (e.g., via displaying a notification message, etc.) that the trial has timed out after the onset of a potentially valid whistle-sound. The processor may also provide the user with relevant feedback of a corrective, instructional, and/or motivational nature in block 330.

In response to determining that the whistle-sound candidate does not represent a valid whistle sound (i.e., determination block 318="No"), in block 332, the processor may communicate to the user that the whistle candidate is not valid.

In various embodiments, the processor may receive one or more signals from the microphone. The one or more signals generated by the microphone may include information associated with acoustic data detected by the microphone. For example, the one or more signals generated by the microphone may include information associated with an acoustic signal generated by the whistle and/or information associated with other acoustic signals detected by the microphone (e.g., sounds generated within the environment, ambient noise, etc.). The processor may sample the one or more signals generated by the microphone to create one or more audio samples and/or frames as described above. In addition, the processor may perform various operations described above in order to determine whether information associated with an acoustic signal generated by the whistle is present within an audio sample and/or frame. Alternatively, or in addition, the processor may filter out or identify whether information associated with the acoustic signal generated by the whistle from other information is included within the one or more audio samples and/or frames. In response to extrapolating and/or detecting information associated with an acoustic signal generated by the whistle, the processor may determine or derive a frequency value of the information associated with the acoustic signal generated by the whistle such that the processor may determine an airflow rate associated with the acoustic signal generated by the whistle based on the determined or derived frequency value of the information associated with the acoustic signal generated by the whistle.

Figure 4:
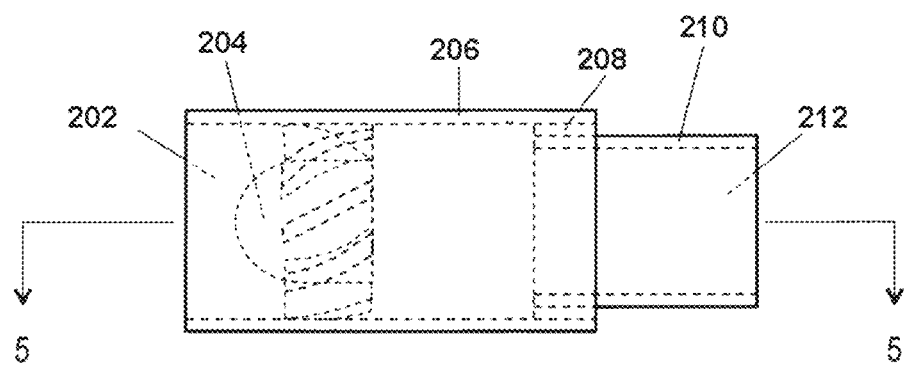
FIG. 4 shows a perspective view of a whistle, in accordance with one or more embodiments.
Figure 5:
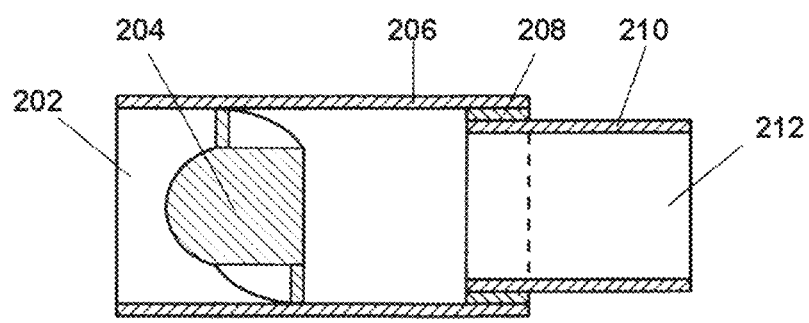
FIG. 5 shows a top view of a whistle, in accordance with one or more embodiments.
Figure 6:
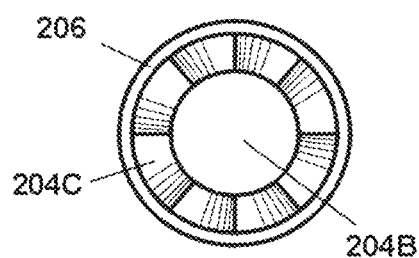
FIG. 6 shows a sectional side view of a whistle, in accordance with one or more embodiments.
Figure 7:
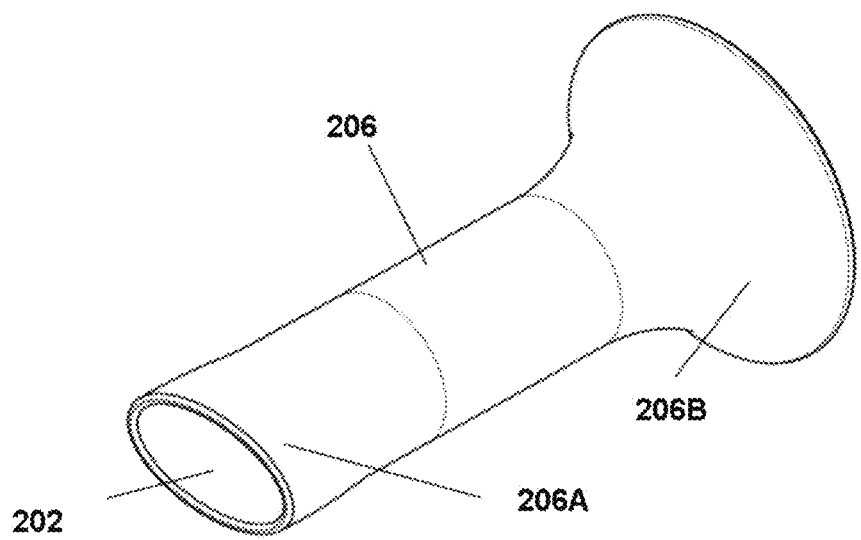
FIG. 7 shows a perspective view of a whistle, in accordance with one or more embodiments.
Figure 8:
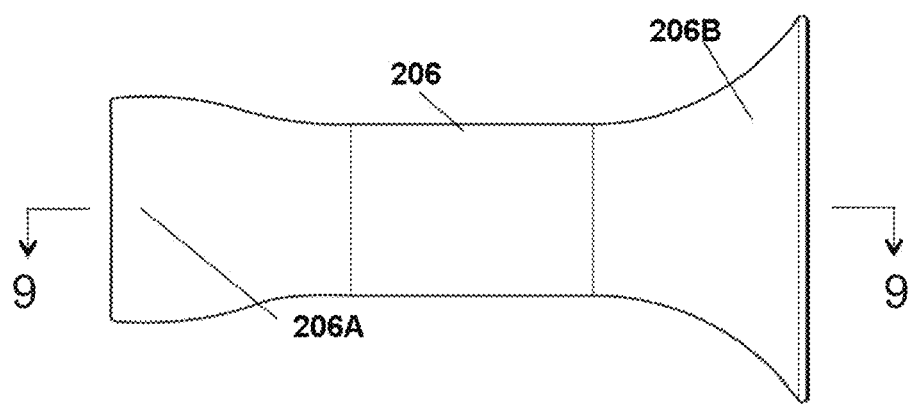
FIG. 8 shows a top view of a whistle, in accordance with one or more embodiments.
Figure 9:
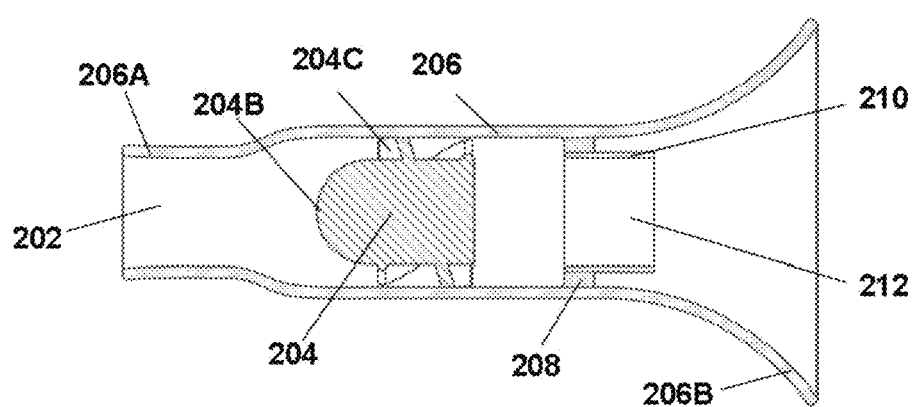
FIG. 9 shows a sectional side view of a whistle, in accordance with one or more embodiments.

FIGS. 4 through 6 illustrate various views of the whistle 104 illustrated in FIG. 2A. FIGS. 7 through 9 illustrate various views of the whistle 104 illustrated in FIG. 2B. For example, FIG. 5 illustrates a top view of the whistle illustrated in FIG. 2A. FIG. 5 also indicates the cross section for the sectional side view illustrated in FIG. 6.

FIG. 6 illustrates the rounded front face of airflow guide's center 204B and front face of an airflow guide's vane 204C.

FIGS. 7 and 8 illustrate that the whistle 104 may include mouthpiece 206A having ergonomic form. FIGS. 7 and 8 also illustrate the flaring of horn region 206B the whistle 104.

FIG. 9 illustrates the vanes of the airflow guide 204—such as one vane referenced by 204C. The front of the central portion of the airflow 204 guide is referenced by 204B. The airflow guide's vanes 204C and central portion 204B, together with the inner wall of main tube 206, define a set of airflow passageways that wind around the central axis of the whistle's central cavity.

Figure 10:
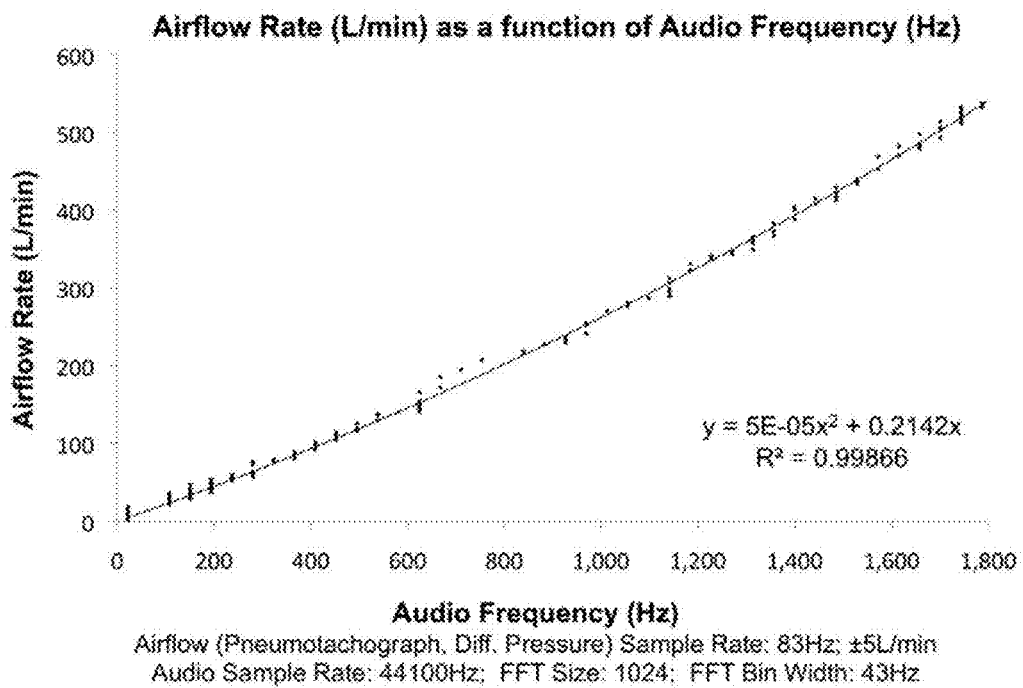
FIG. 10 shows an experimentally derived plot of the characteristic relationship between input airflow rate and output acoustic frequency for a prototype whistle, in accordance with an embodiment including a whistle similar to the whistle illustrated in FIG. 2.

FIG. 10 depicts the characteristic relationship between airflow rate and acoustic frequency for one prototype whistle similar to the whistle depicted in FIG. 2B. The relationship is experimentally derived from recorded acoustic and airflow rate data. Acoustic data may be sampled at 44.1 kHz, using a fast Fourier transform (FFT) of size 1024. Given this sampling rate and FFT size, the FFT frequency bin width is approximately 43 Hz. The presence of multiple data points at periodic acoustic frequency intervals is due to FFT frequency bin-width quantization. Airflow rate may be measured at a sampling rate of 83 Hz using a factory-calibrated differential-pressure pneumotachograph. The precision of the pneumotachograph measurements may be within ±5 L/min.

Notably, whistle frequency for this embodiment remains comfortably within an audible range. The experimentally derived relationship between airflow rate and acoustic frequency is close to linear, and can be approximated by a second-order polynomial with $R^2$=0.99866.

Figure 11:
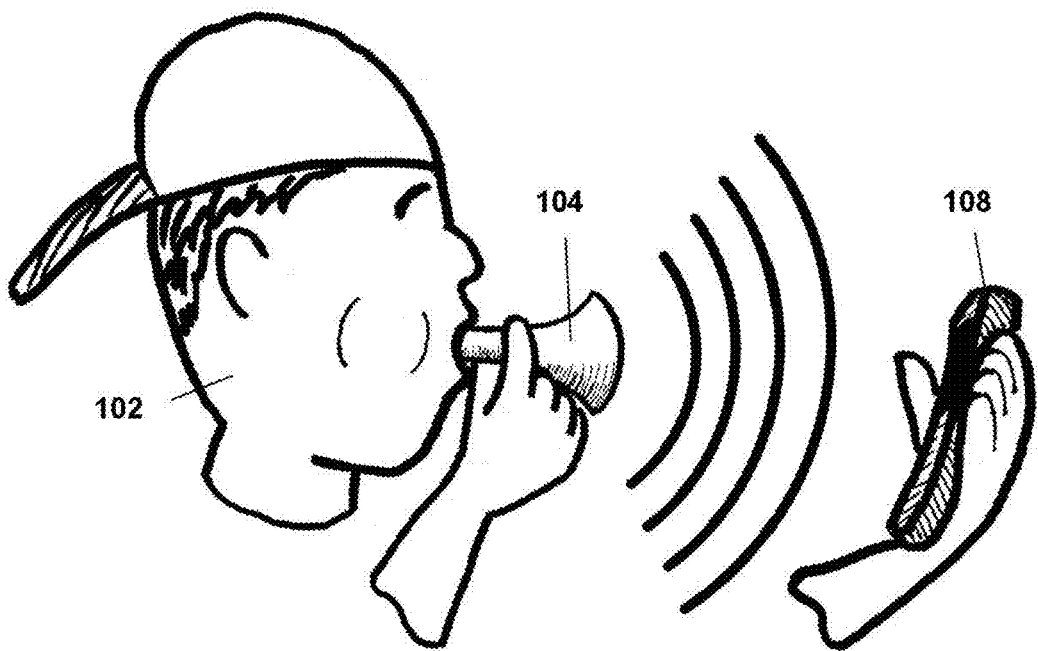
FIG. 11 is an illustration that depicts a user blowing through a whistle with a horn-shaped exterior towards a hand-held mobile electronic device in accordance with one or more embodiments.

FIG. 11 illustrates an alternate system for capturing, recording, and intelligently utilizing a user's expiratory measurements in accordance with various embodiments. Similar to example illustrated in FIG. 1, FIG. 11 depicts a user 102 blowing through a whistle 104 towards a hand-held mobile electronic device 108. However, in the example illustrated in FIG. 11 the whistle 104 includes a horn-shaped exterior, which is pointed towards the hand-held mobile electronic device 108.

An exemplary operation of spirometric measurement system according to an embodiment will now be described with reference to the figures described above (e.g., FIGS. 2B and 11).

Scenario 1: A Successful Measurement Trial

The user may initiate a measurement trial by causing a hand-held mobile electronic device (or a component or client software application operating on the device) to commence performing method 300 (described above with reference to FIG. 3). The user may express his or her intention to begin a new measurement trial by pressing a button on the hand-held mobile electronic device. In response, the hand-held mobile electronic device may prompt the user to blow the whistle (e.g., the whistle 104 illustrated in FIG. 2B, etc.). After displaying the prompt, the hand-held mobile electronic device may begin to monitor and record acoustic input. This may be accomplished by capturing and storing sound waves via its microphone and/or performing any or all of the operations discussed above with reference to block 306.

The user 102 may exhale forcibly through the inlet of the whistle, generating an airflow that is channeled by the airflow guide (e.g. vanes, transitional surface between inlet and central cavity, etc.) and through one or more airflow passageways formed by the airflow guide and the inner wall of main tube. As expiratory airflow passes through the one or more airflow passageways, a vortex may be generated within the whistle's central cavity. This vortex may pass through the remaining stages/portions of the whistle, exiting through the whistle's outlet.

As the vortex exits the outlet of the whistle, it may begin to whip around the outlet tube's central axis with an angular velocity that is comparable to its rotational velocity, thereby generating the whistle's characteristic sound. The hand-held mobile electronic device may detect, capture and record this sound. In some embodiments, the whistle may be configured such that it produces a specific sound having specific frequency characteristics, and the hand-held mobile electronic device may configured to monitor for the presence of these specific sounds or frequencies. For example, the hand-held mobile electronic device may be configured to initiate the measurement trial only in response to detecting the presence of specific sounds or waves/inputs having specific characteristics (e.g., a specific frequency range, etc.).

Next, the hand-held mobile electronic device may identify the onset of a "whistle-sound candidate"—a sound that may ultimately be determined by the device to be a valid whistle-sound. The hand-held mobile electronic device may mark the onset of the whistle-sound candidate within the trial data while continuing to monitor and record acoustic input.

As the user's forced exhalation finishes, the whistle's sound subsides. The hand-held mobile electronic device may identify the end of the whistle-sound candidate, and mark the end of this whistle-sound candidate within recorded acoustic data. Based on data recorded between the start and end of the whistle-sound candidate, the hand-held mobile electronic device may determine that the whistle-sound candidate represents a valid whistle-sound. The hand-held mobile electronic device may use the whistle-sound's acoustic frequency data—in conjunction with the whistle-device's characteristic relationship between airflow-rate and frequency—to derive measurements for PEFR and $FEV_1$. The hand-held mobile electronic device may subsequently make these results available to entities outside the current component, application and/or device.

Once the results have been made available to the user and other applications running on the device, these results can be made available to remote digital devices and services on one or more of the mobile device's network(s) for the purposes of informing family members and physicians, and maintaining a secure and accessible record of completed trials.

Scenario 2: A Trial Times Out Before a Whistle-Sound Candidate has Begun

In the event that a user initiates a trial (e.g., the device commences performing method 300), but the hand-held mobile electronic device does not identify the onset of a whistle-sound candidate within a maximum time period, the trial times out. After timing out, the device communicates to the user that the trial has timed out. The device may then offer or present to the user relevant recommendations on how to avoid timing out during future trials.

Scenario 3: A Trial Times Out After a Whistle-Sound Candidate has Begun

In the event that the hand-held mobile electronic device identifies the onset of a whistle-sound candidate, but does not identify cessation of the whistle-sound candidate within a certain maximum allowable duration, the trial times out. After timing out, the device communicates to the user that it has timed out, and offers relevant recommendations on how to avoid timing out during future trials.

Scenario 4: A Whistle-Sound Candidate is Determined Invalid

In the event that the hand-held mobile electronic device identifies the onset and cessation of a whistle-sound candidate, the hand-held mobile electronic device determines whether or not the candidate represents a valid whistle-sound. If the data for the candidate does not meet criteria required for a valid whistle-sound, the hand-held mobile electronic device may offer or present to the user relevant recommendations for how to improve the chances of completing successful trials in the future.

Details of embodiments of the present invention may vary considerably without departing from the basic principle of the present invention. For instance, the whistle could take a different form.

In some embodiments, the whistle may include a medicine dosage dispenser. This combined whistle-dispenser may reduce the total number of asthma management-related items a patient must carry on his or her person.

Figures 12A, 12B:
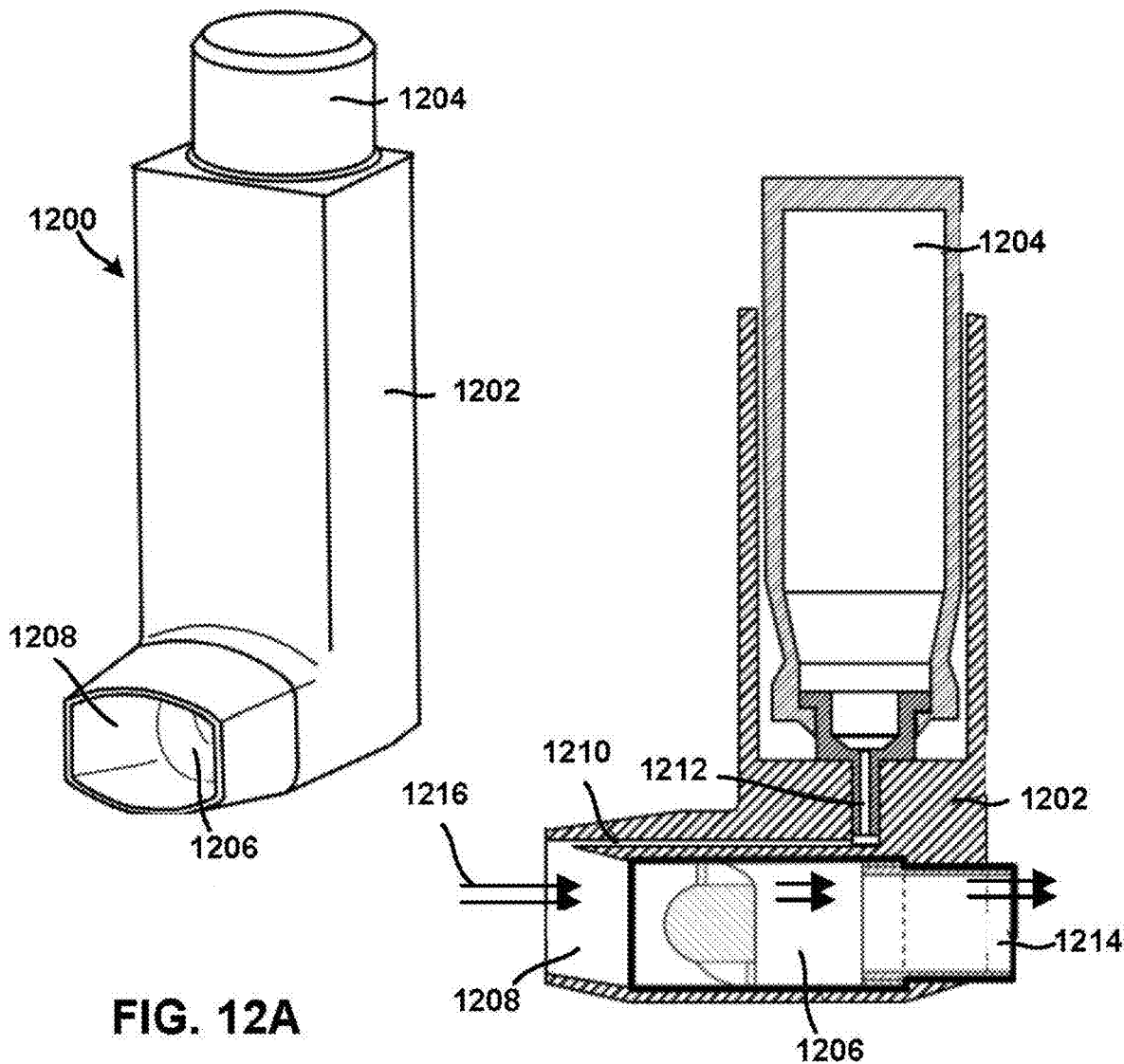
FIG. 12A depicts a perspective view of a whistle combined with a medicine dosage dispenser, in accordance with one or more embodiments.
FIG. 12B shows a sectional view of the combination of whistle and medicine dosage dispenser depicted in FIG. 9.

FIGS. 12A and 12B illustrate an example combined whistle-dispenser 1200 that is suitable for use with the various embodiments. FIG. 12A illustrates the combined whistle-dispenser 1200 includes a housing 1202, a recess for holding a standard medicine container 1204, a whistle 1206 similar to the previously discussed whistle depicted in FIG. 2A, and mouthpiece 1208. The combination whistle-dispenser 1200 may further include a delivery channel 1210 for medication that connects the medicine container's nozzle 1212 with the whistle-dispenser's mouthpiece 1208. FIG. 12B also illustrates that airflow 1216 entering the mouthpiece 1208 may pass through the whistle 1206 and out an airflow outlet 1214, generating a sound that is suitable for capture and use in accordance with the various embodiments.

When the medicine container 1204 is pushed into its recess, a dosage of medicine is dispensed through the whistle-dispenser's mouthpiece 1208. When a user exhales forcefully through the whistle-dispenser's mouthpiece 1208, all expiratory airflow passing through the mouthpiece 1208 passes through the whistle 1206, which contributes to the generation of sound.

Figure 13:
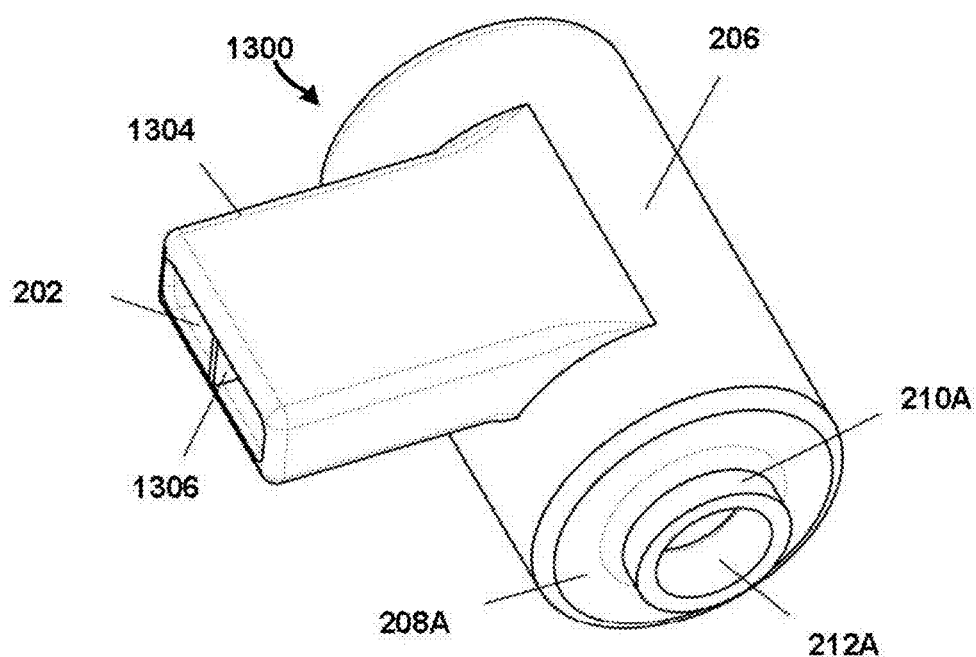
FIG. 13 is diagram illustrating another embodiment whistle that is suitable for use for capturing and intelligently utilizing a user's expiratory measurements in accordance with the various embodiments.
Figure 14:
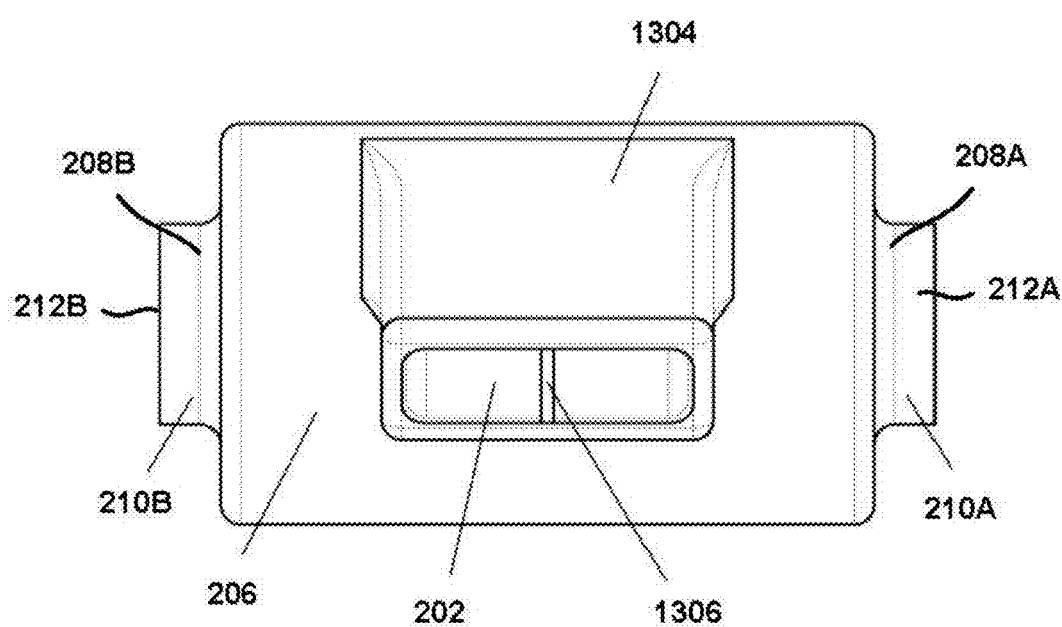
FIG. 14 shows a front view of another embodiment whistle (inlet facing the viewer) that is suitable for use for capturing and intelligently utilizing a user's expiratory measurements in accordance with the various embodiments.

FIG. 13 displays a perspective view of another whistle 1300 that is suitable for use with the various embodiments. FIG. 14 depicts a front view of the whistle 1300 illustrated by FIG. 13, and serves to highlight the whistle's lateral symmetry in this embodiment.

With reference to FIGS. 13 and 14, the whistle 1300 may include an inlet 202, an inlet tube 1304, an inlet tube partition 1306, a main tube 206, a first airflow constrictor ring 208A, a second airflow constrictor ring 208B, a first outlet tube 210A, a second outlet tube 210B, a first outlet 212A, and a second outlet 212B. The whistle 1300 may also include an airflow guide in the form of a smoothly transitional surface and/or a transition between the inner upper wall of the inlet tube 1304 and the inner wall of main tube 206 that guides expiratory airflow from inlet tube 1304 into main tube 206.

The whistle 1300 has one inlet 202 and two outlets 212 (only the first outlet 212A is visible in FIG. 13). Situated between inlet 202 and outlets 212A and 212B, there is an inlet tube (or mouthpiece) 1304, leading to a main tube 206, having a cylindrical cavity. An inlet tube partition 1306 bisects the inlet tube 1304. A pair of airflow constrictor rings 208A and 208B serve to create a transition between the larger-diameter hollow main tube 206 and the smaller-diameter outlet tubes (i.e., first outlet 212A and second outlet 212B). The airflow constrictor rings 208A and 208B, in conjunction with the wall of the main tube 206, further serve as a barrier, creating a minimum spacing between the whistle outlet tubes 210A and 210B and the user's hand (and/or the device's microphone) from at least one direction of approach. The whistle's outlets 212A and 212B and constrictor rings 208A and 208B may be symmetric about the inlet tube's partition 1306, and thus share a common central axis.

FIG. 15 illustrates a top view of the whistle shown in FIG. 13, and indicates cross sections for the sectional views illustrated by FIGS. 16 and 17.

FIG. 16 illustrates a cross-sectional side view of the whistle shown in FIG. 13. From FIG. 14, the shape of the inlet tube partition 1306 can be observed.

FIG. 17 depicts a cross-sectional side view of the whistle shown in FIG. 13, and illustrates how the (partitioned) passageway of the inlet tube 1304 intersects with the central cavity of the main tube 206. Notably, the transition 1702 between the inner upper wall of the inlet tube 1304 and the inner wall of main tube 206 is smoothly continuous, presenting no angular bend or surface discontinuities in the face of incoming airflow.

An exemplary operation of spirometric measurement system using a whistle, such as the whistle as shown in FIGS. 13-17 will now be described. It will be understood that a whistle as shown in FIGS. 13-17 may have a characteristic relationship between airflow rate and acoustic frequency, similar to the relationship shown in FIG. 10 and may be used in conjunction with the performance of method 300 illustrated in FIG. 3.

With reference to FIGS. 13-17, when a user exhales forcibly through the whistle, expiratory airflow passes through inlet tube 1304, guided by the inlet tube's walls and inlet tube partition 1306, and into the central cavity of main tube 206. The inlet tube partition 1306 encourages laminar flow through the inlet tube 1304, while the continuous, seamless transition between the inner wall of the main tube 206 the upper inner wall of the inlet tube 1304 prevents undesirable turbulence (which could increase airflow resistance and degrade acoustic signal quality) as airflow enters the central cavity.

As expiratory airflow passes from inlet tube 1304 into main tube 206, the continuous surface of the inner wall of the main tube 206 may guide airflow into a swirling vortex within the central cavity of the main tube 206. This vortex may exit the whistle through the two outlet tubes 210A and 210B. As the vortex exits outlet tubes 210A and 210B, it may begin to whip around their common central axis with an angular velocity comparable to the rotational velocity of the vortex, thus generating auditory emissions.

The lateral symmetry and right-angle inlet/outlets geometry of this whistle design support, allow, or enable a user to hear the whistle clearly, in full stereo, i.e., with each ear equidistant from one of the outlets. Additionally, the right-angle geometry decreases the chances that the microphone of a mobile device will be held too close to an outlet—an orientation that may in some situations compromise signal transmission between whistle and mobile device.

FIGS. 18-21 illustrate another example whistle that is suitable for use with the various embodiments. To reduce manufacturing cost and complexity, this whistle variation is composed of just two parts or components: a first, or top portion 220, and a second, or bottom portion 221.

This whistle variation incorporates an upward-facing outlet 212 with potential advantages including: a) directing auditory feedback to both ears of a user, b) enabling tactile feedback (i.e., wind and heat from a user's expiration) to be sensed by a user's hands or face, and c) decreasing the chances that a mobile device will be held too close to the outlet of the whistle (which may in some situations compromise acoustic signal transmission between a whistle and a mobile device).

This whistle variation further incorporates a horn-shaped "false" outlet (220E and 221E), to support a user's perception of blowing/aiming "straight through" the whistle at a mobile device, independent from of the actual direction of airflow as it exits the whistle. The horn-shaped false outlet additionally clarifies for the user which end of the whistle to blow through, and which end of the whistle may be aimed at the mobile device. The geometry of the first and second components (e.g., top portion 220 and bottom portion 221), particularly the false outlet (220E and 221E), further acts as a barrier, creating a minimum spacing from at least one direction of approach, between outlet 212 and the microphone of the mobile digital device while the whistle is in use.

Figure 18:
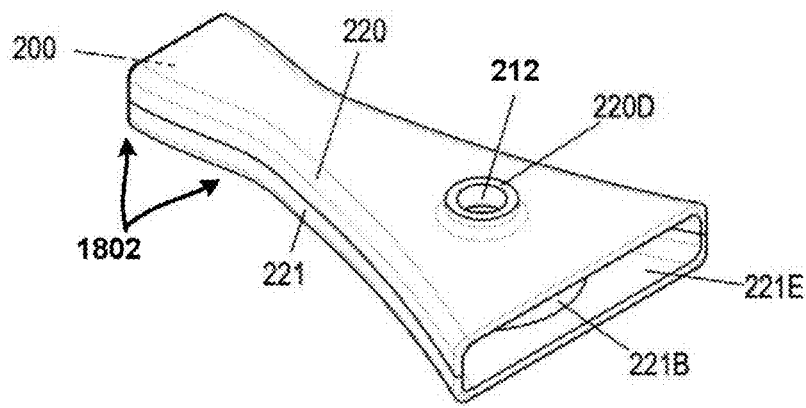
FIG. 18 shows a perspective view of a whistle, in accordance with one or more embodiments.

Additionally, the whistle embodiment of FIG. 18 depicts a grip region 1802 that is shaped to facilitate a user holding the whistle securely and to clarify where and how to hold the whistle.

Figure 19:
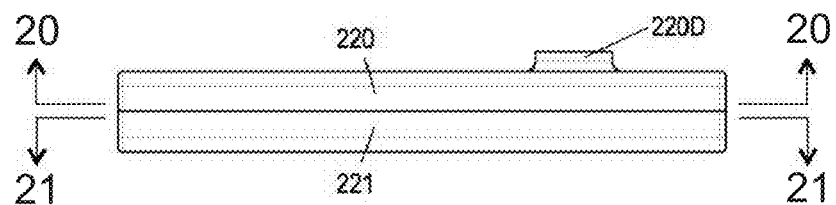
FIG. 19 shows a side view of a whistle, in accordance with one or more embodiments.

FIG. 19 displays a side view of the whistle shown in FIG. 16, and indicates the cross sections for the sectional views illustrated by FIGS. 18 and 19.

Figure 20:
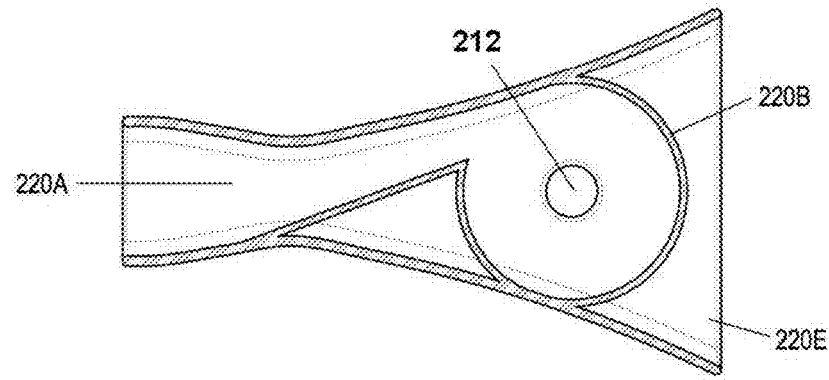
FIG. 20 shows a sectional bottom view of a whistle, in accordance with one or more embodiments.
Figure 21:
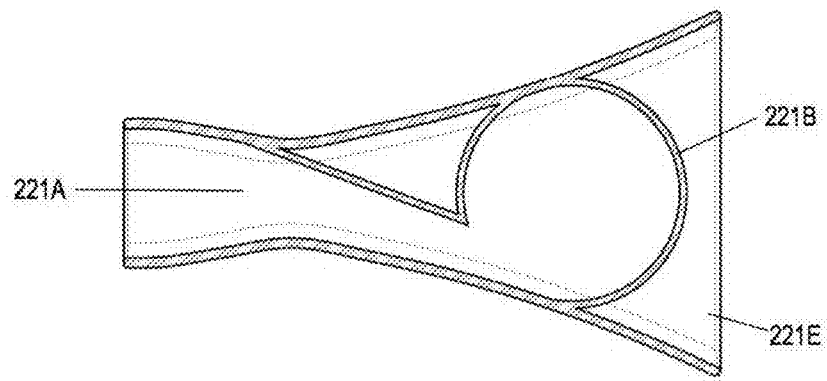
FIG. 21 shows a sectional top view of a whistle, in accordance with one or more embodiments.

FIGS. 20 and 21 are sectional bottom and top views of the whistle shown in FIG. 18 that together illustrate the whistle's initial airflow passageways. Inlet passageway region (220A/221A) allows for a comfortable, ergonomic seal with a user's lips, accepts a user's expiratory airflow, and directs airflow to the perimeter of the cavity circumscribed by main chamber (main cavity) region sidewall (220B/221B). As with the whistle variation illustrated in FIGS. 13-17, the transitional surface from inlet passageway wall to main chamber sidewall (main tube wall in FIGS. 11-15) that guides airflow from inlet into main chamber is smoothly continuous, with advantages of eliminating unwanted turbulence, reducing airflow resistance and contributing to a clear acoustic signal.

While the main chamber sidewall of this variation follows a circular path, it can be noted that other whistle variations within the scope of this invention may include sidewalls that follow alternately-shaped paths, some of them continuously variable. For example, a logarithmic curve path, such as those employed in volute-style water pumps and compressors.

An exemplary operation of spirometric measurement system using a whistle as shown in FIGS. 18-21 will now be described. It will be understood that a whistle as shown in FIGS. 18-21 may have a characteristic relationship between airflow rate and acoustic frequency similar to the relationship shown in FIG. 10 and may be used in conjunction with a software process such as illustrated by FIG. 3.

When a user exhales forcibly through the whistle illustrated by FIGS. 18-21, expiratory airflow may pass through inlet passageway region 220A/221A. This gradually tapered passageway may direct a user's expiratory airflow toward the perimeter of the cylindrical cavity circumscribed by 220B/221B.

Expiratory airflow may be guided by the smoothly continuous transition surface from 220A/221A's outer wall to 220B/221B, and may subsequently be guided by the walls of 220B/221B into a swirling vortex within 220B/221B's central cylindrical cavity; a vortex that may exit the whistle through outlet tube region 220D. As the swirling vortex exits outlet 212, it may begin to whip around the central axis of 220D with an angular velocity comparable to the rotational velocity of the vortex, thus generating the whistle's characteristic sound.

It can be readily appreciated to one skilled in the art that this whistle variation may be employed in place of other whistle variations, without departing from the basic principle of the present invention, to arrive at alternate embodiments of the invention as a whole.

Details of embodiments of the present invention may vary considerably without departing from the basic principle of the present invention. Further refinements made for engineering, industrial design, interaction design, manufacturability and standards-conformance purposes, for example, may change proportions, dimensions, time-out durations, orientations, and numerous other characteristics.

Within the whistle depicted in FIGS. 2B, 4, 5 and 6, for example, the number, angle, curvature and shape of its airflow guide's vanes 204C may change. Instead of, or in conjunction with vanes 204C, holes may be employed to guide airflow. The whistle aspect of one or more embodiment may comprise a fluidic oscillator with a frequency, such as a pulse frequency, that varies with airflow rate, instead of, or in conjunction with, a whistle operating on the principle of a vortex whistle.

Figure 22:
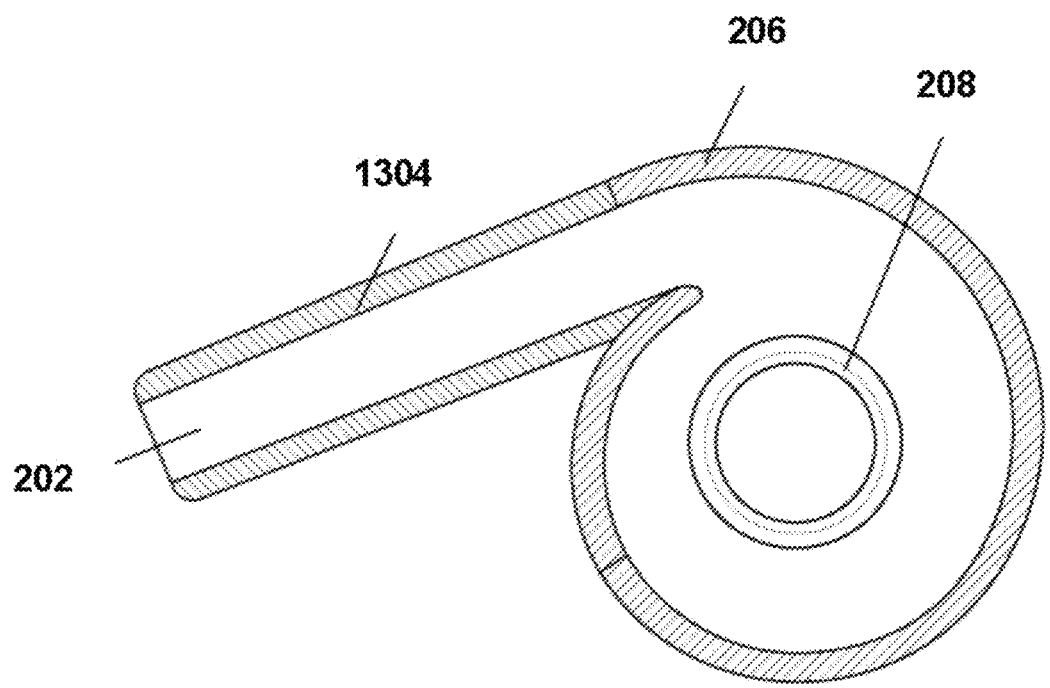
FIG. 22 shows a sectional side view of a whistle, in accordance with one or more embodiments.

Within the simplified sectional side view of the whistle depicted in FIG. 22 (a variation on the sectional side view of the similar whistle shown in FIG. 13), the wall for main tube 206 is non-cylindrical; it follows a non-circular path of continuously variable radius that directs airflow into a vortex efficiently, reducing resistance to flow and improving acoustic emissions by reducing undesirable turbulence.

Figure 23:
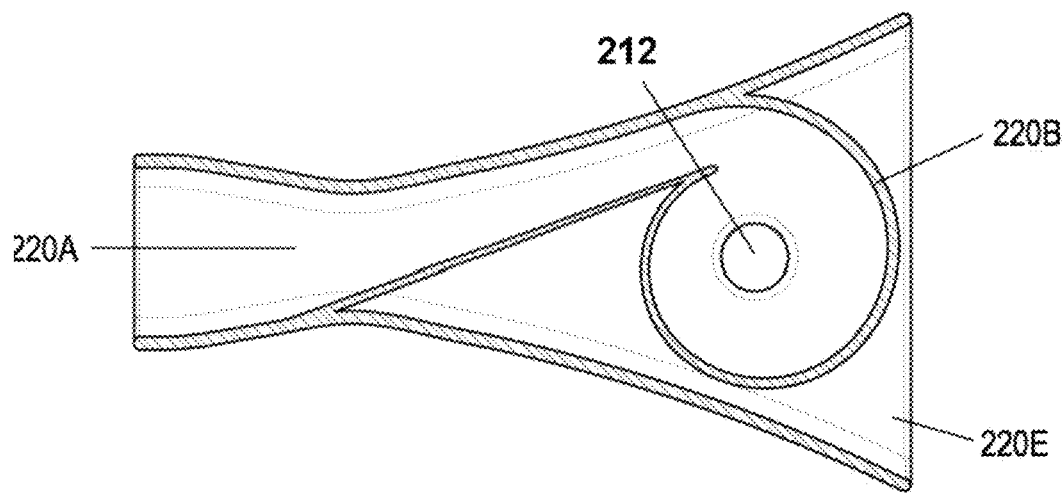
FIG. 23 shows a sectional bottom view of a whistle, in accordance with one or more embodiments.

Similarly, within the simplified whistle sectional bottom view depicted in FIG. 23 (a variation on the sectional bottom view of the similar whistle shown in FIG. 20), the main chamber (main cavity) region side-wall (220B/221B) is also non-cylindrical, and follows a path of continuously variable radius which directs airflow into a vortex efficiently, reducing resistance to flow and improving acoustic emissions by reducing undesirable turbulence.

Figure 24:
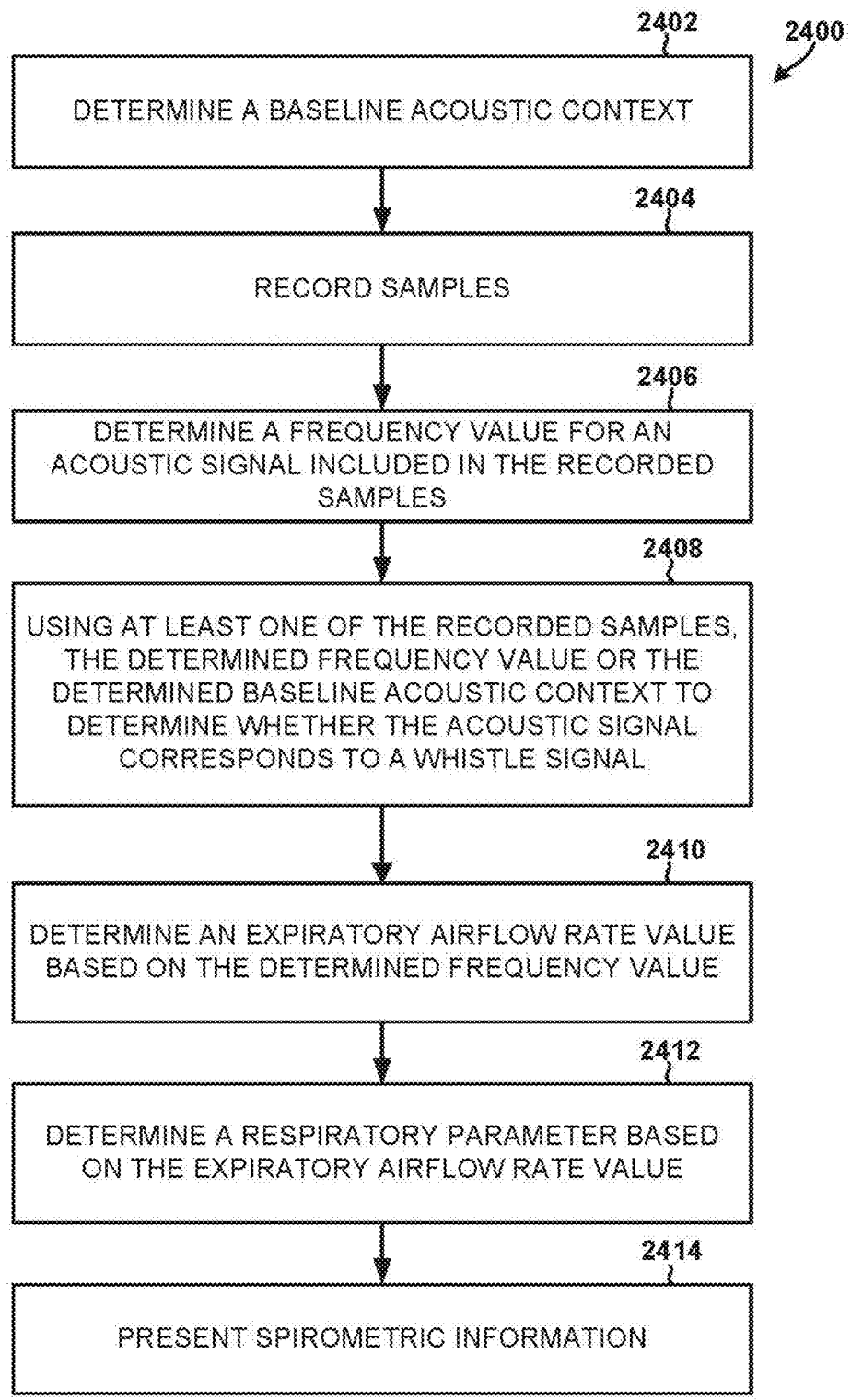
FIG. 24 is a process flow diagram illustrating a method for capturing, recording, and intelligently utilizing a user's expiratory measurements in accordance with an embodiment.

FIG. 24 illustrates a method 2400 for performing spirometric measurements and capturing, recording, and intelligently utilizing a user's expiratory measurements in accordance with an embodiment. Similar to the method illustrated and discussed above with reference to FIG. 3, the method 2400 may be performed by one or more of the processors in the hand-held mobile electronic device 108, or performed by one or more of the processors in the hand-held mobile electronic device in cooperation with an external networked processor (e.g. "cloud" computing resource).

In block 2402, a processor in a hand-held mobile electronic device may monitor and/or collect/record the acoustic environment using a microphone of the hand-held mobile electronic device to determine a baseline acoustic context used for measuring a whistle signal produced by a whistle with the spirometric measurement capabilities. The baseline acoustic context may be an information structure that includes one or more data files, variables, and/or information structures. The processor may employ any combination of the techniques described in the application to determine or generate the baseline acoustic context. Further, the processor may collect and establish acoustic information regarding the baseline acoustic context in various ways, and the collecting of information may occur before, after, in-between, continuously, and/or concurrent to the recording operations of block 2404.

In some embodiments, a range of features may potentially be identified, tracked and evaluated during generation/definition of a baseline acoustic context. These features may include features of known acoustic information of the whistle, use of the whistle by the user, acoustic environment, recording device features (e.g. hardware and/or software microphone gain), etc. In some embodiments, the acoustic information may include information and values that identify: mean, median and maximum acoustic amplitude, the absolute value of the mean, median, and/or maximum acoustic amplitude, a spectral envelope, a noise threshold, dominant spectral peaks, a frequency centroid, a normalized low-frequency energy ratio, and periods of regular periodic alternating silence and noise. In an embodiment, the baseline acoustic context may be defined to track maximum acoustic amplitude for a period of time. The processor may use this maximum acoustic amplitude as a threshold for distinguishing periods of silence from whistle candidates. In some embodiments, the baseline acoustic context may include variations of the acoustic information based on knowledge of the atmospheric pressure at the mobile device. For example, historical use of the whistle may establish a baseline use at certain frequencies for the user and/or atmospheric pressure at the time of the baseline establishment. In some embodiments, the baseline acoustic context may be defined by a user's capability to generate the above acoustic information, such as certain frequencies over a period of time.

In some embodiments, acoustic environment includes acoustic sounds, representations of acoustic sounds, or features of acoustic sounds (e.g. spectral distributions, noise levels, etc.) present within the environment surrounding the mobile device, as well as various deviations to acoustic sounds based on environmental knowledge. For example, various environments may include known (e.g., grandfather clock chimes, sirens, etc.) or louder background noises (e.g., parties, music, etc.). In other examples, the various environments may include known deviations to acoustic signals such as echoes (e.g., in a large concert hall) or atmospheric pressure changes (e.g., inclement weather).

In some embodiments, the recording device features may include explicit or implicit assumptions about the mobile device's audio subsystem (e.g., hardware or software microphone gain, sensitivity, distortion, clipping point, noise level, etc.) and/or context of use (e.g., further capabilities of the microphone of the mobile device). For example, known distortions could be accounted for in recorded samples by removing such distortions.

Returning to FIG. 24, in block 2404, the processor may record or collect samples of the acoustic environment of the hand-held mobile electronic device. The initiation of the recording of these samples may be based on determination by the processor, detected/received user inputs, and/or other identification of an initiation by the processor. Such other identifications may include receiving an identifier of the whistle or user to initiate a sampling/trial, determining the user has blown the whistle, a tapping of the whistle to the mobile device, the user pressing a button on the whistle, the retracting of the mouthpiece cover of the whistle, etc.

In some embodiments, the baseline acoustic context of block 2402 may be established before a whistle candidate (or collected/recorded samples) has begun. In some embodiments, the baseline acoustic context of block 2402 may be established after a whistle candidate, with an advantage that there is no need for a user to wait for baseline establishment to complete before starting a trial (or recording of acoustic samples). In some embodiments, the baseline acoustic context of block 2402 may be established continuously or between trials, thus requiring more resources but providing greater knowledge of baseline acoustic context. In some embodiments, the baseline acoustic context of block 2402 may be established during the whistle candidate, which may improve detection of frequency during the latter portion of a whistle candidate, and/or detection of cessation at the end of a whistle candidate. In some embodiments the recorded sample may require additional information from the user or replacement. For example, if a sample has too much background noise, the processor may prompt the user to replace such a sample and/or to provide further information about the sound source(s) of background noises.

In block 2406, the processor may analyze the samples to determine a frequency value for different acoustic signals included in the recorded samples. The determined frequency value may vary for each of the various acoustic signals within the samples.

In block 2408, the processor may use the recorded sample, the determined frequencies from block 2406, and/or the baseline acoustic context to determine whether various acoustic signals of the samples correspond to the whistle signal of a user performing an exhalation forcefully through the whistle. In some embodiments, the processor may then set aside the various acoustic signals that do correspond to the whistle signal and/or multiple whistle signals by comparing the frequency values and the baseline acoustic context to valid whistle signal frequency values. In some embodiments, these valid whistle signal frequency values may also be determined by an identification of the whistle, which may aid in establishing a baseline acoustic context through knowledge of the whistle features/capabilities.

In some embodiments, the acoustic signals of the recorded sample may initially be filtered through validation by the processor. The validations may compare the acoustic signals against parametric models. For example, the acoustic signal that is a whistle candidate might be accepted as valid if it is neither too short nor too long in duration; in this case, the parametric model includes two duration thresholds. In some embodiments, the validation may involve machine learning approaches, for instance, training an artificial neural network (ANN) on a large set of predetermined valid and invalid whistle candidates, then employing the trained network to assess the validity, or contribute to the assessment of validity, of new whistle candidates.

In block 2410, the processor may determine an expiratory airflow rate value of the user based on the frequency value of the acoustic signals. In some embodiments, the determination of the expiratory airflow rate values is in response to a determination that the acoustic signals are found to be corresponding to the whistle signals. The processor may set aside acoustic signals and frequency values to determine the user's expiratory airflow rate value based on the correlated/set aside acoustic signals because these set aside acoustic signals are known to have come from the whistle. Since there is a characteristic relationship between airflow rate and frequency of the whistle used in this method, the expiratory airflow rate value is then found based on the frequency value.

In block 2412, the processor may determine a respiratory parameter of the user based on the expiratory airflow rate value. Such parameters may include respiratory metrics such as PEFR and FEV1. In some embodiments, the respiratory parameter is stored to allow users to identify and track emergency conditions which then aid users in determining if a behavior may be affecting their respiratory health.

In block 2414, the processor may generate and render spirometric information such as respiratory parameters. In some embodiments, the processor may render the spirometric information in block 2414 via an electronic display of the mobile device. In some embodiments, in block 2414, the processor may render the spirometric information via the display of another device or component (for instance, a child conducts a peak flow measurement trial through a mobile game, and resulting spirometric information is sent to a parent for display via a web, mobile or email client, etc.). Thus, in some embodiments, the processor may render the generated spirometric information by transmitting the information to another device for display. The spirometric information may be generated based on the recorded samples, the determined frequency values, the determined expiratory airflow rate value and/or the determined respiratory parameter. Such spirometric information may provide concise graphical reports designed to facilitate quick, sound interpretation and effective medical treatment decisions. In some embodiments, the rendered spirometric information may include only information for key representations of select values/parameters that are determined to be important to the user (e.g., acute health issues). In other embodiments, the rendered spirometric information may be representative of holistic views of the user's respiratory condition. For example, the information may provide an easily understood visualization of the user's stored respiratory data to provide a more efficient understanding of potential behavioral patterns resulting in respiratory issues or information regarding acute respiratory issues. In one or more embodiments, the rendering of generated spirometric information may comprise the rendering of textual results (e.g. a peak flow reading presented as a number, the text "measurement successful" etc.). In one or more embodiments, the rendering of generated spirometric information may comprise presenting and/or altering graphical, auditory or haptic representations. For example, spirometric information (e.g. the magnitude of an expiratory airflow rate, the result of a peak flow measurement, an FEV1 value, the best of a series of peak flow measurements, the success/failure of a spirometric trial, whether or not a certain minimum/select/required number of spirometric trials has successfully been completed, whether or not a respiratory maneuver has been received by the mobile device, the approximate physical location of a spirometric measurement, etc.) may be presented through graphical visualizations, screen transitions, or as events situated within a game or story context that is presented by the mobile device.

Figure 25:
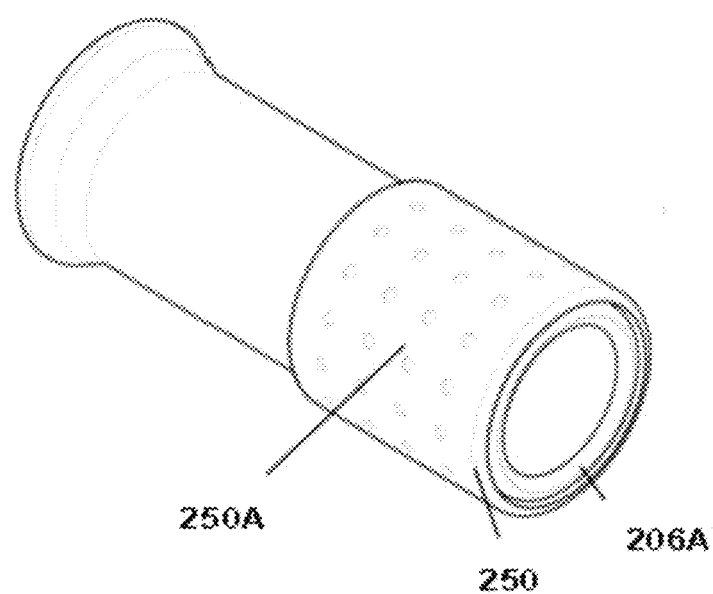
FIG. 25 shows a perspective view of a whistle with a mouthpiece cover in the covered position, in accordance with one or more embodiments.
Figure 26:
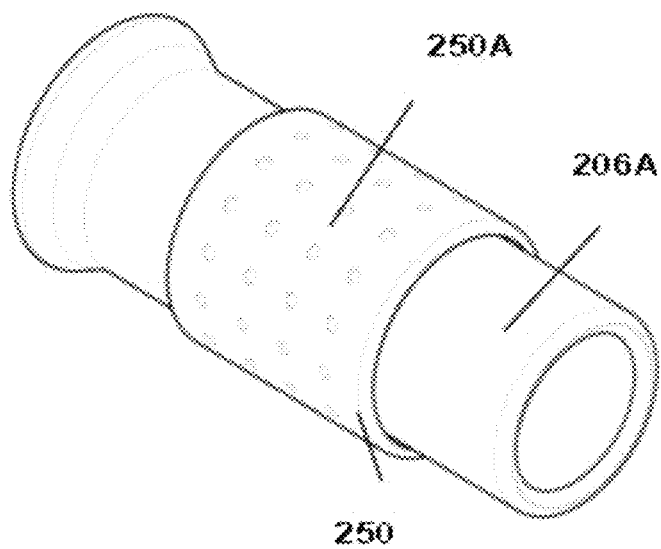
FIG. 26 shows a perspective view of a whistle with a mouthpiece cover in the retracted position, in accordance with one or more embodiments.

FIGS. 25 and 26 depict an embodiment of the whistle with a retractable mouthpiece cover 250 having a grip region 250A. In FIG. 25, the cover is extended, shielding mouthpiece 206A, while in FIG. 26, the cover is retracted, revealing mouthpiece 206A. When the cover is in its retracted state (in FIG. 26), mouthpiece 206A is accessible to a user's lips, while grip region 250A is positioned near the center of the whistle, enabling the user to hold the whistle manually in a balanced way; with an even weight distribution. In the whistle embodiment of FIGS. 25 and 26, the grip region is part of the mouthpiece cover; in some alternate whistle embodiments, the grip region is not part of the mouthpiece cover.

An integrated or detachable cap could cover the inlet region of some alternative variations of the whistle, to keep the inlet region clean. The action of capping the inlet could be designed so as to have the effect of wiping the inlet region clean. The outlet tube could be designed to "collapse" into the main tube when the whistle is not in use, in order to support a solution that is more compact.

According to one or more alternate embodiments of the invention, the external form of some variations of the whistle could resemble brass or woodwind musical instruments. For example, FIG. 11 depicts a user 102 blowing through horn-shaped whistle 104 towards a hand-held mobile electronic device 108, thereby recasting the task of routine peak flow measurement in terms of a potentially more enjoyable performance-like activity. The external form of some variations of the whistle could resemble characters, such as animals, with an advantage of making the whistle more inviting to children.

Alternative variations of the whistle could incorporate an identification code that, when submitted to a specified information service via a mobile device, returns a message validating a whistle's authenticity—to discourage counterfeiting, and thereby promote safety and reliability.

Just as the present invention's scope permits extensive variation of the whistle, it also permits extensive variation of the software process. Alternative variations of the software process could execute remotely, on a networked resource such as 105 with access to data from a mobile digital device, or in distributed fashion: partially on the mobile device, and partially over a network to which the mobile device connects.

Instead of monitoring for one and only one whistle sound (as outlined in FIG. 3), alternate implementations of the software process could monitor continually for the occurrence of whistle-sound candidates.

Alternate variations of the software process could be structured such that the recording of acoustic data occurs within an interrupt service routine or a separate software thread, rather than in a single main routine as FIG. 3 depicts.

Still other variations of the software process could provide the user with real-time interactive feedback while the user is blowing through the whistle.

Such alternate embodiments of the present invention's whistle and software process are offered as examples to illustrate breadth of scope; numerous substitutions and variations are possible without altering the basic premise of the invention.

From the previous description, a number of advantages of one or more embodiments of the present invention become evident:

Embodiments of the present invention enable leveraging the prodigious capabilities of prevalent hand-held mobile electronic devices equipped with acoustic input (such as mobile phones, personal digital assistants, mobile gaming platforms and tablets), while simultaneously simplifying requirements for—and reducing the cost of—a dedicated portable spirometry appliance.

Embodiments of the present invention render respiratory measurements digitally accessible to hand-held mobile electronic devices in a manner that is wireless, requires no electric power for signal transmission, and requires no wireless network configuration.

Whistle variations within more than an embodiment of the present invention intrinsically provide a user with real-time audio feedback that can serve to motivate the user to give his or her best effort, and thus indirectly contribute to the accuracy of spirometric measurements.

Whistle variations within one or more embodiments of the present invention are compact, highly portable, and contain no moving parts, electronics or batteries.

Because whistle variations within one or more embodiments of the present invention can be made from a single non-toxic material and contain no electronics, they can be manufactured using less energy and materials than alternate solutions, and can be recycled more easily.

Because whistle variations within one or more embodiments of the present invention can be manufactured from one non-toxic substance, they can be designed so as not to put toxic substances in close proximity with the entranceways of a user's respiratory and digestive tracts.

Whistle variations within one or more embodiments of the present invention can be designed to accommodate the frequency limitations of the microphones used in hand-held mobile electronic devices, as well as the bandwidth limitations of some of the wireless networks to which hand-held mobile electronic devices typically connect. As a result, airflow measurements can be derived by variations of the software process running locally on a hand-held mobile electronic device, as well as by variations of the software process running remotely, on another device connected to a network to which the hand-held mobile electronic device connects.

Whistle variations within one or more embodiments of the present invention structurally support a user's perception of blowing "straight through" the whistle, at a mobile device (or at representations on a display of a mobile device). By supporting this perception, the whistle variations assist a user to aim (and/or feel like they are aiming) at a hand-held mobile electronic device, permit the user to easily view interactive graphical feedback from the device, enable a user to feel more fully immersed in game/entertainment-like activities/environments presented by the device, and supports reliable communication between whistle and mobile digital device.

In contrast with some other spirometry solutions, embodiments of the present invention require no frequent calibration.

Since whistle variations within embodiments of the present invention contain no electronics, they can be cleaned with readily available aqueous solutions without risk of damage.

Accordingly, the reader will see that at least an embodiment of the present invention enables a more versatile expiratory measurement solution that is amenable to improved communication, visualization, reminding, annotation, correlation and/or motivation at less additional expense to a user, through leveraging the capabilities of ubiquitous hand-held mobile electronic devices with acoustic input and networking capabilities (such as mobile phones, personal digital assistants, mobile gaming platforms, and tablets), while also distilling the requirements of a dedicated spirometry device down to a simple whistle that requires no moving parts or electronics to communicate flow measurements.

An aspect of one or more embodiments is the ability to leverage certain advantageous aspects of hand-held mobile electronic devices, while simultaneously simplifying requirements for a dedicated portable spirometry device. These advantageous aspects include: Connectivity for interpersonal communications and data transfer; reminding through audio, vibrotactile and graphical means; information display through sophisticated graphical, audio and vibrotactile means; manual control through buttons and/or touch screens; interactive feedback for motivational, instructional, editorial, aesthetic and enjoyment purposes; data recording, processing and storage; juxtaposition, combination and correlation of information from local and remote sources; configurability and extensibility in terms of the ability to download and incorporate additional/alternate sounds, graphics, animations and software applications.

An additional aspect of one or more embodiments is that, through incorporation of the software process, the mobile digital device becomes more capable and more appropriately responsive in human contexts of use. Compared with other kinds of computer systems (such as desktops, servers, mainframes and appliances), a mobile digital device has particularly constrained computational, power and display resources, and its effective functioning is largely determined by of how well these limited resources are marshaled for a task that a given user wants to perform at a given time. In order for a mobile digital device to marshal its resources well for a particular task that a particular user wants to perform at a particular time, the mobile digital device must correctly sense and interpret what this task is that the user wants to perform. By discriminating between different types of acoustic input (i.e., valid measurement-related signals from a whistle vs. other signals) via the software process, the mobile digital device is able to respond more appropriately to a user's expressed intentions, and as a direct result, use its limited resources—memory, processing and power-more effectively for the task at hand. In a world where acoustic inputs to mobile digital devices are increasingly utilized for control purposes, and not simply the relaying of voice data, advances which enable a mobile digital device to discriminate effectively between acoustic contexts and orient resources appropriately are of considerable value. Thus, this aspect of one or more embodiments improves the functioning of a mobile digital device.

Another aspect of one or more embodiments is the enabling of a spirometry solution that does not require moving parts, electronics or batteries in order to accomplish measurement, beyond what is already contained within the mobile device. (Millions of people already own and carry such mobile devices for purposes independent of spirometry). Since one or more variations of the whistle contain no moving parts, electronics or batteries, they can be manufactured and recycled more easily, cheaply and reliably than existing spirometers using fewer material and energy resources, can be manufactured from just one material, and can be made from material(s) that do not place the entryway of a user's respiratory and digestive tracts in close proximity with toxins during use.

Still another aspect of one or more embodiments is to make use of a whistle that produces acoustic emissions with a frequency that varies with airflow rate, for the purpose of communicating airflow-based measurements to a physically separate hand-held mobile electronic device with a means of acoustic input, a device that is not primarily designed for spirometry.

Yet another aspect of one or more embodiments is that the whistle's design minimizes resistance to airflow. In order for a whistle to successfully be used for spirometric measurement, the whistle must not present undue resistance to a user's expiration. Otherwise, the whistle is restricting the respiratory system under measurement, and the results will be inaccurate. While it is generally true that measurement devices must minimally impact systems under measurement, the human respiratory system is particularly sensitive in this regard. Within the domain of human spirometric measurement, the measurement of peak expiratory flow is most affected by the resistance of a measurement device, since it is at peak expiratory flow that back-pressure resulting from the resistance of a measurement device tends to be highest. Since resistance to airflow is a key consideration, international standards for spirometric equipment such as ISO 23747:2007, ISO 23747:2009, and ISO 23747:2015 have explicitly provided limits for airflow resistance (e.g. 0.36 kPa/L/s).

An aspect of minimizing resistance to airflow that is employed by one or more embodiments is that the whistle includes an inlet passageway with a cross-sectional area large enough so as not to unduly restrict a user's expiratory airflow. Airflow resistance through an open passageway is proportional to 1/radius$^4$ (according to Hagen—Poiseuille's law) so even a small increase in the cross-sectional area of the whistle's inlet passageway (relative to some existing whistle designs) results in a large reduction in airflow resistance, thereby improving or enabling measurement of human peak expiratory flow.

A further aspect of one or more embodiments is that the mobile device comprises the physical elements necessary to support a whistle-based flow measurement trial. One or more embodiments comprise an acoustic input capability (such as an integrated microphone, an attached microphone, a wirelessly connected microphone, or an audio transceiver). One or more embodiments comprise a local memory storage capability (such as registers, RAM, ROM, EEPROM, and FLASH). One or more embodiments comprise a local data processing capability (such as a microcontroller, microprocessor, co-processor, GPU or ASIC). One or more embodiments comprise at least one display. The display may be graphical, auditory or haptic. The display is capable of presenting representations to the user. In the case of a graphical display, such representations may include, for instance, numbers, letters, words, bar graphs, regions of color, lines, or animated characters. In the case of an auditory display, such representations may include tones, sound effects or synthesized or spoken words. One or more embodiments comprise at least one input device, such as a mechanical keypad, virtual keypad, resistive touch-screen, capacitive touch-screen or wireless keyboard. One or more embodiments further comprise a wireless networking capability (such as a Bluetooth, WiFi, or a cellular networking capability). One or more embodiments further comprise a capability for sensing or obtaining physical location (such as a GPS module, a means of sensing Bluetooth beacons, or a network-based location service). One or more embodiments further comprise a means of obtaining atmospheric pressure. This means could be direct, in the form of an integrated pressure sensor, or indirect, comprised of a location-obtaining capability used in conjunction with local or remote data that enables determining pressure from location (for example, a wireless location service reports latitude and longitude, which are used to derive elevation from map data, which, in turn, is used to produce an estimate of local atmospheric pressure).

An additional aspect of one or more embodiments is that the mobile digital device can communicate with a networked data resource. This networked data resource has a storage capability. In one or more embodiments, the resource has a processing capability. The networked data resource may be entirely centralized, entirely distributed, or partially centralized and partially distributed. In one or more embodiments, the networked data resource has multiple sources of input. For instance, it receives flow measurement related data from mobile digital devices, pollen count from an online service, and current time from a remote time-server. In one or more embodiments, the networked data resource can aggregate and/or correlate data comprising flow measurements, to support the revelation of trends across a population, a region, or other axes of inquiry.

An additional aspect of one or more embodiments is that the whistle is designed to produce a clear acoustic signal, so as to support reliable communication between whistle and mobile digital device. Without a clear signal, background noise present in real-world mobile usage environments will cause false readings that may ultimately jeopardize human health. If the structure of a whistle discourages laminar (i.e. uniform, non-turbulent) flow at certain stages, or presents through-flowing airflow with surface discontinuities such as rough walls, angular transitions, holes, recesses or exposed screw heads, turbulence is introduced that will ultimately compromise the clarity of any acoustic signal emitted, while adding undesirable resistance to airflow. In at least an embodiment, resistance to airflow is minimized and acoustic signal clarity is increased through use of at least one substantially smooth and continuous airflow passageway. In at least an embodiment, resistance to airflow is minimized and acoustic clarity increased through use of at least one airflow passageway that does not place angular transition bends in the path of incoming airflow. In at least an embodiment, the need for exposed screw heads, exposed screw drive recesses or holes within the walls of airflow passageways is eliminated, with advantages that resistance to airflow is minimized and acoustic signal clarity is increased. In at least an embodiment, the whistle inlet passageway is sub-divided, with an advantage that total airflow through the inlet passageway is more laminar in aggregate.

An additional aspect of one or more embodiments is that the whistle's design balances the potentially competing concerns of: a) minimizing resistance to flow (so as not to restrict a user's peak expiratory airflow) and b) maximizing the clarity of a sufficiently loud emitted acoustic signal (so as to support reliable communication between whistle and mobile digital device).

Another aspect of one or more embodiments is that the whistle's structure discourages or prevents a human user from holding the microphone of a mobile digital device so close to the whistle's outlet that signal communication between whistle and mobile device is compromised by 1) "wind" from airflow exiting the whistle, or 2) the amplitude "clipping" that can occur when a mobile device must process a signal containing an amplitude that is too high to be represented by the mobile device's hardware or software. In both cases, signal reception suffers, and the quality of the spirometric system is reduced. In at least an embodiment, the whistle includes a barrier around the outlet with advantages including: a) preventing the user from holding the microphone of the mobile device unduly close to the outlet of the whistle, and b) preventing the user from touching or blocking an outlet of the whistle while the whistle is in use. In at least an embodiment, the whistle includes at least one outlet, positioned such that a user blowing through the whistle cannot easily view the screen of the mobile device while holding the microphone of the mobile device unduly close to the outlet of the whistle.

An additional aspect of at least an embodiment is that the whistle produces acoustic emissions from multiple outlets— with several advantages. A whistle with multiple outlets may a) reduce over-all resistance to expiratory airflow, b) extend the range of airflow rates for which acoustic emissions are both audible and non-shrill, c) increase the amplitude of an emitted acoustic signal at low expiratory airflow rates, d) result in acoustic emissions occurring closer to each of a user's two ears, where they can be perceived more loudly, in "stereo", and e) decrease the directionality of acoustic emissions, thereby enabling acoustic signal transmission to be more robust with respect to relative orientation between whistle and mobile digital device. In some embodiments, the multiple outlets are of different sizes, thus altering the sound producing characteristics of the whistle. In one or more embodiments, the whistle comprises a pair of airflow guides that direct a user's expiratory airflow into a pair of counter-rotating vortices that exit the whistle through a pair of substantially parallel outlets, with an advantage that counter-rotating vortices interfere with each other less than vortices that rotate in the same direction—thus supporting strong acoustic emissions that are clear and stable.

Another aspect of one or more embodiments is that the whistle accommodates a seal with a user's lips that is air-tight, comfortable and easy for the user to maintain during forced exhalation. In one or more embodiments, the whistle's design enables the whistle to be held entirely by the user's lips during forced exhalation. If the seal is not airtight, measurement accuracy will be compromised. If the seal is not comfortable, adherence to a measurement regime may falter. If the seal is not easy for the user to maintain, the user must expend their effort and concentration on maintaining the seal, and measurement accuracy will be compromised. In order to accommodate an airtight seal, the whistle of one or more embodiments includes an inlet/mouthpiece with an external surface that is substantially smooth and continuous, with no sharp-angled bends. In at least an embodiment, the external surface of the whistle's inlet/mouthpiece has an oblong cross-section. In at least an embodiment, the cross-sectional dimensions of the exterior surface of the whistle's inlet/mouthpiece are non-increasing, or decreasing in the direction of exhalation, with an advantage of assisting a user to maintain an airtight seal between the moist portion of the lips and the whistle, and to hold the whistle with the lips during forced exhalation. (If an inlet were instead to widen in the direction of through-flowing airflow—as is true for some pre-existing whistle designs never meant for spirometric measurement—pressure exerted by a user's lips translates into forces pushing the whistle out and away from a user, making the whistle harder to hold during forced exhalation).

Another aspect of one or more embodiments is that the whistle not only reduces manufacturing cost and complexity by not requiring any electronics or moving parts for signal emission, but also reduces manufacturing cost and complexity by minimizing the number of parts required to assemble the whistle. In at least an embodiment, the whistle is composed of just two or three parts, each part realizable through a straight-pull injection molding process. In at least an embodiment, at least one of the whistle's parts is realizable using a two-shot injection molding process, so as to enable a soft external grip for the user while ensuring a smooth passageway for internal airflow. Accordingly, in some embodiments, the mouthpiece and inlet are features of the same component or part, while in other embodiments, the mouthpiece is its own part. In some embodiments, the mouthpiece is detachable, to support hygienic shared use of a common whistle.

Yet another aspect of one or more embodiments is that the whistle comprises a grip region, where a user may manually hold the whistle while in use. In one or more embodiments, the grip region is substantially softer to the touch than other features of the whistle, with an advantage of increasing user comfort while the whistle is in use, while not lowering the quality of the whistle. In one or more embodiments, the grip region presents greater surface sliding friction to a human hand than other features of the whistle which are not meant to be held by hand, with an advantage of reducing the chances that the whistle will be dropped, or will change position in a user's hand while in use. Surface sliding friction can be achieved through choice of texture, choice of material, or both. In one or more embodiments, the grip region is visually distinct from other aspects of the whistle (for example, of a different color, brightness, reflectivity, and/or texture), with an advantage of communicating to a user where to hold the whistle. In one or more embodiments, the grip region has a surface texture that differs substantially from the surface finish of other aspects of the whistle, with advantages of communicating to a user where to hold the whistle, and potentially increasing the perceived value of the whistle (through simulating the texture of comparatively expensive materials such as leather or turtle-shell).

A still further aspect of one or more embodiments of the whistle is that the surface finish of the whistle's mouthpiece region is substantially smooth, with an advantage of facilitating cleaning. In one or more embodiments, the whistle's mouthpiece region is of a harder material than the whistle's grip region, with advantages of a) clarifying the relative function of each aspect of the whistle, b) reducing the chances that the mouthpiece region will become scratched, c) reducing the chances that a user will experience unpleasant roughness with their lips, as the result of the mouthpiece region becoming scratched.

An additional aspect of one or more embodiments is that the whistle produces an acceptable and receivable audible acoustic signal in response to a full range of human expiratory airflow rates. The full range of human expiratory airflow rates can be surprisingly broad; the international standard for peak expiratory flow meters, EN ISO 23747: 2007, recommends supporting a range of peak flow rates extending from 60 L/min on the low end, to more than 800 L/min on the high end. An acceptable and receivable audible acoustic signal is not too low in amplitude or subsonic at low flow rates, and not too loud, too shrill, or ultrasonic at high flow rates.

An aspects of one or more embodiments is that particular whistle and/or process embodiments balances tradeoffs so as to best accommodate needs of particular user groups, such as children, adults, athletes, or patients with severe late-onset asthma. For example embodiments of the invention may comprise a "high flow range" whistle designed to meet the needs of adults or athletes, as well as a "low flow range" whistle designed to meet the needs of children.

According to yet another aspect of one or more embodiments, respiratory measurements are made accessible to the hand-held mobile electronic device through a means that is wireless, does not require initial configuration of a wireless network, and does not require any energy additional to the energy already contained within a user's forced exhalation.

Further aspects of one or more embodiments are that the whistle requires no frequent calibration, and can easily be cleaned and sterilized using aqueous solutions (such as detergent and water) without risk of damage.

According to a still further aspect of one or more embodiments, the whistle itself provides perceptible real-time feedback to a user that varies with a user's expiratory airflow rate. This feedback includes audio feedback perceivable by a user's ears, and may additionally include tactile feedback, sense-able by a user's skin; specifically wind and/or heat originating from a user's expiratory airflow. Measurement of forced expiration is inherently effort-dependent, and providing perceptible, real-time feedback is an effective way to reward effort. In addition to rewarding user effort, perceptible real-time feedback can also facilitate identifying and discounting invalid measurement trials.

According to an additional aspect of one or more embodiments, the range of frequencies that the whistle emits in response to peak expiratory airflow rates can fit comfortably within a frequency range suitable for both a) the microphones used in hand-held mobile electronic devices, as well as b) one or more of the wireless networks to which such hand-held mobile electronic devices can typically connect.

The whistle's ability to function within a frequency range defined by these two requirements supports derivation of respiratory measurements by variations of the software process running locally on the hand-held mobile electronic device, as well as by variations of the software process running remotely on another device that connects to a network to which the hand-held mobile electronic device can connect.

According to an aspect of at least an embodiment, emissions of the whistle in response to through-flowing expiratory airflow are ultrasonic, with advantages that a) the whistle will not disrupt other humans, and b) the whistle can be used in environments characterized by extensive noise within the audible frequency range.

According to yet another aspect of one or more embodiments, the form of the whistle aligns the prevailing direction of incoming airflow with the prevailing actual or perceived direction of outgoing airflow. Such alignment can assist a user to aim (and feel like they are aiming) at the hand-held mobile electronic device, can assist the user to easily view interactive graphical feedback from the device, and can support reliable communication between the whistle and the mobile digital device.

An additional aspect of one or more embodiments is that the whistle includes a "false" outlet (for example, a horn-shaped form, which may or may not be placed around a true outlet), with advantages including a) supporting the illusion that a user can blow "straight through" the whistle, at the mobile device, and b) serving as a barrier to prevent a user from holding the microphone of a mobile device too close to a true outlet of the whistle. In some embodiments, a false outlet may be axially aligned with a true inlet, to support a user's perception of blowing straight through the whistle.

Another aspect of one or more embodiments is that the whistle includes an inlet that is small enough to be held by human lips, while also including an outlet (or an opening, or partial opening that a user may perceive to be an outlet) that is too large to be held by human lips. This aspect has an advantage of clarifying for a user, which end of the whistle to blow into.

An additional aspect of one or more embodiments is the whistle includes an outlet with a prevailing direction of airflow that is at an angle of no more than 90 degrees from the prevailing direction of airflow through the whistle's inlet. This aspect enables a user to receive continuous tactile feedback during forced exhalation, on the face or chest, in the form of wind and heat from expiration. In at least an embodiment, the whistle includes an outlet with a prevailing direction of airflow that is substantially perpendicular (i.e., ±20°) to the prevailing direction of airflow through the whistle's inlet. Such an orientation can simplify manufacture of the whistle. In at least an embodiment, the whistle includes multiple outlets with a prevailing direction of airflow that is substantially perpendicular to the prevailing direction of airflow through the whistle's inlet.

In at least an embodiment, the whistle includes a central cavity with a wall that follows a circular contour, with the advantage that such a whistle can be less expensive to design and manufacture. In at least an embodiment, the whistle includes a central cavity with a wall that follows a contour with a variable radius, such as a continuously variable radius. In at least an embodiment, the whistle includes a central cavity with a wall that follows a contour based on a logarithmic spiral. A whistle with a central cavity with a wall that follows a variable radius (or has a spiral contour) can offer advantages with respect to reduced airflow resistance and reduced turbulence.

In at least an embodiment, the whistle includes an airflow guide that translates the direction of airflow into a swirling vortex with a central axis that is substantially parallel (i.e., ±20°) with the prevailing direction of incoming airflow which may have an advantage that the whistle inlet and outlet can be axially aligned to support a user's perception of aiming/blowing at a mobile device, or representations displayed by a display of the mobile device. In at least an embodiment, the whistle includes structure that directs incoming airflow into a swirling vortex with a central axis that is substantially perpendicular to the direction of incoming airflow, which may have an advantage that the vortex can exit one or more outlets that are positioned close to the user's ears.

According to an additional aspect of one or more embodiments, the external form of the whistle supports a metaphor unrelated to spirometric peak flow measurement, a metaphor that contributes to ease of use of the whistle, encourages adherence to a peak flow measurement regimen, encourages a user to give their best effort, or invites a user to enjoy the task of performing a peak flow measurement as though enjoying another activity. In at least an embodiment, the external form of the whistle resembles a horn. In at least an embodiment, the external form of the whistle resembles a referee's whistle. In at least an embodiment, the external form of the whistle resembles an animal capable of loud or otherwise surprising perceptible emissions (e.g., a baby bird in a nest calling for food, a dolphin emitting its signature whistle, or a spitting cobra projecting venom). In at least an embodiment, the external form of the whistle resembles a cloud, capable of causing wind to blow. In at least an embodiment, the external form of the whistle represents a party whistle.

According to an additional aspect of one or more embodiments, representations perceptible from the display of the mobile device support a metaphor unrelated to spirometric peak flow measurement, a metaphor that contributes to ease of use of the peak flow measurement system as a whole, encourages adherence to a peak flow measurement regimen, encourages a user to give their best effort, or invites a user to enjoy the task of performing a peak flow measurement as though enjoying another activity. In at least an embodiment, the display of the mobile device depicts a pinwheel or windmill that starts to turn in response to forced exhalation through the whistle. In at least an embodiment, the display of the mobile device depicts a person or animal that becomes startled by the sound of a whistle. In at least an embodiment, the display of the mobile device depicts a whale in the ocean that discharges visibly through its blowhole in response to the sound emitted by the whistle. In at least an embodiment, the display of the mobile device depicts a cake with candles whose flames extinguish in response to the sound emitted by the whistle. In at least an embodiment, the display of the mobile device depicts a burning building, whose flames are extinguished in response to the sound emitted by the whistle during forced exhalation.

According to yet another aspect of one or more embodiments, the external form of the whistle, works in conjunction with representations perceptible from the display of the mobile digital device to support a metaphor unrelated to spirometric peak flow measurement that contributes to ease of use, encourages adherence to a peak flow measurement regimen, encourages a user to give their best effort, or invites a user to enjoy the task of performing a peak flow measurement as though enjoying another activity. In at least an embodiment, the external form of the whistle resembles a bugle, while the mobile device displays a sleeping soldier. In at least an embodiment, the external form of the whistle resembles a cloud, while the mobile device displays a dandelion, whose seeds blow away in the "wind" a user can imagine emanating from the cloud (as a result of blowing through the cloud-whistle).

According to an additional aspect of one or more embodiments, the invention enables a spirometry system that combines real-time auditory feedback from a whistle during expiration with feedback of at least one other sensory mode (e.g., visual feedback, tactile feedback) from a mobile digital device, where at least some of the feedback from the mobile device occurs at the end of, or following expiration. The advantages of combining multiple types of perceptual feedback from multiple sensory channels are well known in the arts and entertainment (e.g., promoting immersion/engagement), as well as in education (e.g., promoting reinforcement/retention). Combining multiple types of perceptual feedback from multiple sensory channels can have similar benefits in spirometry—enabling peak flow measurement regimens that are more enjoyable, adhered to more regularly, and conducted with skill more quickly.

According to a further aspect of one or more embodiments, the mobile digital device provides at least some feedback to the user in real-time during a user's forced exhalation through the whistle. ("Real-time feedback" from the mobile digital device is understood to encompass near real-time feedback, since mobile digital devices cannot process signals instantaneously). Real-time feedback communicates a tight coupling between perceived cause and perceived effect, and so can strengthen a user's sense of immersion, engagement and agency.

According to another aspect of one or more embodiments, the external form of the whistle comprises substantially rounded edges, with an advantage that the whistle can more easily be removed from or inserted into typical containers on a user's person (such as pockets, backpacks or handbags), without catching, scratching other items, cutting a user or causing discomfort while in use.

According to another aspect of one or more embodiments, the whistle may include (or have attributed to it) a static or dynamic identifier, which can be communicated to the computational system that the whistle is in communication with, thereby enabling the system to access information intrinsic to (or associated with) the whistle: attributes such as the whistle's name, size, recommended measurement range, type, version, manufacturer, vendor, distributor, characteristic relationship between airflow rate and frequency, purchaser, owner, user, user id or user details (including information such as flow measurement-related data or mobile app settings or configuration). In one or more embodiments, this identifier may be a visual indicator and/or human readable, and may be entered, by the user, into the system the whistle is in communication with (e.g. via a physical or virtual keypad, or a menu). Examples of visual indicators or human-readable identifiers, or representations of identifiers (which may all herein be referred to as identifiers), include: names, textual descriptions, symbols, logos, logotypes, colors, numeric codes, alphanumeric codes, and other symbolic or pictorial codes, and pictures (e.g. of a "small", "medium" or "large" whistle; a "child" or "adult" whistle; or "low range" or "high range whistle", etc.). As these examples indicate, the term "human readable" herein is broadly synonymous with "human identifiable/categorizeable", and not to be construed as limited solely to the literal reading of characters or words. In one or more embodiments, a human-readable identifier or a representation of an identifier may be entered manually, via a physical or virtual keypad, or via a graphical or textual menu. In one or more embodiments, the identifier is machine-readable by the system the whistle is in communication with, and can be read automatically—either explicitly, through the user intentionally presenting the whistle for identification, or else implicitly, through the natural course of the user using the whistle with the system that the whistle is in communication with (e.g. a feature of the sound produced by the whistle, such as a frequency, may be identified by the mobile device). In one or more embodiments, the whistle includes both a human readable identifier and a machine-readable identifier. In one or more embodiments, there are multiple forms of machine-readable and or human-readable identifiers, with advantages including redundancy and broadened compatibility with, for instance, different mobile phones with different sensing capabilities. In one or more embodiments, identification is accomplished through a printed, human-legible code. In one or more embodiments, identification is accomplished through a bar code, QR code, or other form of machine-readable code on the whistle being captured by the integrated camera of a mobile digital device and interpreted by image processing routines on the device. In one or more embodiments, identification of the whistle is accomplished through an RFID or NFC tag affixed to or embedded in the whistle communicating via near field (magnetic) or far field (radio) communication with an NFC or RFID reading capability of the mobile digital device. In one or more embodiments, a machine-readable identification means such as an RFID or NFC tag may store and communicate data to the mobile digital device in addition to or instead of an identifier (e.g. such as data stored in a memory of the tag, representing the whistle's characteristic relationship between flow rate and frequency, a user's settings, cryptographic settings such as hash values, etc.) In one or more embodiments, identification is accomplished through capacitive coupling. As some of the previous illustrative examples indicate, an identifier of the whistle may be analog or digital.

For simplicity, embodiments of machine-readable identifiers or codes such as bar codes, QR codes, NFC tags, RFID tags, and tags that communicate through capacitive coupling may be herein referred to as "automatic identification tags", and means of reading (and/or writing) content of machine-readable tags may be referred to as "automatic identification tag transceiver." The term "tag" herein may refer to an affixed, stickered, printed, integrated or embedded label or device. The term "identifier" herein may refer to a human-readable or machine-readable means of identifying or specifying a whistle or type of whistle.

As mentioned above, in some embodiments, identification may be accomplished through capacitive coupling. One example of a capacitive coupling approach is as follows: A surface (or subsurface) layer of the whistle includes electrically conductive or electrically resistive regions, spatially distributed along one or two Cartesian or polar dimensions or axes, such that the spacing and/or size of the regions encodes information (e.g., an identification code). When the whistle is held with a user's hand sufficiently close to, or touching, the touchscreen of a mobile device, the mobile device senses the locations and/or sizes of the regions capacitively (similar to the manner that multiple simultaneous finger touches on different locations of a touchscreen can be sensed), and uses the locations and/or sizes of the regions to decode the encoded information (e.g., as an identifying tag/code or to obtain the identification code). In such an approach, the user's hand may be capacitively, conductively, and/or resistively coupled with one or more of the regions to provide an identification.

In one or more embodiments, identifiers may also include names or images or other identifiers ascribed to a whistle, that are not a part of the whistle itself. Such identification may include associated devices, associated identifying tags/codes, associated packaging, printed product information, or other identifier described above. For example, an associated device may provide identification in place of the whistle, or in other examples, an identifier may include a pattern of tapping the whistle to a touchscreen (e.g., a pattern using binary code as an identifier). In one or more embodiments the identifiers include whistle device characteristics that may differentiate whistles from one another or between models. For example, a whistle may include handholds on the body specifically designed to a certain user in a certain shape/mold, a whistle mouthpiece may include key-like formations, or a user fingerprint engraved in the side of the whistle.

In one or more embodiments, identifiers are received by the mobile device directly, as a result of a machine-readable code. In one or more embodiments, identifiers are received by the mobile device through user input means such as a keypad or touchscreen (e.g. manual entry of a serial number from a whistle, manual entry of a whistle's name or type printed on the whistle's packaging, manual selection of a menu item or picture of a "low range" or "high range" whistle, rendered on a touchscreen display of the mobile digital device, etc.).

Advantages of including a human or machine readable static or dynamic identifier include discouragement of counterfeiting and its associated health risks and business risks (since an identifier furnishes a means of identifying a whistle or whistle type and verifying its provenance), support for automated sign-in and personalization of the system (since the whistle can act as a token or a key that stands for a given user), and support for different types or versions of whistles (since essential information about a whistle—such as its characteristic relationship between airflow rate and frequency—can be determined based on the whistle's identifier).

In one or more embodiments, a human-readable or machine-readable static or dynamic identifier may enable validation of a whistle, validation of a user, validation of the combination of a whistle and a mobile device, and/or validation of a combination of a whistle and software instance running on a mobile device. In one or more embodiments, a human-readable or machine-readable static or dynamic identifier may enable the mobile digital device or system to determine which among a set of pre-determined correlations between frequency and airflow-rate to employ when interpreting acoustic information received from a given whistle or type of whistle.

In one or more embodiments, identifiers used for validations may be added to an information structure (e.g. list, array, etc.), and/or stored in the memory of the mobile digital device, with an advantage of facilitating retrieval and comparison.

An aspect of one or more embodiments is that the mobile device has a means of user input, for entering a human-readable identifier that may be printed on, molded into or affixed to the whistle, whereby the whistle's identifier may be made accessible to the software process. Examples of such means of entry include: a virtual or mechanical keypad, a touch-screen or a voice entry system. If a whistle's identifier can be made accessible to the software process via human input, use of counterfeit whistles can be restricted even in situations where a mobile digital device cannot automatically identify the whistle or whistle type through automated means. In one or more embodiments the identification of the whistle may result in initiation of a trial.

In one or more embodiments, identifiers may be representations corresponding to one or more whistles or whistle types that may be presented on the display of the mobile digital device, with advantages of: a) facilitating selection of a whistle that has been used (or will be used) to perform a measurement trial, and b) assisting a user to verify the validity of a trial result—and potentially alter a displayed measurement, or representation based on a displayed measurement, such that it corresponds to the whistle used during the trial.

In one or more embodiments, a given whistle can be used with only a limited number of mobile devices, as determined by software running on or in communication with these mobile devices, based on the given whistle's identifier. In one or more embodiments, a given mobile device can be used with only a limited number of whistles, as determined by software running in least in part on the mobile device based on the whistles' identifiers. In one or more embodiments, usage of the whistle in conjunction with the software system is limited to a certain set of users, based on the combination of whistle identifier and information about the user that the software system has access to, such login credentials or location. These aspects can deter counterfeiting in circumstances where whistle identifiers themselves can be easily copied.

Advantages of the present invention in relation to counterfeit deterrence are of particular importance. Although some embodiments of the whistle are mechanically simple (and thus may be easy to forge to some approximation of accuracy), they function as the primary data source upon which safety-critical, life-or-death decisions are made. If a counterfeit whistle with unverified acoustic properties were to be successfully used in place of a genuine whistle, the resulting expiratory airflow measurements could be inaccurate in ways that could place a user's life in jeopardy.

According to one or more embodiments, the whistle can be authenticated by the system through cryptographic authentication. In one such authentication scheme, the software system maintains a cryptographic "hash chain": an ordered list of numbers ("hashes"), such that each number in the list can be easily computed as a function of the previous number (using a "hash function" or "one-way function"), but going "backwards"—attempting to derive the previous number from the current number—is computationally prohibitive or unlikely. In this particular scheme, the whistle comes provisioned with an initial hash value (placed within the readable/writable memory of an RFID tag, for example). Each time the user signals their intention to conduct a trial (by tapping the screen of a mobile phone with the whistle, for instance), the system reads the whistle's current hash value. If the current value is determined to be valid, the system updates the current value to be the next value in the chain (e.g. by writing the value to the readable/writeable memory of the RFID tag, etc.), and permits the trial continue. If the current value is determined to be invalid, the trial is not permitted to continue. This is merely one example of a cryptographic authentication scheme that enables a whistle, or by extension, user, to be validated by the system. Other cryptographic authentication schemes are possible; for instance, the system could compute values of a hash chain on the fly, rather than keep an entire hash chain in memory. The system could alternately rely on a chain of pseudo-random numbers, or other hard-to-guess sequence, instead of a sequence generated by a particular one-way function. In some implementations, the system could make use of multiple one-way functions, or a family of one-way functions, in conjunction with other pieces of data such as an authentication sequence count (a number that increments with each successful authentication), a numeric identifier, or a pseudo-random number. Cryptographic authentication has the advantage of vastly decreasing the chances that a counterfeit whistle could be used with a legitimate system—and vice versa.

In one or more embodiments, the computational system that the whistle is in acoustic communication with presents a user with an optional (or mandatory) choice to specify which whistle (or type of whistle) is used (or assumed to be used)—before, during and/or after a measurement trial. Such a choice may be presented through textual, graphical or auditory means. In some embodiments, when results of a measurement trial are presented, they are presented in conjunction with a representation of the set of whistles, whistle types, whistle models or whistle versions for which the system can (or is authorized to) derive valid flow measurement results. In some embodiments, this representation could take the form of a drop-down menu. In some embodiments, this representation could take the form of a button, showing a currently selected whistle-type, that when pressed, reveals a menu displaying alternate possible whistle types that can be selected, enabling a user to choose the whistle type corresponding to a given measurement trial. In some such embodiments, if the whistle type that the system presents as selected is different from the whistle (or whistle type) that the user has used or will use, the user can correct the system's presented selection, potentially also correcting displayed and/or recorded trial results. In some embodiments, the mobile device presents a peak flow measurement in conjunction with a representation of a whistle (or type or version of whistle) that cannot be changed by the user; in some situations the mobile device can automatically detect the whistle type, and presenting the user with the ability to select an alternate whistle could invite user-error and/or invalid measurements.

The term "whistle type" may be used herein to succinctly refer to whistle makes, models or versions, in contexts where there are potentially multiple whistle makes, models or versions which may be selected, or must be discriminated between.

In one or more embodiments, the computational system may, through use of a digital camera sensor on or attached to the mobile device, attempt to identify the type of whistle that is used before, during or after a trial, based on visible aspects of the whistle itself, related to its shape, color, reflectivity, relative placement/orientation of detectible features, or manner held in-hand by a user. In one concrete example, different types/models of whistles are color-coded (or marked with one or more color-coded patches). During use of the whistle and mobile device, the color-based indicator(s) of the whistle are sensed by computer vision techniques, and determined to correspond to a particular type of whistle by the computational resources available to the mobile digital device.

In one or more embodiments, multiple approaches are used in concert to identify a whistle or type of whistle. For instance, the reading of a bar code could be used in conjunction with the reading of an RFID tag, or an RFID tag could be used in conjunction with color-based visual markers to establish the identity of the whistle. The use of multiple approaches may increase the accuracy/reliability of recognition.

In one or more embodiments, the mobile device includes an indirect or direct means of obtaining barometric pressure, and may employ such means to arrive at or refine airflow-related measurements. For certain types of whistles, emitted acoustic frequency may not solely be a function of through-flowing airflow rate, it may also be a function of the atmospheric pressure at the location of the whistle. If not only airflow rate, but also atmospheric pressure are known, it is possible to derive more accurate measurements, and thereby provide better decision support for respiratory health. In some embodiments, the mobile device directly incorporates an air pressure or altitude sensor. In one or more embodiments, the mobile device incorporates a means of obtaining location, (such as a GPS module, an ability to communicate with fixed Bluetooth "beacons", or access to a wireless location service), and relies on this means of obtaining location in conjunction with data, local to the device or external, mapping location to air pressure (for example, cartographic elevation data, or data associating Bluetooth beacon locations with the floors of a skyscraper) in order to obtain a measurement or estimate of atmospheric pressure. In one or more embodiments, multiple means of obtaining atmospheric pressure may be employed in combination, for redundancy, improved accuracy, and/or precision.

According to one or more embodiments, the software process accommodates shared usage of a mobile digital device by presenting user-specific representations, information and/or feedback on the display of the mobile digital device. In some embodiments, the software process causes the mobile digital device to display a representation of the user's identity. In one or more embodiments, the user can log in, or select from among a list of representations of user identity. In one or more embodiments, a user's whistle, equipped with information readable from the mobile digital device, functions as a user's key or token for login, verification or customization.

According to one or more embodiments, the software process records the location of the mobile device during a trial, with an advantage of supporting creation of data that can be used to understand relationships between location and respiratory health for a population. Such information is of utility in public health, environmental justice, and pharmaceutical distribution.

It is an aspect of one or more embodiments that the computational system in communication with the whistle determines whether or not a received sound corresponds to the sound from the whistle made in response to a user performing a forced exhalation. In some embodiments, the computational system instructs the user based on acoustic data received. For example, if received acoustic data remains below a certain amplitude threshold, the mobile digital device provides an instruction to blow more forcefully, or to blow more closely to the microphone. (NOTE: The term "acoustic data" herein is not synonymous with "analog data"; if the context is digital, "acoustic data" refers to a digital representation of acoustic data). In some embodiments, if a received sound meets some but not all of the requirements for a valid whistle sound, the mobile digital device provides an instruction to try again. In some embodiments, if features of the received acoustic signal suggest a noisy background environment, the mobile digital device instructs a user to perform trials in a quieter location. Through providing instruction dynamically, in response to contextual information available from a received acoustic signal, such embodiments can aid a user to actively problem-solve, and perform expiratory flow measurement with greater skill, more reliable results, and a quicker, easier learning curve.

According to one or more embodiments, the computational system handles trial results in a "best of three" fashion: acoustic signals corresponding to three forced exhalations through the whistle are processed to yield three measurements, and the largest measurement retained and communicated. In some embodiments, the mobile device may request an additional trial in the event that a previous trial has not produced a valid measurement. In some embodiments, the final result for a set of trials conducted during one session of use is a function of measurements made for some or all of the trials in the set, such as the mean value, or the median value.

In accordance with one or more embodiments, an aspect of the software process is that it interprets whether or not a user has elected to begin performance of a measurement trial. In various embodiments of the software process, a user's election to begin a trial could be communicated by, for instance, pressing a virtual or physical button, performing a swipe gesture on the touch-screen of the mobile device, beginning a forced exhalation, uttering a command, tapping the screen of the mobile device with the whistle, bringing the whistle into close proximity to the mobile device, or launching an application from the mobile device. In various embodiments, interpreting whether or not a user has elected to begin a measurement trial could take place before trial has begun, with advantages of simplifying implementation, or while a forced exhalation is already underway, with an advantage of reducing the number of steps a user must perform in order to successfully complete a trial.

The ability to accurately interpret whether or not a user has elected to begin a trial is of considerable importance. If the software process cannot accurately and reliably determine whether a user wishes to start a trial, the user may experience disappointment, perceive a loss of control, and lose trust in the system. As a result, adherence to a spirometric measurement regime may deteriorate.

According to one or more embodiments, an aspect of the software process is to successfully register at least one temporal boundary for acoustic data processing. Examples of temporal boundaries include: a) a point in time before the onset of a whistle candidate, b) a point in time substantially corresponding to the onset or cessation of a whistle candidate, c) a point of time within a whistle candidate, d) a point in time after the cessation of a whistle candidate, e) a point in time corresponding to the start of an acoustic input data "frame": a regularly-sized consecutive sequence of input samples processed together. The start of an acoustic input data frame may account for overlap between consecutive frames. (Overlap is often desirable in circumstances requiring a large frame size together with a low inter-frame duration). The capability to reliably register temporal boundaries supports accurate timing of duration, detection of salient features within a candidate whistle recording, and simplifies subsequent processing.

Registering temporal boundaries before the onset and after the cessation of a whistle candidate has an advantage of ensuring that the whistle candidate can be evaluated with respect to the temporal context in which the whistle candidate occurs. Registering temporal boundaries at the onset and cessation of a whistle candidate has an advantage of enabling a software process to accurately integrate volumetric airflow rate over the full duration of the whistle candidate, and arrive at a measure of the volume of a user's forced exhalation—a valuable metric for assessing lung function. Registering temporal boundaries during a whistle candidate may enable a software process to determine peak expiratory rate for a trial without having to consider the full whistle candidate, thus enabling the software process to report peak flow rate more quickly, with lower memory requirements, less calculation and less drain on the mobile device's battery—thus improving the functioning of the device. Registering temporal boundaries corresponding to the start of acoustic input data frames is essential to a range of frame-wise digital signal processing techniques—filtering, windowing, correlation, convolution, Fourier analysis, Cepstrum, the Harmonic Product Spectrum method, etc.—of utility in producing well-functioning implementations of embodiments of the present invention. Temporal boundaries can be represented through various secondary units, such as sample index, frame index and lag index, but all fundamentally correlate to points in time.

According to yet another aspect of one or more embodiments, an aspect of the software process is to determine a "baseline" acoustic context in which a forced exhalation through a whistle has, will, or might take place. Determining a baseline acoustic context may have an advantage of assisting the software process to distinguish a whistle candidate from other acoustic events, noise, and silence within the acoustic context. A range of features may potentially be identified, tracked and evaluated during definition of a baseline acoustic context, without departing from the scope of the present invention. Some such features include acoustic information of the whistle and/or uses of the whistle, for instance: mean, median and maximum acoustic amplitude, the absolute value of mean, median, and/or maximum acoustic amplitude, spectral envelope, noise threshold, dominant spectral peaks, frequency centroid, harmonicity, normalized low-frequency energy ratio, and periods of regular periodic alternating silence and noise. One relatively simple approach to determining a baseline acoustic context might be to track maximum acoustic amplitude for a period of time, and then use this maximum acoustic amplitude as a threshold for distinguishing substantially silent periods from whistle candidates. A more sophisticated approach to determining a baseline acoustic context might entail identifying a range of features within the time and/or frequency-domain, such as active noise frequencies, in order to enable active noise calculations (e.g., for active noise cancellation, active noise reduction, active noise control, for use by a filtering algorithm in identifying and removing background noises, etc.), or to select one frequency-detection algorithm as most appropriate for the given context, out of a set of frequency detection algorithms. Determining a baseline acoustic context for a given trial may rely entirely on pre-calculated results. Determining a baseline acoustic context may be entirely based on explicit or implicit assumptions (potentially encoded in software instructions, or stored in memory accessed by software instructions) about the mobile device's audio subsystem (e.g., microphone gain, sensitivity, distortion, clipping point, noise level, etc.), and or context of use (e.g., further capabilities of the microphone or mobile device within a given context of use, etc.).

Once features of a mobile device's baseline acoustic context have been established, they can be used not only to support whistle-based spirometric measurements, but also to support a wide range of other acoustic control, command and measurement-related activities unrelated to spirometric measurement. The acoustic environment may include information about acoustic sounds within the environment surrounding the mobile device, as well as various deviations to acoustic sounds based on environmental knowledge. For example, if the baseline acoustic context established by an embodiment of the present invention determines that the acoustic environment includes significant cocktail party-like noise and/or acoustic deviations such as echoes and atmospheric pressure variations, other software processes sharing access to the same microphone for other purposes (such as voice-based search, voice-based purchase, singing-based musical transcription, etc.) could use this information about the baseline acoustic context to increase their own selectivity and reject the noise. Thus, establishing features of a mobile device's baseline acoustic context has the potential to improve the functioning of the mobile digital device not only for spirometric measurement, but also for range of activities that extends beyond spirometry.

In some embodiments, features of a baseline acoustic context may be established before a whistle candidate (or collected/recorded samples) has begun. Establishing baseline features immediately before a whistle candidate has begun increases the likelihood that the acoustic context will not have changed significantly by the time the whistle candidate occurs. In some embodiments, features of the baseline acoustic context may be established after a whistle candidate has begun, with an advantage that there is no need for a user to wait for baseline establishment to complete before starting a trial. In some embodiments, features of the mobile device's baseline acoustic context may be established continuously, or between trials—with an advantage that routine or time dependent noises (such as the chime of a grandfather clock) may be anticipated and adjusted for during a trial. In some embodiments, baseline features may be updated during a whistle candidate, with a potential advantage of improving detection of frequency during the latter portion of a whistle candidate, and/or improving detection of cessation at the end of a whistle candidate.

A further aspect of one or more embodiments is that the software process provides instruction to be made available to the user through the mobile device. Such instruction may occur before the trial, with advantages of reminding the user how to perform the trial before any mistakes have been made during the trial, and thus, with less risk of coming across as admonishment or criticism. Instruction may also occur after the trial, with an advantage that it is possible, at this point to provide tailored correctional feedback that can aid a patient to improve the way they perform trials in the future. Instruction may also occur during the trial. Some instructions may occur before or after every trial, while some instructions may occur less frequently. In one or more embodiments, some instructions last for a duration in time. In some embodiments, the user must acknowledge some instructions, with advantages of a) underscoring the importance of these instructions, or b) enabling an experienced user to step through a sequence of already well-understood instructions quickly (as opposed to having to wait for each instruction's time period to elapse). In some embodiments, instruction may be adaptive. For instance: instructional text may be more sternly worded when a user error is repeated; instructional text may be worded in a more welcoming manner if a user is determined to be a novice user; instructional audio may guide a user to hold the whistle closer to (or farther from) the mobile device based on current (or prior) relative distance. Without departing from the scope of the present invention, instructional feedback in various embodiments may be textual, graphical, animated, auditory, vibrotactile, and/or multimodal.

According to one or more embodiments, instructions may be presented concurrently with establishing features of a baseline acoustic context, with an advantage that a user will not perceive that they need to wait for features of baseline acoustic context to be established.

Another aspect of one or more embodiments is that the software process evaluates the validity of whistle-sound candidates. In some embodiments, this evaluation may take the form of a set of comparisons against a parametric model. To give a simplified example, a whistle candidate might be accepted as valid if it is neither too short nor too long in duration; in this case, the parametric model includes two duration thresholds. In more sophisticated embodiments, evaluation may involve machine learning approaches, for instance, training an artificial neural network (ANN) on a large set of predetermined valid and invalid whistle candidates, then employing the trained network to assess the validity, or contribute to the assessment of validity, of new whistle candidates.

According to one or more embodiments, the whistle has an inlet conduit with a mouthpiece with a central axis that is substantially coplanar with a central axis of the outlet conduit. An advantage of the central axis of the mouthpiece or inlet being substantially coplanar with the central axis of the outlet conduit is that a balanced weight distribution is encouraged, and twisting torques are limited when the whistle is held by a user's lips. The user does not need to exert undue effort to keep the whistle from twisting. Additionally, this geometry supports lateral symmetry, which may be aesthetically desirable; it helps to ensure that a whistle does not look off-kilter or unstable when correctly positioned for use.

According to one or more embodiments, the whistle comprises a housing that is configured to attach either directly to the mobile digital device, or else indirectly, to a second housing configured to hold the mobile digital device. According to one or more embodiments, the whistle comprises a housing configured to hold the mobile digital device. According to one or more embodiments, the whistle comprises a housing configured to additionally house the functionality of an inhaler dispenser and/or dosage counter or meter, and/or medicine container, with an advantage of reducing the number of asthma management-related items a person needs to keep track of and carry on their person.

According to one or more embodiments, the whistle includes a cover which can be used to keep the mouthpiece clean. In some embodiments, this cover is attached to the whistle by a flexible joint, strap, or cord, with an advantage that the cover can be removed from the mouthpiece with less risk of loss or misplacement. In some embodiments, the cover has a secondary "resting" or attachment location on the whistle, so that while the whistle is in use, there is an intuitive, natural place for a user to keep the cover. In some embodiments, the mouthpiece cover does not detach, but instead retracts to reveal the mouthpiece, in a manner conceptually similar to the way a lipstick's inner casing retracts to reveal lipstick, or the way a ballpoint pen's casing retracts (relative to an enclosed pen tip) to reveal the pen tip. (Such embodiments require that the mouthpiece cover is open-ended). In some embodiments of the whistle there is a sliding constraint between the whistle body or the inlet tube and the mouthpiece cover, such that the mouthpiece cover can be retracted through a sliding motion, thus revealing the mouthpiece. Other embodiments of the whistle include a twisting, screw-like or spiraling constraint (such as, for example, the thread constraint between a screw and a nut) between the whistle body or the inlet tube and the mouthpiece cover, and twisting the cover relative to the whistle body or inlet tube will result in the cover retracting to reveal the mouthpiece. In some embodiments that include a sliding or twisting constraint, there are additionally end-point constraints that limit the extent to which the mouthpiece cover can move during retraction or extension. Some embodiments further include detents or catches at or near endpoints of retraction and extension, such that the mouthpiece cover will "click" into place (sonically and/or haptically) when moved into fully retracted (mouthpiece uncovered) or fully extended (mouthpiece covered) positions, with an advantage of clearly communicating the state of the whistle to the user. In some embodiments, the cover serves as a grip or handle, by which the user may effectively hold the whistle during use, and/or manipulate the cover. Some embodiments may configure a retraction to be an initiating action for recording samples/trials.

According to one or more embodiments, the whistle is "pocket-portable," or of a size and shape conducive to being carried in a person's pocket. According to one or more embodiments, the whistle is wearable. In some embodiments, the whistle is wearable around a user's neck by means of a lanyard, or about the waist, by means of a belt clip.

Though the description above contains specificities, these specificities should not be construed as limiting the scope of embodiments, but merely as assisting in the presentation of illustrative examples. Additional variations are possible; for example, alternate variations of the whistle could incorporate a fixture and/or holes that enable the whistle to be worn using a strap or a necklace, or alternatively, used as part of a keychain. Alternate variations of the system's software process could automatically monitor for several trials in succession, rather than just one trial. Thus, the scope of the embodiments should be determined by the appended claims and their legal equivalents, rather than by any specific examples given.

As described above, the various embodiments include spirometric measurement systems for capturing, generating, measuring, determining, or making human expiratory airflow-related measurements accessible to hand-held mobile electronic devices. A spirometric measurement system may include a compact portable whistle and a physically separate hand-held mobile electronic device. The compact portable whistle may be configured, equipped, designed or arranged to produce acoustic emissions with a frequency that varies with airflow rate, and generate and/or send information that is suitable for deriving airflow-based measurements to the acoustic input unit of the hand-held mobile digital device. The hand-held mobile electronic device may be configured to receive, collect, and/or use information collected by its acoustic input unit (e.g., information received the compact portable whistle, etc.) to generate, compute, or determine human expiratory airflow-related measurements.

Methods of spirometric measurement using a whistle having a pre-determined correlation between through-flowing airflow per unit time and frequency of acoustic emissions from the whistle may include determining, via a processor of a mobile electronic device, a baseline acoustic context, recording samples based on information received via a microphone of the mobile electronic device, determining a frequency value for an acoustic signal included in the recorded samples, determining an expiratory airflow rate value based on the determined frequency value, determining a respiratory parameter based on the determined expiratory airflow rate value, generating spirometric information based on one or more of the recorded samples, the determined, frequency value, the determined expiratory airflow rate value, and the determined respiratory parameter, and rendering the generated spirometric information. In some embodiments, the method may further include receiving (in the processor) an identifier (e.g., from the whistle, from user input, etc.), performing a validation based on the received identifier and/or identifying a correlation of the whistle based on the received identifier. In some embodiments, the mobile electronic device may include a user input capability (i.e., user interface elements), and the operation of receiving the identifier may include (or may be accomplished by) the processor receiving the identifier via the user input capability of the mobile electronic device. In some embodiments, the mobile electronic device may include an automatic identification tag reading capability coupled to the processor, and the operation of receiving the identifier may include (or may be accomplished by) the processor receiving the identifier from an automatic identification tag. As such, the receiving an identifier at the mobile electronic device may include (or may be accomplished by) receiving the identifier at the mobile electronic device via a user input capability of the mobile electronic device and/or receiving the identifier at the mobile electronic device via an automatic identification tag reading capability of the mobile electronic device.

Further embodiments include a portable whistle having a predetermined correlation between through-flowing airflow per unit time and frequency of acoustic emissions from the whistle, usable for sensing the rate of a user's expiratory airflow as it passes through the whistle, and transmitting the rate through electrically passive means, as said frequency of acoustic emissions from the whistle to a physically independent mobile digital device with a means of user input, a means of acoustic input, and software processing capabilities. The whistle may include a mouthpiece at a first end of an inlet conduit having a central axis. The whistle may include an outlet conduit having a central axis. The whistle may include a central cavity, positioned between the inlet conduit and the outlet conduit, and having a central axis. The whistle may include an airflow guide, positioned between the mouthpiece and the central cavity, the airflow guide including one or more smooth and continuous surfaces that guide said user's expiratory airflow into a vortex within said central cavity to produce an acoustic emission as said expiratory airflow exits said outlet conduit, in which the whistle has sufficiently low airflow resistance to produce an acoustic emission detectable by said mobile device that substantially corresponds to a peak expiratory airflow rate of said user, and the acoustic emission correlated to airflow rate is produced without using any moving parts. In some embodiments, the respiratory parameters may be determinable based on the frequency of said whistle's acoustic emissions and said correlation may be determined using the mobile device.

In some embodiments, the mouthpiece may be sized and shaped to enable a fluid-tight seal between the mouthpiece and the lips of a user when the user performs a forced exhalation through the whistle. In some embodiments, in the mouthpiece includes at least one of: i) an external surface that is substantially smooth and continuous and does not contain sharp-angled bends over at least a portion of the mouthpiece that is engaged by the lips of the user, ii) an external surface that has an oblong cross-section, and iii) an external surface having at least one cross-sectional dimension that does not increase in the direction of through-flowing airflow.

In some embodiments, the whistle may include a grip region including at least one of: i) a surface color that differs from that of at least one other feature of the whistle, ii) a surface finish that differs from that of at least one other feature of the whistle, iii) a surface texture that differs from that of at least one other feature of the whistle, iv) a material that is softer than the mouthpiece, and v) a material that presents greater surface friction to a human hand than at least one other feature of the whistle.

In some embodiments, the whistle may include an outlet conduit that has an exit opening. The whistle may further include a barrier region proximal to the exit opening of the outlet conduit, said barrier region maintaining a minimum spacing, from at least one direction, between the exit opening of the outlet conduit and at least one of: the means of acoustic input of the physically independent mobile digital device, a user's hands. In some embodiments, the barrier region may include tubular structure that is substantially axially-aligned with the central axis of the inlet conduit. In some embodiments, an open cross-sectional area of the tubular structure increases with the direction of airflow through the outlet conduit.

In some embodiments, the tubular structure of the barrier region surrounds the exit opening of the outlet conduit such that expiratory airflow flows from the exit opening of the outlet conduit through the tubular structure of the barrier region. In some embodiments, the barrier region includes a false outlet such that expiratory airflow from the exit opening of the outlet conduit does not flow through the tubular structure of the barrier region. In some embodiments, a cross-sectional area of the tubular structure at a distal end of the tubular structure is sufficiently large such that the distal end of the tubular structure cannot be held within the lips of the user as easily as the mouthpiece.

In some embodiments, the whistle may include a plurality of outlet conduits. In some embodiments, each of the outlet conduits may be substantially perpendicular to the prevailing direction of airflow into the mouthpiece. In some embodiments, the outlet conduits may include first and second outlet conduits that are approximately equidistant from the left and right ears of a user performing a forceful exhalation through the whistle, such that acoustic emissions are produced in stereo sound.

In some embodiments, the whistle includes a first airflow guide that channels incoming airflow into a vortex through a first central cavity towards a first outlet conduit, and a second airflow guide that channels incoming airflow into a vortex through a second central cavity towards a second outlet conduit. In some embodiments, the outlet conduit includes an exit opening, and the exit opening is oriented substantially perpendicularly to the prevailing direction of airflow into the mouthpiece.

In some embodiments, the central cavity is at least partially defined by a wall having at least one of: a portion that follows a substantially circular contour, a portion that has a variable radius, a portion that has a continually variable radius, a portion that follows a spiral contour, and a portion that follows a substantially logarithmic spiral contour. In some embodiments, the central axis of the central cavity is substantially parallel to central axis of the inlet conduit. In some embodiments, the central axis of the central cavity is substantially perpendicular to the central axis of the inlet conduit. In some embodiments, the airflow guide includes a smooth and continuous transition portion between an interior surface of the inlet conduit and an interior surface of the central cavity. In some embodiments, the airflow guide includes at least one of: one or more stationary vanes, and one or more channels that direct airflow from the inlet conduit into the central cavity.

In some embodiments, the inlet conduit, the outlet conduit, the central cavity and the airflow guide of the whistle are formed by no more than three separate components. In some embodiments, each of the separate components includes an injection molded part. In some embodiments, the inlet conduit, the central cavity and the airflow guide are formed by securing a first component and a second component, in which the outlet conduit is defined by one of the first component and the second component. In some embodiments, a housing that is configured to hold the mobile digital device. In some embodiments, a housing that is configured to attach to the mobile digital device, or to attach to a second housing configured to hold the mobile digital device. In some embodiments, at least one of the respiratory parameters determined using said mobile device is based on a measurement of the peak expiratory airflow rate of said user. In some embodiments, said respiratory parameters include at least one of PEFR and $FEV_1$. In some embodiments, the central axis of the inlet conduit at the first end of the inlet conduit is substantially parallel or substantially coaxial with the central axis of the outlet conduit. In some embodiments, a portion of the mouthpiece or inlet conduit has a central axis that is substantially coplanar with the central axis of the outlet conduit. In some embodiments, the mobile digital device is a mobile phone, a personal digital assistant, a tablet, or a mobile gaming platform.

In some embodiments, the whistle may include a housing that is configured to contain a dispenser with medicine for inhaling. In some embodiments, the whistle may include a medicine delivery channel that extends between the mouthpiece and the housing to provide a fluid flow pathway for medicine traveling from the dispenser contained in the housing through the mouthpiece and into the respiratory system of a user. In some embodiments, the acoustic emissions produced by the whistle are audible to humans. In some embodiments, the acoustic emissions produced by the whistle are ultrasonic.

In some embodiments, the whistle may include at least one of: a visual indicator, a human readable identifier, and an automatic identification tag including at least one of: a bar code, QR code, an RFID tag, an NFC tag, and a machine-readable tag. In some embodiments, the whistle may include a mouthpiece cover. In some embodiments, the mouthpiece cover is detachable from the whistle, the whistle further including a cord or strap that connects the whistle to the mouthpiece cover, whereby the mouthpiece cover may be detached from the whistle with reduced risk of loss.

In some embodiments, the mouthpiece cover may further include an open-ended tubular structure, and a movement constraint structure, usable to constrain movement between the mouthpiece cover and at least one of the mouthpiece and inlet conduit, whereby the mouthpiece cover may be moved, in accordance with the movement constraint structure, towards the distal end of the central cavity, uncovering the mouthpiece. In some embodiments, the movement constraint structure is a sliding or twisting movement constraint structure. In some embodiments, the movement constraint structure further includes at least one detent, whereby the mouthpiece cover may lock into place relative to at least one of the mouthpiece and the inlet conduit.

As discussed above, the various embodiments include methods for spirometric measurement using a whistle having a pre-determined correlation between through-flowing airflow per unit time and frequency of acoustic emissions from the whistle, which may include determining, via a processor of a mobile electronic device, a baseline acoustic context, recording samples based on information received via a microphone of the mobile electronic device, determining a frequency value for an acoustic signal included in the recorded samples, determining an expiratory airflow rate value based on the determined frequency value, determining a respiratory parameter based on the determined expiratory airflow rate value, generating spirometric information (e.g., based on one or more of the recorded samples, the determined frequency value, the determined expiratory airflow rate value, and the determined respiratory parameter) and rendering the generated spirometric information.

According to one or more further embodiments, the external shape or profile of the whistle may be substantially similar to that of a kazoo, referee's whistle, or shell, with an advantage of presenting a user with a familiar shape and/or legible connotations for use.

According to one or more embodiments, transitions between logical or physical parts of the whistle may include substantially continuous rounded transitions, with advantages that may include reduced airflow resistance, improved acoustic qualities, reduced turbulence, improved usability, and/or improved aesthetics.

According to some embodiments, the whistle may include an outlet tube that is recessed relative to a proximal exterior surface of the whistle, so as to reduce or eliminate the outlet's influence on the exterior envelope of the whistle, with several potential advantages. A recessed outlet tube may reduce the chances of a user's fingers touching or covering the outlet tube during measurement, and may facilitate removing or stowing the whistle from cloth containers such as pockets or handbags without the outlet catching on cloth edges or surfaces.

According to one or more embodiments, the whistle may include one central cavity with two outlet tubes on opposite ends. According to one or more embodiments, the whistle may include one central cavity with two outlet tubes on opposite ends having different diameters. A whistle with multiple outlet tubes may emit stronger acoustic emissions with less directionality; a whistle with multiple outlet tubes of differing diameters may enable a software method to detect when/whether a user is accidentally or purposefully covering one outlet.

According to various embodiments, the internal and external cross-sectional diameters of the outlet tube may vary in order to address one or more design or engineering constraints, such as visual aesthetics, auditory aesthetics, clear acoustic communication with a mobile device, and portability. In some embodiments, the internal or external cross-sectional area of the outlet tube may be constant. In some embodiments, the internal or external cross-sectional area of the outlet tube may be variable. In some embodiments, the internal or external cross-sectional area of the outlet tube may vary along a central axis of the outlet tube. In various embodiments, the outlet tube's cross-sectional area or radius may vary continuously along a central axis of the outlet tube. In some embodiments the cross-sectional area or cross sectional radius of at least a portion of the outlet tube may vary along a central axis of the outlet tube according to a mathematical function (e.g. linear, exponential, logarithmic, etc.), with, or against, the prevailing direction of expiratory airflow passing through the outlet tube. In some embodiments, the outlet tube may join the main cavity through a smooth, continuous transition. In some embodiments, the outlet tube may include sections of variable cross-sectional area, as well as sections of constant cross-sectional area. In some embodiments, the outlet tube or a portion thereof may be conically shaped. In some embodiments, the outlet tube may join the main cavity through a right-angled bend.

According to some embodiments, a central axis of the whistle's outlet tube may be oriented, relative to the central axis of the mouthpiece, such that the prevailing direction of airflow out of the outlet tube is outward and away from the user during a user's exhalation through the whistle. According to alternate embodiments, the prevailing direction of expiratory airflow through the outlet tube may be, for example, up, down, sideways, or towards the user. Depending on the set of aesthetic, commercial and usability constraints considered most important for a particular embodiment, one direction of outflow may be preferable to another.

According to one or more embodiments, the mouthpiece and/or inlet of the whistle may have a circular internal and/or external cross section. According to one or more embodiments, the mouthpiece and/or inlet may have an oblong (e.g. oval, rounded rectangular, etc.) internal and/or external cross-section. According to one or more embodiments, an cross-sectional internal and/or external shape of the mouthpiece and/or inlet of the whistle may vary along a central axis. According to one or more embodiments, an internal and/or external cross sectional shape of the mouthpiece and/or inlet may transition from oblong to circular, along a central axis of the mouthpiece. According to one or more embodiments, an internal or external cross sectional shape of the mouthpiece and/or inlet may transition to a cross-sectional shape that has at least one flat portion. According to one or more embodiments, an internal or external cross sectional shape of the mouthpiece and/or inlet may transition to a cross-sectional shape that is rectangular.

According to one or more embodiments, determining a baseline acoustic context, and/or determining a recording device feature, may include determining, before, during or after a measurement trial, one or more of the following: whether a mobile device has or has access to the necessary audio-related resources (e.g. available memory, available processing power, audio recording-related resources, etc.) for performing operation(s) of the method; whether audio-related resources of the mobile device necessary to perform operation(s) of the method are or will be accessible to the software method; whether resources of the mobile device usable to perform operation(s) of the method are configured in such a way that the mobile device may perform or continue performing operation(s) of the method; whether resources of the mobile device usable to perform operation(s) of the software method are configured in such a way that the mobile device may perform or continue performing operation(s) of the method in real-time; whether the processing of audio data by operation(s) of the method is occurring or has occurred in real-time; which values for particular audio-related settings (e.g. sample rate, sample bit-depth, frame buffer size, sample-frame format, pre-processing filters, noise cancellation settings, etc.) the mobile device is configured to use or can be configured to use; whether or not audio data is being "dropped" (lost); whether the availability of one or more of the mobile device's audio resources for use by operation(s) of the method will change, is changing or has changed (e.g. a phone call on a mobile phone forcing interruption/conclusion of a measurement trial conducted by phone, any changes in resource authorizations—such as an audio resource being re-allocated by the mobile device's operating system for use by another process, etc.); whether other processes running on or via the phone are using, or are requesting to use, resources that are required, or may be required, by operation(s) of the method; the nature and/or extent of any pre-processing that audio information received at the microphone of the mobile device is subjected to (e.g. filtering, noise cancellation, distortion, clipping, etc.) prior to becoming available to the method. The more information the method has available to it regarding the nature, availability, state, and utilization of a mobile device's audio-related resources, the better equipped the method may be to: a) determine whether a valid spirometric measurement may be, is being or has been successfully performed, and b) produce and present accurate and granular instructional and/or diagnostic information to a user, which may increase the likelihood of user successfully performing subsequent measurement trials, or may otherwise improve a user's experience of the system.

According to one or more embodiments, the method may include determining whether a portion of audio information received at the microphone of the mobile device before, during or after a measurement trial is classifiable according to one or more (flat or hierarchical) classifications. Examples of whistle-sound classifications may include: a valid whistle-sound (e.g. a sound produced by the whistle, corresponding to a correctly performed complete exhalation performed by a user through the whistle); an invalid whistle sound (e.g. a sound produced by a whistle or other sound source, but not corresponding to a correctly performed complete expiratory maneuver by a user through the whistle, or a correctly performed and complete expiratory maneuver performed through a whistle, but not performed by a particular user, or not performed through a particular whistle or type of whistle); a whistle-sound performed by a given user; a whistle-sound originating from a given whistle or type of whistle, etc. Examples of respiratory sound classifications not involving a physical whistle device may include: inhalation or exhalation through the mouth; slow, medium or fast inhalation or exhalation through the mouth; raspy expiration, blowing, coughing; wheezing; squeaking; whistling originating from a user's respiratory tract; whistling originating from a user's lips, nasal inspiration, nasal expiration, sniffling, throat-clearing, etc. Examples of inspiratory or expiratory sound classifications that may support a) rejection of invalid sounds, b) improved measurement accuracy, and/or c) "catching" a user who is attempting to cheat during a measurement trial may include: humming; singing; yelling; squealing; whistling originating from human lips; sounds of known toy or classes of toys; sounds from other known types of whistles (e.g. a slide whistle); sounds from another available type of spirometric whistles; sounds from a whistle with an outlet tube that has been partially or entirely covered (e.g. by a user's hand, a burqa, etc.), etc. Examples of environmental sound classifications that may support rejection of invalid sounds and improved measurement accuracy may include: tea kettle whistles; singing; humming; television sound; radio sound; screaming child; background conversation; foreground conversation; vacuum cleaner; blender; dish-washer; washing machine; road noise, airplane noise; wind; wind-whistling; restaurant noise; etc. Examples of device audio processing artifact sound classifications that may support rejection of invalid sounds and improved measurement accuracy may include classifications such as: amplitude clipping, filtering, dropped samples, dropped frames, quantization, muting, gain reduction or increase of effective input gain, etc.). Such classification of sounds may facilitate rejection of invalid trials, improve the overall accuracy of trials determined to be valid, and result in improved instructive or diagnostic feedback for the user and/or the user's network of care (e.g. by presenting more contextually relevant messages to the user via a display of the mobile device, or to a parent, via email, etc.).

The method may employ a range of approaches to enable and support identification/classification of sounds according to such classifications as those described above. A description of one approach to supporting such classification is as follows: A supervised machine learning technique is employed, using a) a labeled data set containing sounds that match (and sounds that do not match) a particular classification (e.g. toy train whistle sounds), and b) a means of evaluation (e.g. a cost function, a probability function, etc.), to iteratively or recursively train an artificial neural network (ANN), support vector machine (SVM), or other form of machine learning model. During training of the machine learning model, model parameters are configured, and the model is used in conjunction with the sound data set to produce categorization results. The categorization results are then evaluated according to the means of evaluation, which penalizes inaccurate categorizations and/or rewards accurate categorizations. Model parameters are reconfigured, based on the evaluation of the categorization results, and further iterative or recursive training step(s) take place. Training continues until the model's classification accuracy exceeds a required threshold, at which point the model may be made available to one or more embodiments of the method for use in categorizing a sound (e.g. train whistle, or not train whistle, etc.). Software tools and environments commonly used to train classifiers in such a fashion may include Google's Tensorflow and the Keras python library for deep learning.

Numerous variations in the training and usage of machine learning models for categorization tasks are possible without departing from the spirit of the invention (e.g. variations in training data set size, model types, layers and topologies, evaluation means, etc.), as are other approaches to categorization (e.g. usage of scale-invariant feature transforms, or other approaches to feature detection). For example, a convolutional neural network may be employed.

An aspect of one or more embodiments is that one or more machine learning model(s) (e.g. artificial neural network model(s), etc.) may be employed by the method (e.g. for classifying sounds, for providing instructional or diagnostic feedback, for determining frequency, determining flow rate, etc.). In some embodiments, one or more of the machine-learning models may be partially or wholly trained by machine learning technique(s); in some embodiments, one or more of the machine learning models may be provisioned with parameters that are hard-coded, or procedurally generated.

In some embodiments, the machine learning model(s) may be replaced, updated or configured (e.g. the "weight" parameters of an artificial neural network model may be updated or replaced, etc.), with an advantage of enabling ongoing incremental refinement of the method as a whole, without requiring substantial structural changes to the method, beyond the changes affecting a given machine-learning model.

An aspect of one or more embodiments is that the method employs a machine-learning model and/or classifier (e.g. artificial neural network, etc.) to identify a feature within a whistle candidate sound. In various embodiments, one or more machine learning models are employed to detect: an onset of a whistle candidate; a cessation of a whistle candidate; a real-time frequency (or flow rate) of a whistle candidate; a peak frequency (or peak flow rate) of a whistle candidate; a sequence of frequencies (or flow rates) that corresponds to a sequence of audio frames. In some embodiments, the method employs one or more machine-learning models or portions/structures of machine learning models to identify a flow rate, or respiratory parameter(s) such as PEFR, FEV1 or FVC from audio samples directly, (i.e. without a separate or independent step or operation of determining frequency values). In one or more embodiments, the method performs a regression, to more reliably obtain the value of a substantially continuous variable (e.g.

frequency or flow rate over the course of a candidate whistle sound, or over the course of a validated whistle sound, etc.). Through use of such models and classifiers, the method may perform spirometric measurements with improved accuracy, reliability and noise-immunity.

According to one or more embodiments, the method may employ dynamic programming techniques (such as the viterbi algorithm), in conjunction with one or more cost or probability functions, to determine one or more sequences of frequencies or flow rates (e.g. sequence of most-likely fundamental frequencies, sequence of most-likely flow-rates, etc.) that correspond to a sequence of audio frames.

According to one or more embodiments, the method may calculate and or represent (as a data structure, etc.) multiple versions of an estimate or measurement of a frequency, flow rate or respiratory parameter; for instance: a real-time measurement, a real-time measurement before a peak frequency has been determined, a real-time measurement after a peak frequency has been determined, a measurement after a respiratory maneuver has been performed, etc. According to one or more embodiments, the method may employ a peak frequency to determine a continuous frequency contour extending in one or more directions, temporally, from the peak frequency.

According to one or more embodiments, the method may include determining, potentially through the use of classification means such as those described above, whether a user is attempting to cheat, before, during or after a measurement trial. For example, a user may employ sounds other than the those produced by the whistle, or attempt to inappropriately modify their usage of the whistle, or modify the whistle itself, in an attempt to cause the system to respond as though a valid whistle were occurring, or to cause the system to report a higher or lower flow rate than the user would produce through proper usage of the whistle. According to some embodiments, if it is determined that a user has attempted to cheat, the method may subsequently present appropriately tailored feedback. Such feedback may be presented to the user, a user's parents, and/or other members of a user's network of care.

An aspect of one or more embodiments is that a determination that a whistle-sound represents a valid or invalid whistle-sound may be based on the whistle-sound, or may based on the whistle-sound in combination with one or more other identified/classified sounds that have occurred before, during or after the whistle sound. For example, if a whistle sound overlaps or is substantially close to the sound of a cough or the sound of a child screaming, the whistle may be determined to be invalid. Determination of whistle sound validity may additionally be based on which respiratory parameter(s) the system is configured to measure and/or report. (More stringent requirements may exist for effective measurement of some respiratory parameters than others). In the event that a whistle sound is determined to be invalid, a measurement trial may end early. In some embodiments, a whistle sound be determined to be invalid if the whistle-sound ends abruptly or prematurely.

In various embodiments, an acoustic device (e.g., whistle) may include one or more elements configured to modify at least a portion of the airflow provided to the whistle (e.g., via the inlet). The one or more elements configured to modify at least a portion of the airflow provided to the whistle may be configured to reflect, refract, and/or attenuate the airflow guided through one or more routes within and or leading out from the whistle. For example, the whistle may include one or more of a flow controller, an obstruction element (e.g., obstructor), a flow limiter, a valve, an opening, etc. and/or a combination thereof. Various examples are described below. However, any element or device configured to modify at least a portion of the airflow may be included in the whistle. In some embodiments, the element configured to modify at least a portion of the airflow may include one or more properties to allow the element to change, deform, or actuate from a first position to a second position based on the forces associated with the airflow provided to the whistle. For example, the element configured to modify at least a portion of the airflow may retain a shape, configuration, or orientation or remain in a first position when the airflow and/or back pressure is below a threshold value or range. In response to the airflow and/or back pressure reaching or exceeding the threshold value or range, the element may change or deform or the element may move to a second position.

At least one of the one or more elements configured to modify at least a portion of the airflow provided to the whistle is non-rotating or configured such that the element does not rotate about an axis, line, or point as the airflow interacts with the element. For example, one or more attributes (e.g., size, shape, material, configuration, arrangement, orientation, etc.) of the element configured to modify at least a portion of the airflow may modify the stream of air such that a vortex created by the modified stream of air is different from a vortex created if the element configured to modify at least a portion of the airflow is not provided within the stream of air. In some embodiments, while forces associated with the stream of air may cause the element configured to modify at least a portion of the airflow provided to the whistle to move in a linear direction, the forces do not cause the element to rotate. In other words, the element configured to modify at least a portion of the airflow provided to the whistle is not a rotor, stator, spindle, chopper, or any other element configured to rotate around an axis, line, or point in response to contact with the airflow. An amount in which the one or more elements configured to modify at least a portion of the airflow within the whistle modifies or obstructs the airflow may be referred to as a degree of obstruction.

In some embodiments, the degree of obstruction may cause the whistle to generate different acoustic emissions. For example, the one or more elements configured to modify at least a portion of the airflow within the whistle may be arranged or configured to modify or regulate one or more of a frequency, an amplitude, and an intensity of an acoustic emission generated by an airflow introduced to the whistle.

Alternatively, or in addition, the degree of obstruction of the one or more elements configured to modify at least a portion of the airflow within the whistle may limit and/or reduce back pressure generated within the whistle. For example, as airflow is introduced at the inlet of the whistle, air is guided through one or more chambers to create a vortex. The centrifugal forces generated by the vortex may create back pressure that may undesirably effect spirometric measurements. For instance, the resistance created by the back pressure may require that a user use more pressure (e.g., blow harder) to maintain or increase the airflow provided to the inlet of the whistle in order to generate the acoustic emissions used to determine the spirometric measurements.

The degree of obstruction may be based on a location, orientation, and/or arrangement of the one or more elements configured to modify at least a portion of the airflow within the whistle. The location, orientation, and/or arrangement may be altered prior to an airflow being introduced to an inlet of the whistle. Alternatively, the location, orientation, and/or arrangement of the one or more elements configured to modify at least a portion of the airflow within the whistle may be dynamically altered while airflow is guided through the whistle. For example, the location, orientation, and/or arrangement of the one or more elements configured to modify at least a portion of the airflow may be modified or altered in order to limit how quickly a vortex is created within the whistle, to maintain a rate of airflow within the whistle (e.g., at a predetermined level or within a predetermined range), to release pressure when back pressure exceeds a predetermined threshold value or range, to direct the airflow towards or away from an air guide that creates the vortex, and/or to modify one or more characteristics of an acoustic emission such as a frequency, an amplitude, and/or an intensity. The location, orientation, and/or arrangement may be altered or modified such that different users may use the same whistle or same model of whistle (e.g., child or adult). Alternatively or additionally, the location, orientation, and/or arrangement may be altered or modified for different measurements of a single user.

In some embodiments, gravity may have no effect or influence on the degree of obstruction or the location, orientation, and/or arrangement of the one or more elements configured to modify at least a portion of the airflow within the whistle. For example, the one or more elements configured to modify at least a portion of the airflow within the whistle may perform or operate the same way no matter the orientation of the whistle when a user provides an airflow to the inlet such that the whistle will generate the same or substantially the same acoustic emissions if the whistle is oriented right-side up, up-side down, or sideways.

The one or more elements configured to modify at least a portion of the airflow within the whistle may be arranged or located in various positions with respect to the airflow guide configured to generate the vortex. For example, the one or more elements configured to modify at least a portion of the airflow may be provided before the airflow guide to compensate for any spike in pressure, in one or more walls of the airflow guide to modify one or more characteristics of the generated vortex (e.g. pressure, rotational velocity, shape, size, etc.), and/or in one or more walls of the whistle separate from a wall of the airflow guide to modify the airflow or the pressure.

An aspect of one or more embodiments is that the whistle may include a flow controller that governs how airflow may be allocated among alternate possible routes. Such a flow controller may expand the effective measurement range of a given whistle by supporting robust auditory emissions at low flow rates, while also supporting low back-pressure against a user's respiratory system at high flow rates. A flow controller may also contribute to ensuring that auditory emissions produced by the whistle at high flow rates are not unduly intense, powerful or shrill for a user. A flow controller may further ensure that acoustic frequency emissions produced by the whistle in response to expiratory airflow fall within a frequency range that consumer microphones, mobile devices and wireless telephony systems may accommodate.

According to some embodiments, the flow controller may allocate flow in a continuous fashion; allocating more flow to one route than another gradually (e.g. in response to, for instance, pressure within a certain region of the whistle increasing, etc.). For example, one or more umbrella valves could open continuously in response to pressure from expiratory airflow, changing the relative allocation of airflow through routes within and/or exiting the whistle (e.g. through a vent, vs. through an acoustic outlet tube, etc.).

According to some embodiments, the flow controller may alter relative flow allocations in discrete steps in response to airflow rate, pressure, noise level, etc.; in some embodiments, the flow controller may alter relative flow allocations in an all-or-nothing fashion.

In some embodiments, the flow controller may be static; it may maintain a relative allocation of flows between a plurality of routes, the relative allocation being substantially constant until a manual reconfiguration takes place, such as the turning of a knob, dial, etc., or a portion of the whistle being manually rotated, twisted, etc. with respect to another portion of the whistle, etc.), after which a different substantially constant relative allocation of flows may be maintained. In some embodiments, manual reconfiguration may alter the relative allocation of airflow through a plurality of routes by altering the relative sizes of a plurality of openings or passageway diameters. In some embodiments, the flow controller is dynamic: it may alter flow allocations in response to fluidic and/or mechanical changes, as these changes occur. For example, one or more umbrella valves may open continuously in response to pressure from expiratory airflow, changing the relative allocation of airflow through routes within and/or exiting the whistle.

In some embodiments, the flow controller may route airflow through alternate routes that converge at a later stage within the whistle. In some embodiments, the flow controller may route airflow into multiple central cavities and/or out of multiple outlet tubes. In some embodiments, the flow controller may allocate airflow between a) a route leading out of an outlet tube of a central cavity, and b) a route that does not lead out an outlet tube of a central cavity. In some embodiments, the route that does not lead out an outlet tube of a central cavity is a route that has never entered the whistle; for instance, the route may be a groove or keyway extending along the side(s) or bottom of the mouthpiece or inlet.

According to one or more embodiments, the flow controller and airflow guide may share common surfaces or passageway walls. Within some embodiments, the flow controller and airflow guide may be functionally or physically combined. In some embodiments the flow controller may include a relief valve or spill-over valve.

In various embodiments, the flow controller includes a vent that leads, directly or indirectly, out of the whistle. In some embodiments, a flow controller's vent may be integrated into the mouthpiece, such that when the user's lips enclose the mouthpiece, a portion of a user's expiratory airflow passes through the vent without ever entering the mouthpiece or whistle. In some embodiments, a flow controller's vent may be located between the mouthpiece and the portion of the whistle that the mouthpiece is coupled to (e.g. inlet), such that a portion of a user's expiratory airflow may escape through the vent, without entering any part of the whistle except the mouthpiece. In some embodiments, a flow controller's vent may alternatively be located in the mouthpiece, inlet, central chamber, outlet tube, enclosure, sidewall, internal wall, or any portion of the whistle having an exterior surface. In some embodiments, a flow controller's vent may include a single hole. In some embodiments, a flow controller's vent may include multiple holes, a dedicated passageway, or a semi-permeable surface or volume.

In various embodiments, the flow controller may include an obstructor that directly or indirectly limits airflow through the vent, or into a central cavity. In various embodiments, the obstructor may take various forms. The obstructor may include a flip cap or rotary cap, analogous to the caps commonly used in the spice/salt containers found in American kitchens to limit flows of spices. The obstructor may include a gate or paddle, hinged on one side, where degree of obstruction is a function of an angle of the gate or paddle. The obstructor may include a deformable flap. The obstructor may alternatively include a cover with an outward linear movement constraint (e.g. linear sliding joint) such that linear movement alters the extent of obstruction (i.e. in the manner of a valve in a typical internal combustion engine, that opens and closes through a linear motion). The obstructor may include a plug, which can be inserted to obstruct an opening or gap, or removed to open the opening or gap. Different kinds of obstructors have different advantages; flip caps and rotary cap-type obstructors may be inexpensive to create and easy to manipulate by hand; gate or paddle-type obstructors may move responsively and continuously with minimal friction, a deformable flap obstructor does not require a hinge, a cover-type obstructor with an outward linear motion constrains may suit certain form-factors, and a removable plug may inexpensively form a fluid tight seal that is easy to manipulate by hand and visibly communicates information to a user (e.g. the state of the obstructor—open or closed, etc.).

According to one or more embodiments, the degree of obstruction an obstructor presents to flow may be altered by manually twisting the mouthpiece relative to the inlet or whistle housing that the mouthpiece is coupled to. According to one or more embodiments, the degree of obstruction may be altered by adjusting an angle of a hinged or rotary cap or a deformable flap. According to some embodiments, the degree of obstruction may be altered by inserting or removing a removable plug. In some embodiments, the removable plug may remain attached to the whistle in its removed state to prevent loss, and may have a "resting position", such as a blind hole, where the plug may be securely placed (e.g. inserted) while in its removed state.

In various embodiments, the degree of obstruction an obstructor presents may be manually adjustable, to accommodate different flow ranges for different users in a simple and/or visually detectible fashion. In various embodiments, the degree of obstruction may automatically adjust in response to, for instance, a flow rate (e.g., expiratory airflow rate), a pressure (e.g. back-pressure exerted against expiratory flow due to airflow resistance presented by one or more features of the whistle), an acoustic amplitude (e.g. amplitude of audio emissions from the whistle), etc. The ability to vary the degree of obstruction may facilitate a one-size-fits-all (or one-size-fits-most, or one-size-fits-many) solution with little or no need for manual configuration.

In some embodiments, the degree of obstruction an obstructor presents may be indicated so as to be perceptible to a user, parent, healthcare provider, etc. For instance, if the degree of obstruction may be altered by rotating an obstructor relative to one or more obstructed passageways (e.g. manually, or by using a screwdriver, or by using a dedicated or non-standard torque-transferring device, etc.), the degree of rotation may be marked or include a visual indicator (e.g. a pointer pointing at a scale of printed numbers, raised plastic lines, variable color bar, bar of increasing thickness, etc.), so as to indicate the degree of obstruction. In some embodiments, indication of degree of obstruction may be communicated to the mobile device, via capacitive coupling (e.g. manually touching the whistle to a capacitive touch-screen of the mobile device; for discussion of information transfer via capacitive coupling, refer to this specification's discussion of capacitive coupling as a means of transferring whistle identifier from whistle to mobile device.), or an NFC or RFID tag transmission. For example, in some embodiments, the obstructor may comprise the wiper arm of a potentiometer, incorporated into and read by an NFC tag, such that the electrical resistance value read by the tag corresponds to the degree of obstruction of the obstructor. Indication of degree or strength of obstruction may be presented directly, or indirectly, discretely or continuously, via a mapping to another variable—for instance, the recommended age, height, weight, approximate peak airflow rate, etc. for a user, so as to enable the flow controller to be adjusted to support effective use of the whistle and/or respiratory measurement system by the user. In some embodiments, an obstructor may be keyed, or housed within the whistle, such that its degree of obstruction may not (or not easily) be altered by the user, but may easily (or more easily) be altered by a parent or healthcare provider through use of a specialized adjustment key, so as to help ensure reliable, accurate measurements when the user is (for example) a mechanically curious child. In some embodiments, calibration of the whistle is accomplished through such means, to prevent tampering or support "child-proofing". In some embodiments, the obstructor may be locked in place, such that its degree of obstruction may not (or not easily) be altered by the user, but may easily (or more easily) be altered by a parent, healthcare provider, etc., to, for example, facilitate child-proofing.

In various embodiments, manual or automatic control over the flow controller's degree of obstruction may be discrete (e.g. two or more "steps" from fully obstructed to fully un-obstructed), continuously variable, or a combination of discrete and continuously variable. One example of a combination of discrete and continuously variable automatic control over degree of obstruction might be to have a vent be totally obstructed below a certain back-pressure threshold, then, when the back-pressure threshold is exceeded, continuously decrease obstruction of the vent. Such an approach may improve accuracy and reliability at lower flow rates (e.g. below 2 L/s) while also supporting measurement of higher flow rates (e.g. above 10 L/s).

In various embodiments, the obstructor may not fully obstruct airflow at low flow rates (e.g. may not fully seal against a passageway wall, valve seat, etc.), with an advantage of precluding undesirable effects of static friction. For example, a duckbill or umbrella valve may be designed and incorporated so as not to close all the way under low/no airflow conditions, with an advantage that static friction associated with complete closure is not encountered.

In various embodiments, the flow controller may include a force-exerting element that influences the degree to which the obstructor will obstruct flow. In some embodiments, the force-exerting element may include a spring. Such a spring may be compressive, tensile, or a combination of compressive and tensile. The spring may be of constant-force or variable force. The spring may include a coil spring, a torsional spring, leaf spring, bending spring, solid spring, or a spring of some other geometry. The spring may be made of metal, plastic, a natural or synthetic rubbery material, another material, or a combination of multiple materials. The spring may be comprised of a compressible gas reservoir, such as the springy "air" pocket in a Nike Air sneaker. The spring may comprise a pair of magnets, or a magnet positioned at a distance from a magnetic material. In some embodiments, the force-exerting element may instead or additionally include a mass or weight, which exerts force through the force of gravity. Each of the above-mentioned examples of force-exerting elements has a different set of advantages that suit different weightings of various previously mentioned concerns such as accuracy, cost and aesthetic appeal.

In various embodiments, two or more of: the vent, the obstructor, and the force-exerting element may be combined within the same physical part, with an advantage of ease of manufacturing and assembly. For example, a "duck-bill" valve, umbrella valve, a valve comprising an annular flap, etc. may each simultaneously include an opening, an obstruction and a force-exerting aspect. A flap or gate obstruction may easily incorporate a weight or magnet as a force-exerting element. Examples of some commercially available products that may combine two or more of: the vent, the obstructor, and the force-exerting element may be found at www.minivalve.com or www.lmsvalves.com.

In various embodiments, one or more of the vent, the obstructor, and/or the force-exerting element may be positioned and/or shielded so as to minimize the short or long-term influence on the functioning of the flow controller from phlegm, mucus, water, bits of food, etc. that may accompany expiratory airflow. In some embodiments, the flow controller may be positioned near the opposite end of the whistle from the mouthpiece, which may reduce the chances of the flow controller's mechanism being compromised. In some embodiments, the spring may be shielded, or located in a region of the whistle that does not receive substantial expiratory airflow. In some embodiments, the obstructor's contact with other surfaces (e.g. a valve "seating" surface, etc.) may be minimized, to reduce potential for sticking friction.

In various embodiments, the flow controller's design may reduce or eliminate the impact of whistle orientation on measurement (e.g. by using light-weight materials and elements, not relying on weights as force-exerting elements, etc., so as to minimize effects of gravity when, for example, the whistle is tilted up, down, or sideways while in use). In various embodiments, the flow controller's design may reduce or eliminate the impact of varying environmental forces on measurement (e.g. by using non-mechanical designs, or using mechanical designs without "floating" or unattached elements, such as caged-ball valves, etc.), so as to support effective measurement in, for instance, an elevator, or an accelerating car.

According to an aspect of one or more embodiments, the flow controller may govern allocation of airflow of among alternate routes entirely through fluidic interactions; i.e. without a mechanical mechanism. (Such a flow controller may be referred to herein as a "fluidic flow controller"). A fluidic flow controller may be advantageous, in that no mechanical mechanism is required, which may reduce cost and complexity, improve reliability and eliminate or reduce calibration requirements. A flow controller without a mechanical mechanism may be particularly valuable in the context of respiratory measurement, where mucus, phlegm, water, and bits of food may accompany the expiratory airflow and adversely impact the functioning of sensitive and/or mechanical mechanisms.

According to one or more embodiments, the whistle may include a fluidic flow controller that utilizes the Coanda effect. One or more embodiments include a fluidic flow controller having a passageway (or an enclosed space) with an inlet, a first surface (or first region of a surface) extending from one side of the inlet to which fluid flow may preferentially adhere via the Coanda effect, and a second surface (or second region of a surface) extending from a substantially opposite side of the inlet that bends or turns away sharply from the prevailing direction of incoming fluid flow through the inlet, such that incoming flow from the inlet may not preferentially adhere to the second surface via the Coanda effect.

In one or more embodiments, the fluidic flow controller's inlet may include a nozzle that accelerates airflow, which may strengthen Coanda adhesion to a surface for improved directional control. In one or more embodiments, the fluidic flow controller may include a diffuser that may serve to reduce energy loss through the fluidic flow controller and/or increase pressure where pressure is required for production of sound. In one or more embodiments, the fluidic flow controller may include a nozzle used in conjunction with a diffuser, so as to make use of high velocity and/or low pressure in one region of the flow controller, while making use of low velocity and/or high pressure in another region of the flow controller. In one or more embodiments, the fluidic flow controller includes a splitter or a divider, which may guide a portion of airflow into a fluidic feedback loop or control stream that may influence the routing of airflow through the flow controller. One or more embodiments include a fluidic flow controller with an inlet, a vent outlet or vent outlet passageway, and a main outlet. One or more embodiments include multiple fluidic flow controllers operating in parallel or in series; such arrangements may allow for more complete control and/or higher efficiency.

In one or more embodiments, the whistle includes a fluidic flow controller that utilizes centrifugal force to dynamically govern how airflow may be allocated among alternate possible routes leading out of one or more exit passageways of the whistle.

What follows is a detailed description of exemplary whistles according to various embodiments in which an obstructor, a force-exerting element, and/or a vent of a flow controller may be arranged with respect to each other within a whistle passageway so as to exert a controlling effect on airflow passing through the whistle. However, the following description and corresponding figures are merely examples of a few variations and are not intended to limit the configuration or arrangement of one or more flow controllers or elements configured to modify or alter the airflow within a whistle.

Figure 27:
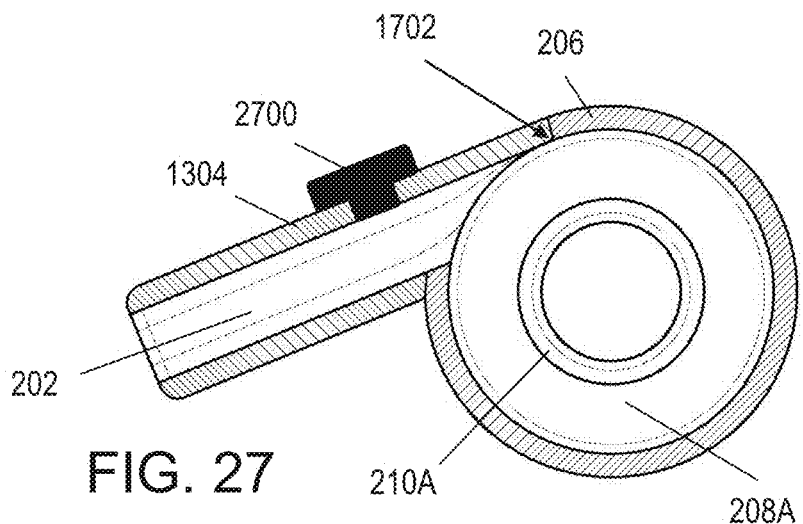
FIG. 27 shows a sectional side view of a whistle with a flow controller with a plug obstructor, in accordance with one or more embodiments.

FIGS. 28-37 depict sectional detail views that illustrate how obstructor and force-exerting elements of a flow controller may work in concert to control how airflow passes through or towards a vent. The figures on the left (i.e. FIGS. 28, 30, 32, 34 and 36) illustrate a "fully closed" state, with no air passing through or towards the vent, while the figures on the right (i.e. FIGS. 29, 31, 33, 35 and 37) illustrate an "open" state, with some air passing through or towards the vent. FIG. 27 is a modified version of the sectional view of a whistle depicted in FIG. 17, illustrating one way that flow controller elements depicted in detail views FIGS. 28-29 may be incorporated within a whistle.

Figure 28:
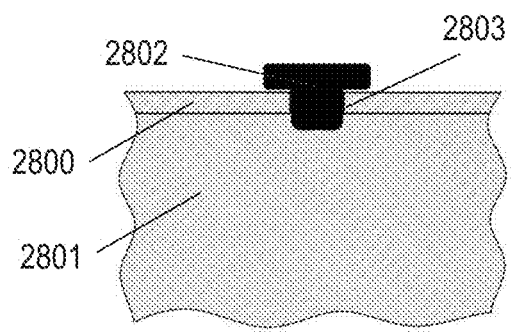
FIGS. 28 and 29 show a sectional detail view of a portion of whistle's flow controller with a plug obstructor present (FIG. 28) and absent (FIG. 29), in accordance with one or more embodiments.
Figure 29:
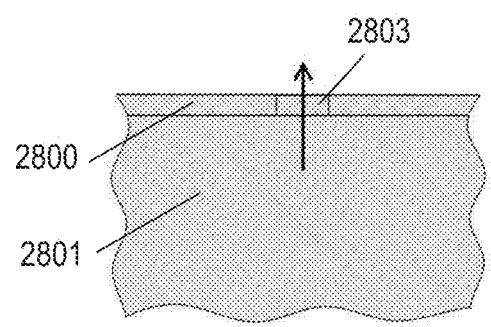

FIGS. 28-29 depict a sectional detail view of a portion of an airflow passageway of a whistle, bounded by passageway walls 2800 and 2801, with a vent 2803. When plug obstructor 2802 is present in vent 2803, air may be prevented from flowing through the vent 2803; when plug obstructor 2802 is absent, air may flow through the vent 2803, altering the allocation of airflow between vent 2803 and passageway leading to outlet tube 210A (depicted in FIG. 27).

Figure 30:
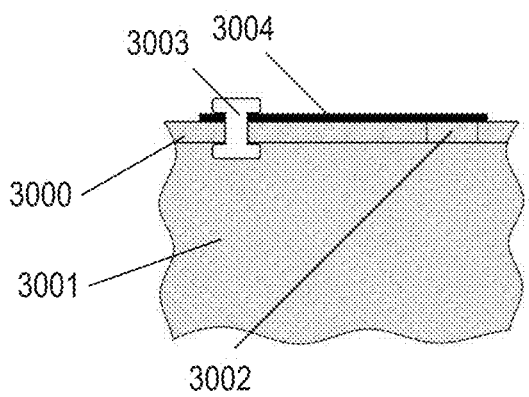
FIGS. 30 and 31 show a sectional detail view of a portion of a whistle's flow controller with a flex obstructor, operating under no-flow (FIG. 30) and high flow (FIG. 31) conditions, in accordance with one or more embodiments.
Figure 31:
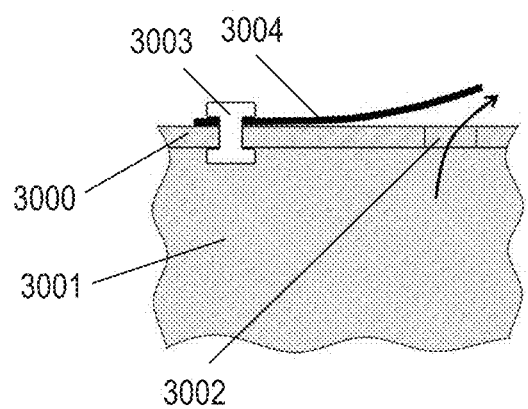

FIGS. 30-31 depict a sectional detail view of a portion of an airflow passageway in a whistle, bounded by passageway walls 3000 and 3001, with a vent 3002, and a combination spring/obstructor 3004 that is fastened to wall 3000 at one end by fastener 3003. When the pressure of airflow through the passageway and towards central cavity and outlet tube (neither depicted) is low, the combination spring/obstructor 3004 blocks vent 3002, as shown in FIG. 30. As pressure in the passageway increases, so too may the force exerted against spring/obstructor 3004 through vent 3002, causing spring/obstructor 3004 to flex in a manner that opens flow through vent 3002, thus dynamically altering the ratio of air flowing through the airflow passageway walled by 3000 and 3001 on the one hand, and air flowing through vent 3004 on the other.

Figure 32:
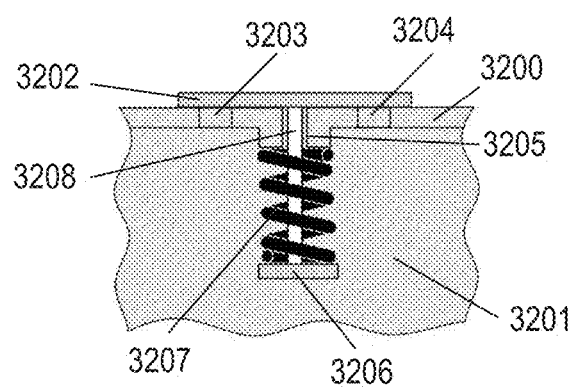
FIGS. 32 and 33 show a sectional detail view of a portion of a whistle's flow controller with a spring-loaded cover obstructor, operating under no-flow (FIG. 32) and high flow (FIG. 33) conditions, in accordance with one or more embodiments
Figure 33:
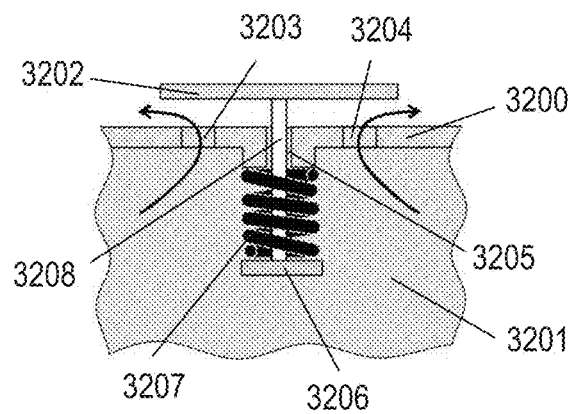

FIGS. 32-33 depict a sectional detail view of a portion of an airflow passageway in a whistle, bounded by passageway walls 3200 and 3201, with vents 3203 and 3204, covered by obstructor 3202, which may be attached to one end of a rod 3208 that is free to slide through hole 3205. At the other end of rod 3208 may be a spring stop 3206 that sandwiches a spring 3207 against a portion of wall 3200, such that obstructor 3202 is pulled by the force of the spring to cover vents 3203 and 3204. When the pressure of airflow through the passageway and towards central cavity and outlet tube (neither depicted) is low, obstructor 3202 blocks vents 3203 and 3204, as shown in FIG. 32. As pressure in the passageway increases, force on the regions of obstructor 3202 covering vents 3203 and 3204 increases, causing spring 3207 to compress and obstructor 3202 to rise, thus increasing airflow through vents 3203 and 3204, and dynamically altering the ratio of flow through the airflow passageway versus vents 3203 and 3204.

The flow control configurations illustrated in FIGS. 30-31 and 32-33 may be used in place of the flow control configurations illustrated in FIGS. 28-29 in a whistle similar to the whistle depicted in FIG. 27 to result in a whistle that dynamically allocates incoming airflow between vent and outlet tube exits in a continuous and dynamic way.

Figure 34:
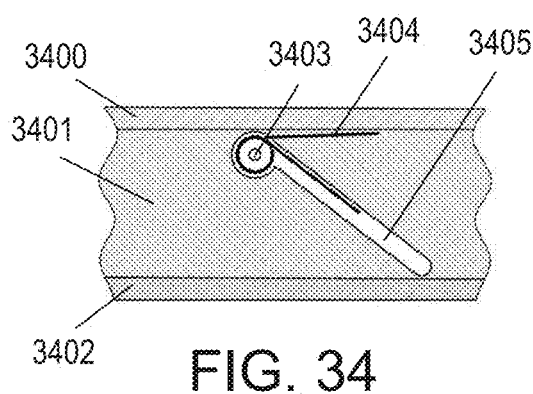
FIGS. 34 and 35 show a sectional detail view of a portion of a whistle's flow controller with a spring-loaded gate obstructor, operating under no-flow (FIG. 34) and high flow (FIG. 35) conditions, in accordance with one or more embodiments.
Figure 35:
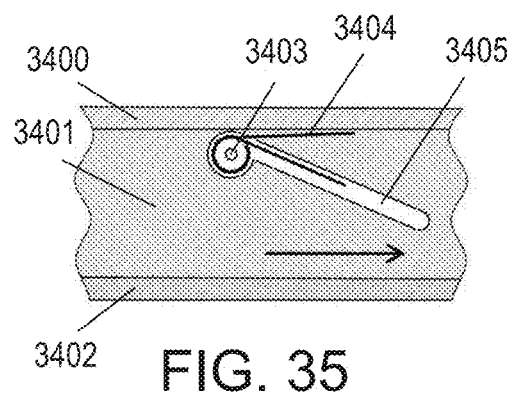

FIGS. 34-35 depict a sectional detail view of a portion of an airflow passageway of a whistle that leads to a vent (not depicted), bounded by passageway walls 3400, 3401 and 3402, with a gate obstructor 3405 that pivots about a hinge 3403 and is forced by torsional spring 3404 up against wall 3402 (in FIG. 34). When the pressure in the passageway to the left of gate obstructor 3405 is low, the gate obstructor 3405 may block air from flowing through the passageway towards the vent (not depicted). As the air pressure in the passageway to the left of gate obstructor 3405 rises (see FIG. 35), it may create a torque on the gate obstructor 3405 counteracting spring 3404, opening the passageway to airflow towards the vent, and altering the relative allocation of airflow through any whistle passageways or cavities in communication with the passageway depicted.

Figure 36:
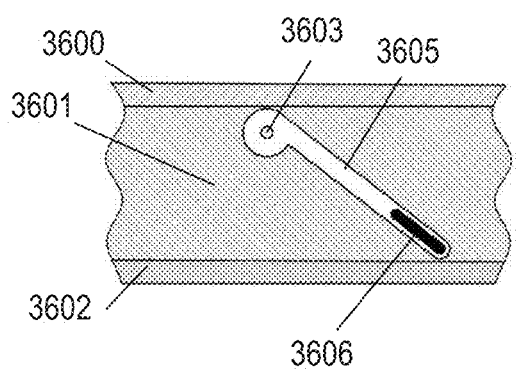
FIGS. 36 and 37 show a sectional detail view of a portion of a whistle's flow controller with a weighted gate obstructor, operating under no-flow (FIG. 36) and high flow (FIG. 37) conditions, in accordance with one or more embodiments.
Figure 37:
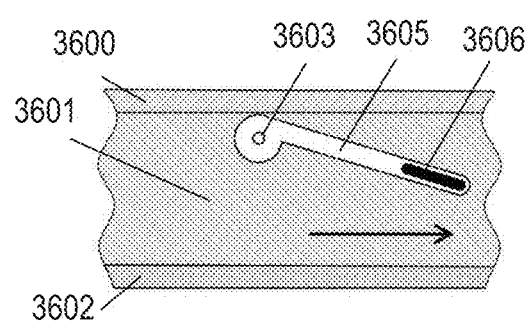

FIGS. 36-37 depict a sectional detail view of a portion of an airflow passageway of a whistle that leads to a vent (not depicted), bounded by an upper passageway wall 3600, a lower passageway wall 3602 and a far-side passageway wall 3601, with a gate obstructor 3605 that may pivot about a hinge 3603 and may contain a weight 3606 that exerts a gravitational force on obstructor 3605 towards bottom passageway wall 3602 (in FIG. 36). When the pressure in the passageway to the left of gate obstructor 3605 is low, the obstructor 3605 may block air from flowing through the passageway towards the vent (not depicted). As the air pressure in the passageway to the left of gate obstructor 3605 rises (see FIG. 37), it may create a torque on the obstructor 3605 counteracting the gravitational force exerted by the weight 3606, opening the passageway to airflow towards the vent, and altering the relative allocation of airflow through any whistle passageways or cavities in communication with the passageway depicted.

The above detailed description illustrates several examples for how flow may be controlled mechanically in various embodiments via the use of vents, obstructors and force-exerting elements. Other mechanical approaches are possible; for instance, through use of a duckbill valve or flip-cap valve.

Figure 38:
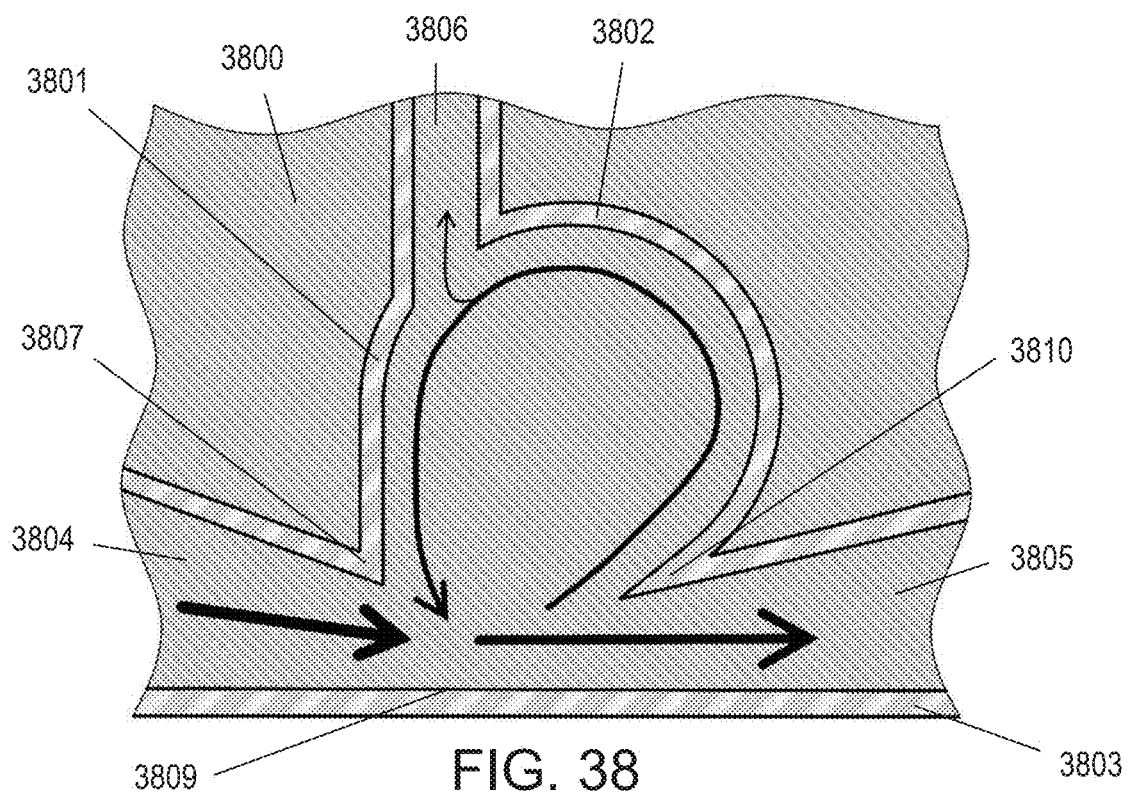
FIGS. 38 and 39 show a sectional detail view of a fluidic flow controller of a whistle, operating under low-flow (FIG. 38) and high-flow (FIG. 39) conditions, in accordance with one or more embodiments.
Figure 39:
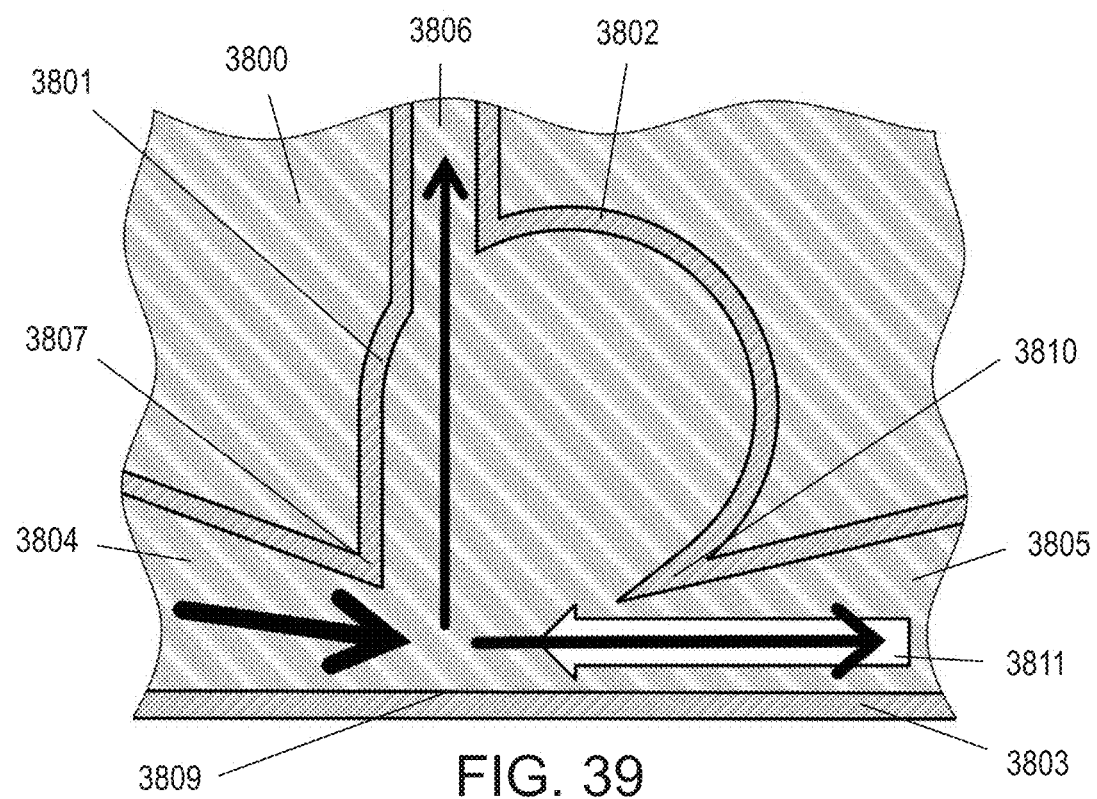

As previously introduced, a flow controller may alternatively function via non-mechanical, fluidic means. What follows is a detailed description of a fluidic flow controller that alters allocation of incoming airflow between two routes, in response to back pressure exerted by one of the routes:

FIGS. 38-39 depict a sectional detail view of a fluidic flow controller portion of a whistle. FIG. 38 depicts illustrative flow paths through the fluidic flow controller at a low flow rate, while FIG. 39 depicts illustrative flow paths through the same fluidic flow controller at a high flow rate. FIGS. 38-39 include: passageway walls 3800, 3801, 3802, 3803, an inflow passageway 3804, an outflow passageway 3805 leading toward a central cavity and outlet tube (not depicted), and an outflow passageway 3806 leading to a vent (not depicted).

Under low-flow conditions (See FIG. 38) air entering the flow controller through inflow passageway 3804 may encounter a sharp bend in wall 3807, and due to the prevailing direction of inflow (potentially together with Coanda adhesion to continuous surface 3809), airflow may tend to progress in the direction of outflow passageway 3805. As airflow traveling towards 3805 encounters the sharp-angled "splitter" (3810) portion of wall 3802, a portion of the airflow may not exit 3805, but instead may be directed by walls 3802 and 3801, wrapping around, and exerting further pressure on incoming airflow from inflow passageway 3804 to follow wall surface 3809 towards outflow passageway 3805. A portion of the airflow that does not exit outflow passageway 3805 may exit a second outflow passageway 3806, but this portion may be small relative to the portion that exits 3805, due to the arrangement of fluidic forces (e.g. inflow direction, downward force from a fluidic feedback loop, and potential Coanda adhesion to surface 3809). Because in FIG. 38 the flow rate exiting outflow passageway 3805 is low, back-pressure from the central cavity into outflow passageway 3805 may be negligible.

Under high-flow conditions (see FIG. 39), back-pressure from the central cavity (represented by arrow 3811) into outflow passageway 3805 may not be negligible as it may exert strong fluidic forces that interrupt the flow pattern depicted in of FIG. 38, such that the sharp angled "splitter" portion of wall 3802 no longer diverts flow cleanly into a fluidic feedback loop that ultimately exerts downward pressure, so incoming airflow is no longer pressed downward (i.e. towards the outflow passageway 3805 and away from the second outflow passageway 3806). As a result, there is a shift in the relative proportions of airflow exiting the outflow passageway 3805 and the second outflow passageway 3806, with proportionally more airflow exiting the second outflow passageway 3806 towards the vent under high-flow conditions than under low-flow conditions. Thus, a flow controller without a mechanical mechanism may dynamically allocate flow between two outflow passageways, in response to back-pressure from one of the outflow passageways. It is notable that the approach presented in FIGS. 38 and 39 comprises geometry that can be mirrored, repeated, or revolved (revolved, in the sense of revolving a solid in a solid-modeling program, such as Solid Works) around or about an axis extending from the inflow passageway 3804 to the outflow passageway 3805, an axis which may be substantially parallel to the passageway wall 3803, with a potential advantage of intensifying or altering the controlling behavior of the flow controller.

Returning to a higher-level discussion of alternate embodiments, an aspect of one or more embodiments is that real-time feedback may be provided on a display of the device. In some embodiments, real-time feedback may include information presented as text (e.g. a numeric representation for current flow rate, etc.). In some embodiments, real-time feedback may include graphical representations, which may be animated (e.g. a continuously-updating bar graph representing flow rate, etc.). In some embodiments, real-time feedback may include animated responses (e.g. a pinwheel that rotates, apparently in response to a user's forced exhalation through a whistle, etc.).

In some embodiments, real-time feedback may include varying one or more attributes of a displayed representation (e.g. shape, color, opacity, transparency, scale, aspect ratio, velocity, acceleration, angular velocity, angular acceleration, direction, animation speed, etc.), or points of view (e.g. camera speed moving from a first-person point of view through a scene, degree of elevation looking down on a scene, frame-rate, frame-brightness, etc.) with the value of a variable being updated in response to a user's exhalation through a whistle (e.g. variables corresponding to fundamental audio frequency, audio amplitude, user's expiratory flow rate, etc.). There are various ways in which an attribute of a displayed representation or point of view may vary, continuously or discretely, with a variable being updated in response to a user's exhalation through a whistle; for example, such a relationship between an attribute and a variable may be linear, exponential, logarithmic, a step function or some other function. In one or more embodiments, a pinwheel presented on a display of the mobile device may begin to spin at a speed proportional to the highest real-time expiratory flow rate encountered so far during the course of a user's expiratory maneuver through a whistle. In one or more embodiments, a puffer fish presented on the display of the mobile digital device may expand to a size proportional to a peak fundamental frequency received by the mobile device from the whistle. Varying perceptible attributes of displayed representations or viewpoints in near real-time with variable being updated in response to a user's exhalation through a whistle may support an enhanced sense that the whistle is directly "connected" to a visualization, story, game, gag or puzzle element displayed by the mobile device, and thereby increase a user's sense of immersion and engagement.

Representations presented on display(s) of the device before, during and/or after a measurement trial may be arranged so as to include or support a story, gag, game or puzzle, with an advantage of supporting immersion and engagement. In some embodiments, the user may have a role to play in such a story, gag, game or puzzle by blowing the whistle, such as the role of a hero or a villain. For example, a best-of-three spirometric measurement trial session may be framed as a chance to play the big bad wolf in the story of the three little pigs; first blowing down a house of straw; next blowing down the house of twigs, and finally listening to the relieved exuberance (or taunts) of the three little pigs hiding safely in a house of brick.

According to some embodiments, the story, game, gag or puzzle may begin and end with a single flow measurement trial. In some embodiments, the story, game, gag or puzzle may begin and end with one flow measurement "session" (e.g. a set of measurement trial(s), with no interstitial period greater than a certain maximum duration, such as 5 minutes, 10 minutes, an hour, etc.). In some embodiments, the story, game, gag or puzzle may persist across measurement trials or sessions. In some embodiments, the story, game, gag or puzzle may be episodic (e.g. may have recurrent character(s), plot elements, scenes, or themes, etc.). In some embodiments, there may be multiple stories, games, gags or puzzles—potentially with interwoven and/or intersecting aspects. In some embodiments, a story, game, gag or puzzle may be selectable by a user out of a set of stories, games, gags or puzzles. In some embodiments, a story, game, gag or puzzle may be selectable by an algorithm, or an algorithm in conjunction with input from one or more people, and/or information about a user or a user's cultural context (e.g. selection based on a pseudo-random number, a user's previous experience of the system, a user's previous selection, a user's "favorites", other user's favorites or recommendations, whether or not it is the user's birthday or a holiday, etc.). In some embodiments, a story, game, gag or puzzle may be pseudo-randomly or randomly selected.

According to some embodiments, the supported stories, games, gags or puzzles may include (or connect to) a system for managing, administering or presenting rewards, which may include extrinsic or intrinsic rewards. For instance, a user that performs their recommended flow measurements regularly over a period of time may be rewarded with a new set of stories, games, gags or puzzles to experience (intrinsic rewards), or extrinsic rewards such as virtual badges, points, etc., or extended real-world permissions (e.g. additional screen or tv time, extra dessert, extra time with friends, etc.). According to some embodiments, rewards presented may be social in nature; for instance, through representations presented on a display of the device, the method may communicate to a user that they are not alone in conducting regular spirometric measurements, that there are others in the same boat, conducting their own spirometric measurements with varying degrees of regularity. In some embodiments, the method may present periodic messages of encouragement from friends, family, peers, other users of other whistles, total strangers or virtual characters, to convey a sense that the user is socially supported within their personal spirometric regimen.

In some embodiments, flow measurement trials or sessions, and/or accompanying presentation of stories, games, gags or puzzles may be rate-limited (e.g. only 3 trials or one trial session permitted every 3, 6, 12 or 24 hours, etc.), so as to promote a user's long-term interest/engagement, and/or to reinforce a regular cadence of usage.

In some embodiments, the whistle may include one or more secondary acoustic transducers that produce acoustic emissions in response to fluid flow (e.g. a Galton whistle, Hartmann whistle, edge tone whistle, hole tone whistle, jet-edge whistle, pea-whistle, Class I, II or III aerodynamic whistle, fluidic oscillator, siren, free reed, bell, clapper, etc.), with an advantage of supporting sonic and/or ultrasonic communication of additional information about a user's usage of the whistle. For example, a secondary sound producing structure may be incorporated and or calibrated so as to communicate to a human (and/or mobile device) when a forced exhalation through the whistle has begun or ended, or when the whistle is operating outside of its intended or effective measurement range. In some embodiments, such a secondary acoustic transducer may be included along a "spill-over" or "pressure relief" route through the whistle.

In various embodiments, in response to a range of flow rates producible by a human user, the secondary acoustic transducer may produce: a substantially constant frequency (e.g., fundamental frequency, etc.), a predictably variable frequency, an unpredictably variable frequency, a substantially constant frequency over one portion of the range and a variable frequency over another portion of the range, a frequency that jumps one or more octaves, or a constant frequency that is modulated by a variable frequency. In some embodiments, the whistle may include a plurality of types of acoustic transducers, each acoustic transducer having one or more parameters that vary with airflow rate.

In some embodiments, a secondary acoustic transducer may be positioned so as to accept a portion of any expiratory airflow exiting one or more of a user's nostrils, and produce identifiable acoustic emissions in response. Such a structure, positioned so as to convert flow from a user's nose into acoustic emissions, may be referred to herein as a "nose whistle". In some embodiments, the nose whistle is audible, with an advantage that it may provide feedback to a user. In some embodiments, the nose whistle is ultrasonic, or nearly ultrasonic, with an advantage that such a whistle can be made from less material in a smaller form-factor. In some embodiments, the method determines whether or not the identifiable acoustic emission from the nose whistle has occurred during a trial, and responds accordingly (e.g. communicating to the user that measurement accuracy is compromised if expiratory airflow passes through the nose, etc.). In this way, an additional source of error for flow measurement may be conveniently addressed. In some embodiments, a secondary acoustic transducer may be positioned so as to accept a portion of expiratory airflow exiting a user's mouth.

In one or more embodiments, multiple values for a respiratory measurement may be displayed on a display of the mobile device, or another display. In some embodiments, for example, the "current" and "best" peak flow measurement for a flow measurement session may be displayed on the display of the mobile device. In some embodiments, a graph depicting measurement of a given metric (e.g. PEFR, $FEV_1$ etc.) over time may be displayed on the display of the mobile device or another device (e.g. a parent's or doctor's computer). In some embodiments, the timescale of graphs may be changed, to facilitate exploration of trends over multiple timescales. In one or more embodiments, correlations may be made between respiratory metrics and external variables including environmental variables (e.g. particulate matter count, pollen count, changes in the seasons, etc.), and subsequently displayed on a display of the mobile device, or another display, whereby a user, parent, doctor, etc. may more easily explore potential relationships between a user's respiratory health and external variables.

In one or more embodiments, a human or machine readable identifier of a whistle may include a frequency or frequency range, a feature of a frequency spectrum, or a feature within a sequence of frequency spectra emitted by the whistle, with an advantage that a whistle may be identified by the method through blowing the whistle. Such identifiers of the whistle are further illustrative examples of dynamic identifiers, introduced previously.

According to one or more embodiments, the mouthpiece of the whistle may be a removable, replaceable mouthpiece, with an advantage of supporting hygienic shared usage. The mouthpiece may be disposable, and may be made of a compostable or recyclable material.

According to one or more embodiments, the outlet tube of the whistle may be part of, or comprise a snap-in, press-fit, or screw-in substitutable component of the whistle, so that different outlet tubes of different geometries (i.e. different internal diameters, lengths, etc.) may be attached to or detached from the whistle, with advantages such as altering the a characteristic of the whistle (e.g. a relationship between airflow rate and frequency, etc.).

According to one or more embodiments, the flow controller may include a pressure relief valve or spill-over valve. According to one or more embodiments, the pressure relief valve or spill-over valve may limit or reduce back pressure (and/or airflow resistance) presented by the whistle to a user's respiratory system while the user is using the whistle. According to one or more embodiments, the pressure relief valve or spill-over valve may limit or reduce the maximum back pressure and/or airflow resistance of the whistle over a given flow rate range. For example, a maximum resistance to flow may be kept below a particular value (e.g., 0.15, 0.20, 0.35, 0.5, 0.75, etc. kPa/L/min) over a measurement range extending from a particular value (e.g. 15, 30, 60, 90, etc. L/min), to a particular value (e.g. 300, 500, 800, 900, etc. L/min).

According to one or more embodiments, a transition between a main cavity of the whistle and an outlet tube may be continuous, stepped or otherwise discontinuous, with advantages of balancing mechanical, acoustic and interaction design tradeoffs mentioned at various points within this document.

An aspect of one or more embodiments may be to encourage users to become more active participants in their own care, and/or to become more aware of their own respiratory health. As such, in one or more embodiments, the method may include prompting the user to estimate, guess or predict a result of a measurement (e.g. a respiratory parameter, such as PEFR, $FEV_1$, etc.) before or after the measurement has occurred, and before presenting the actual result of a measurement. In one or more embodiments, the method may further include receiving the user's estimate, guess or prediction from the user via a means of user input, such as a touch-screen, button or microphone of the mobile digital device. Receiving the user's estimate, guess or prediction may occur at various granularities, and in various forms. For example, a prediction may be requested and/or received through an utterance such as "Great", "Good", "Ok", "Poor"; a color (e.g. red/yellow/green, etc.), or via symbolic numeric representations of measurement values, such as PEFR, etc.) The method may further include presenting the user's estimate, guess or prediction via a display of the mobile digital device (e.g., as a numeric value on a screen, etc.). The method may further include displaying the user's estimate, guess or prediction in conjunction with a result of a measurement, potentially with an indication of the difference between estimate and actual measurement (e.g. numeric representation of percent error, etc.). The method may further include storing the user's estimate, guess or prediction, locally, in the memory of the mobile digital device, or remotely, in the memory of a networked storage resource. The method may further display one or more representations of a reward (e.g. virtual badge, points, rewarding sound, etc.) as a user's estimations improve over time (i.e., grow closer, on average, to actual measured values), as a means of recognizing and/or rewarding the user's improved estimation ability and/or awareness of their own respiratory health. User prediction prior to respiratory measurement performance may result in improved perception of lung function, as found and reported by Feldman, et al. in the publication *Thorax* 2012; 67, pages 1040-1045.

In various embodiments, one or more aspects of the whistle (e.g. a mechanical flow controller, etc.) may be adjusted for purposes including calibration. In various embodiments, adjustments may comprise mechanical adjustments, such as tightening a screw, altering the position of an element, or altering the relative position of two elements. In various embodiments, adjustments may comprise automated adjustments, for instance, laser-trimming a weight element or a spring, to decrease a required activation force.

In various embodiments, the whistle may be a pea-less whistle; i.e. it may contain no captive pea, ball or roller element within a chamber that moves in response to a user's expiratory airflow in a way that interrupts acoustic emissions.

In various embodiments, the mobile device may be configured to present a training mode that illustrates or introduces how to perform a spirometric measurement. Such a training mode may present audio/visual instructions that differ or are more extensive than are presented during ordinary usage of the system. Such a training mode may present rewards (e.g. audible rewards, points, etc.) that differ or are more extensive than are presented during ordinary usage of the system. Such a training mode may involve presenting a representation of a teacher or host character, (which may be animated, pictorial, video, etc.), and may illustrate how expiratory maneuvers are performed, or are not performed, and/or how the system operates. Such a training mode may involve presenting a representation of a user (which may be animated, pictorial, video, etc.); this user may illustrate how expiratory maneuvers may be performed, and/or how the system operates. In various embodiments, the mobile device may be configured to present an on-boarding mode, in which data such as a user's name, age, height, etc. are initially collected and/or stored, and/or encouragement or congratulations provided. In some embodiments, the mobile device may be configured to present a demonstration mode, with access to a limited/modified subset of functionality. For instance, a demonstration mode of the mobile device may work with any whistle (i.e. not perform a whistle validation step), but may not report or display respiratory measurements, or may only present a limited sub-set of entertaining visualizations in response to a user blowing the whistle during a trial. In some embodiments, such data may be collected via a user input means of the mobile device.

An aspect of one or more embodiments is that the whistle may produce an acoustic emission with a frequency that varies linearly with airflow rate, whereby the correlation for a given whistle design and measurement error rates may be easily determined, and the correlation may be represented simply in software, with minimal memory requirements.

An aspect of one or more embodiments is that the whistle may produce an acoustic emission with a frequency that varies predictably but nonlinearly (e.g. piece-wise linearly, logarithmically, etc.) with airflow rate, such that small changes at low flow rates as well as large changes at high flow rates are both accommodated within the effective measurement range of the system. In one or more embodiments, the whistle may have a correlation between acoustic frequency and airflow rate such that acoustic frequency may be a substantially continuously increasing function of airflow rate, with a higher slope for lower airflow rates and a lower slope for higher airflow rates, over a measurement range producible by a population of human users (e.g. 0.83 L/sec-11.67 L/sec, 1 L/sec-13.33 L/sec, etc. in the case of a measurement range for peak airflow rate).

In one or more embodiments, the frequency range produced by the whistle in response to airflow rates producible by a population of human users may fall within a specific range determined to be advantageous according to a combination of concerns related to aesthetics, whistle physics, human hearing, the constraints of mobile digital devices and microphones, and the constraints of wireless networks such as digital telephony, GSM, or CDMA; for example: 0 Hz-3.1 kHz; 0 Hz-2.0 kHz; 100 Hz-2.0 kHz; 100 Hz-3.1 kHz; 300 Hz-3.1 kHz; 0 Hz-4.0 kHz; 0 Hz-22.1 kHz; etc.

Figure 40:
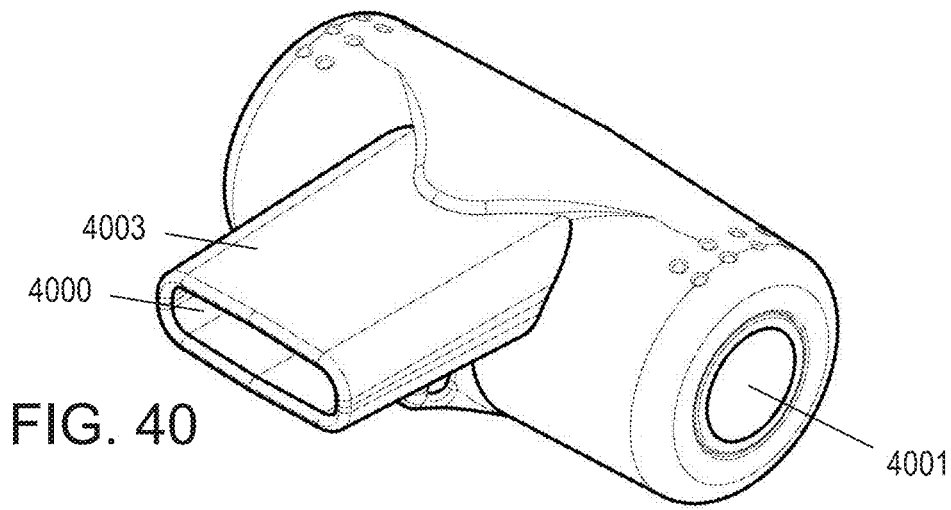
FIG. 40 shows a perspective view of a whistle with two outlets, in accordance with one or more embodiments.
Figure 41:
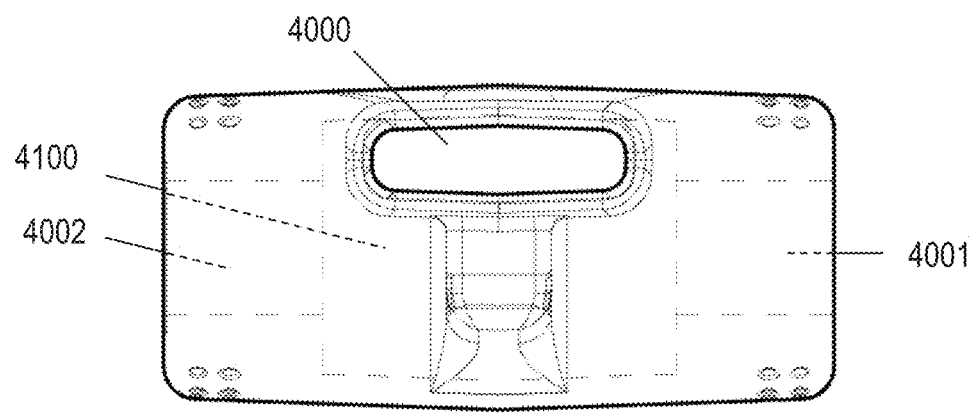
FIG. 41 shows a front view of a whistle with two outlets, in accordance with one or more embodiments.
Figure 42:
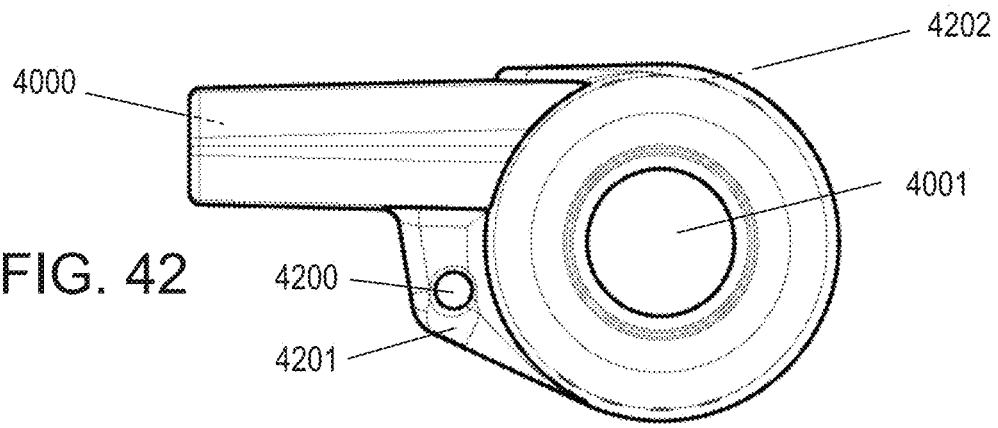
FIG. 42 shows a side view of a whistle with two outlets, in accordance with one or more embodiments.

Returning to a detailed discussion of various embodiments of the whistle, FIGS. 40-42 depict perspective, front and side views, respectively, of a whistle embodiment including a mouthpiece 4003, an inlet passageway 4000 that transitions to a central cavity 4100 via airflow guide wall portion 4202, and a pair of recessed outlet tubes 4001, 4002, extending from opposite ends of a (common) central cavity 4100. The whistle may further include a stand 4201, which enables the whistle to be placed on a flat surface without the mouthpiece touching the surface. Stand 4200 may include a hole, usable for a keyring, lanyard or other connector. When a user blows through mouthpiece 4003, expiratory airflow may enter inlet passageway 4000, and be guided into a swirling vortex within central cavity 4100 by airflow guide wall portion 4202, a vortex which exits the whistle through recessed outlet tubes 4001 and 4002, thus producing an acoustic emission or the whistle's characteristic sound.

Figure 43:
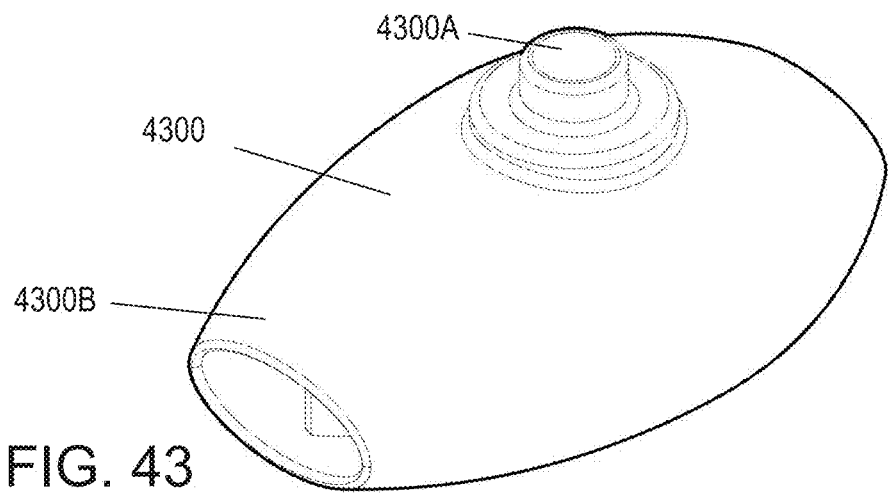
FIG. 43 shows a perspective view of a whistle with a mechanical flow controller, in accordance with one or more embodiments.
Figure 44:
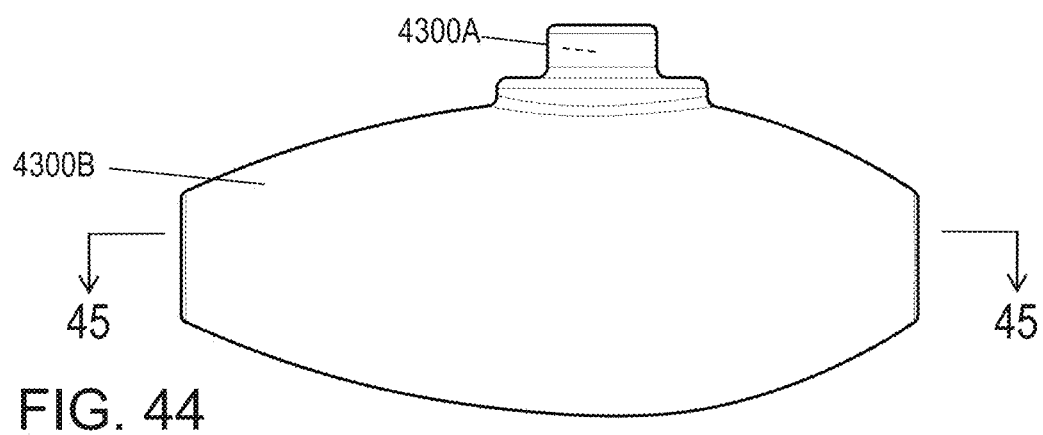
FIG. 44 shows a side view of a whistle with a mechanical flow controller, in accordance with one or more embodiments.
Figure 45:
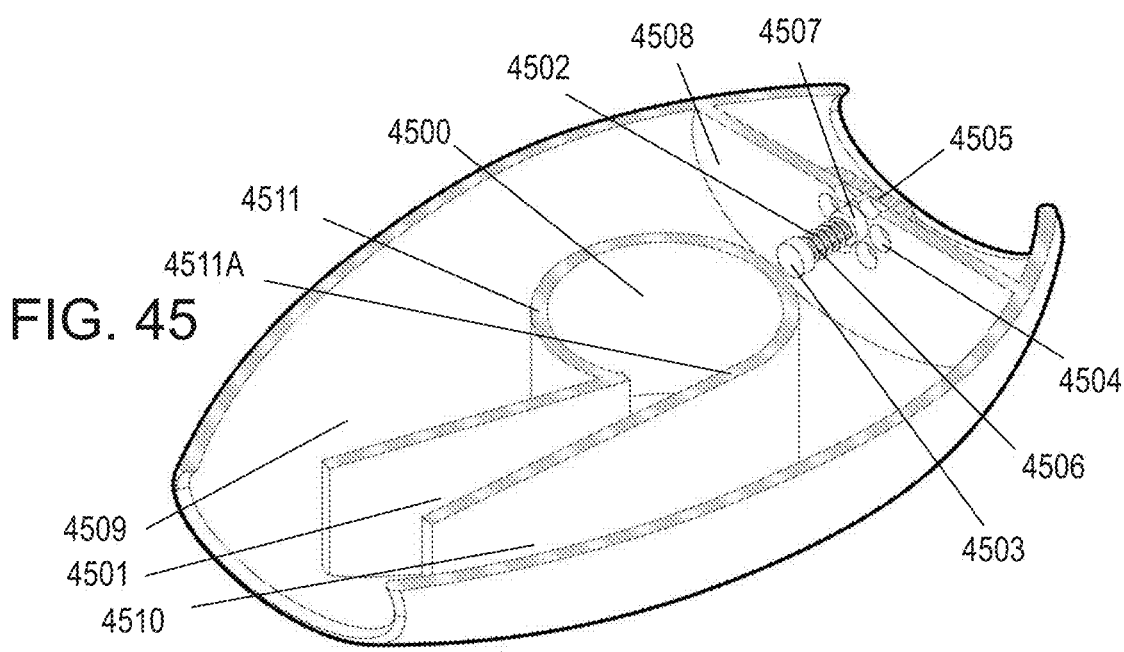
FIG. 45 shows a sectional perspective view of a whistle with a mechanical flow controller, in accordance with one or more embodiments.

FIGS. 43-45 depict perspective, side, and sectional perspective views, respectively, of a whistle embodiment with a flow controller similar to the flow controller shown in FIGS. 32-33. The whistle of FIGS. 43-45 includes a mouthpiece 4300B, a recessed inlet passageway 4501, a central cavity 4500 circumscribed by passageway wall 4511 comprising an airflow guide portion 4511A, an outlet tube 4300A, and a housing 4300. The whistle of FIGS. 43-45 may further include a flow controller, comprising a passageway wall 4508 with several vent holes 4504 that are oriented in a ring around a bearing 4507, through which a rod 4506 may be free to move axially. At one end of rod 4506 is a circular obstructor, 4505, that, in its closed position, may block airflow through vent holes 4504. A spring, 4502, positioned between a spring stop 4503 and bearing 4507, and around rod 4506, may exert a force that pulls obstructor 4505 toward passageway wall 4508, thus limiting airflow through vent holes 4504. To either side of recessed inlet passageway 4501 are side passageways 4509 and 4510, which may converge near flow controller passageway wall 4508.

Before a user begins to exhale through mouthpiece 4300B, obstructor 4505 may be in its closed position, due to the force exerted by spring 4502, and so may prevent airflow through vent holes 4504. As a user begins to exhale through mouthpiece 4300B, expiratory airflow may enter the whistle, pass into inlet passageway 4501, and be guided into a swirling vortex in central cavity 4500 by airflow guide wall portion 4501. The vortex may exit outlet tube 4300A, thus producing the whistle's characteristic sound. As a user continues to exhale through mouthpiece 4300B with increasing airflow, an increasing amount of airflow resistance may develop along the airflow path leading from inlet passageway 4501 through outlet tube 4300A; this increasing amount of airflow resistance may result in an increase in back-pressure at the entrance of inlet passageway 4501. This increase in back-pressure at the entrance of inlet passageway 4501 may, in turn, result in increasing pressure within side passageways 4509 and 4510, which may produce an increasing outward pressure on circular obstructor 4505, through vent holes 4504. If the user exhales forcefully enough, the outward pressure on circular obstructor 4505 through vent holes 4504 may causes spring 4502 to compress, which may enable obstructor 4505 to move outward, and may allow or increase airflow through vent holes 4504; the more pressure on circular obstructor 4505, the more air may flow through vent holes 4504. In this way, the whistle's flow controller (i.e. 4502, 4503, 4504, 4505, 4506, 4507, 4508) may dynamically allocate proportions of a user's expiratory airflow into the whistle between outlet tube 4300A and vent holes 4504, and may thereby: a) limit back-pressure exerted on a user's respiratory system during measurement, b) extend the effective measurement range of the whistle, and c) improve the audibility/detectability of acoustic emissions at low flow rates while decreasing the probability of uncomfortable or painful acoustic intensities and/or frequencies at high flow rates.

Figure 46:
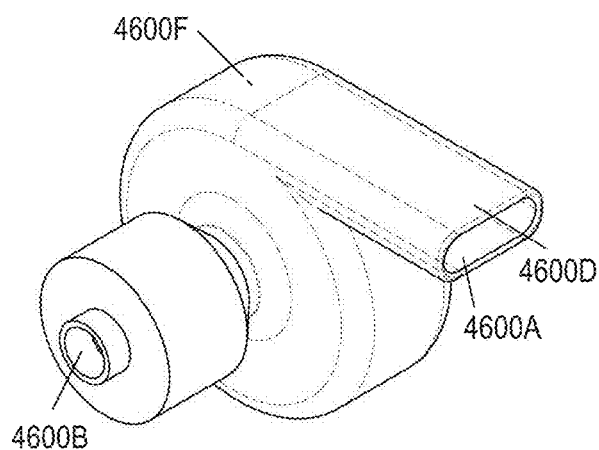
FIG. 46 shows a perspective view of a whistle with a fluidic flow controller, in accordance with one or more embodiments.
Figure 47:
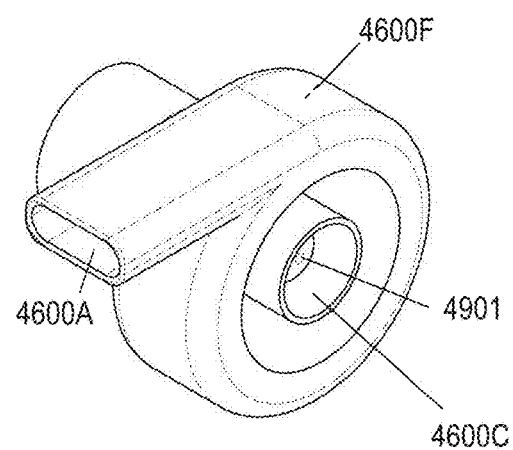
FIG. 47 shows a perspective view of a whistle with a fluidic flow controller, in accordance with one or more embodiments.
Figure 48:
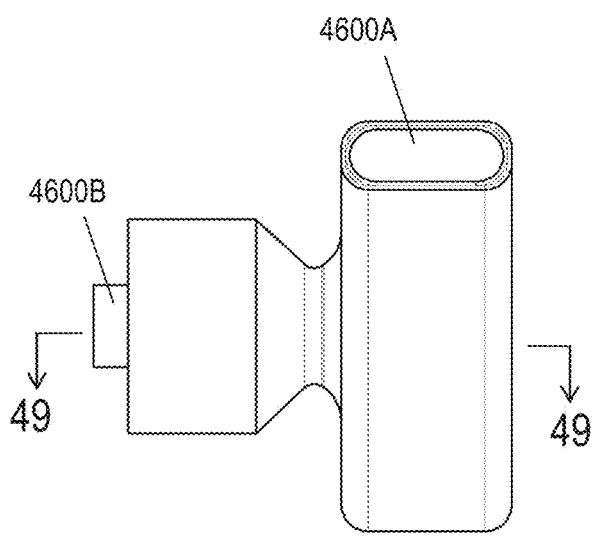
FIG. 48 shows a front view of a whistle with a fluidic flow controller, in accordance with one or more embodiments.
Figure 49:
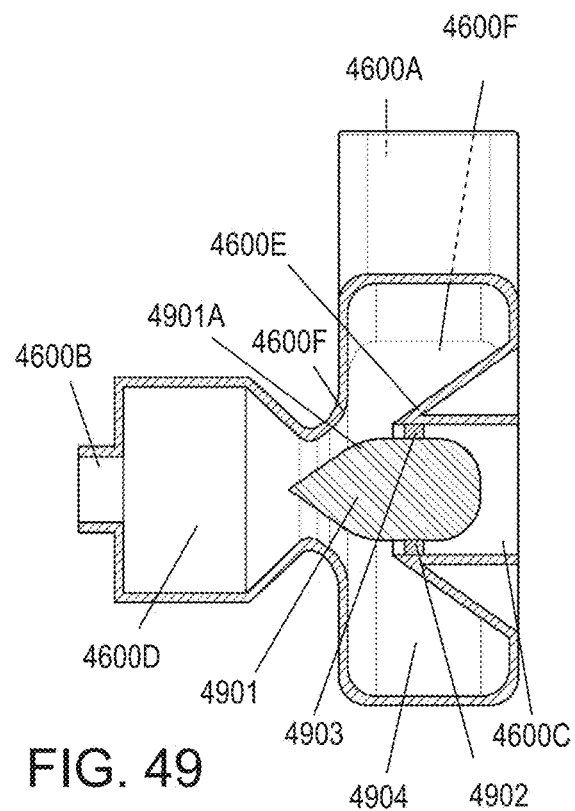
FIG. 49 shows a sectional bottom view of a whistle with a fluidic flow controller, in accordance with one or more embodiments.
Figure 50:
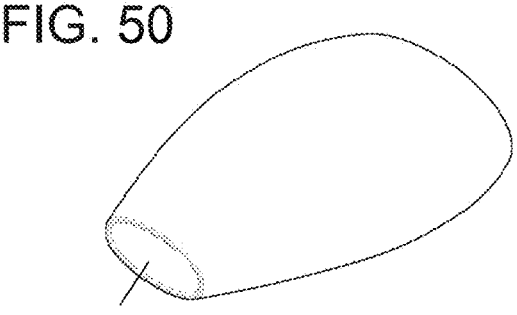
FIG. 50 shows a perspective view of a whistle with a mechanical flow controller, in accordance with one or more embodiments.
Figure 51:
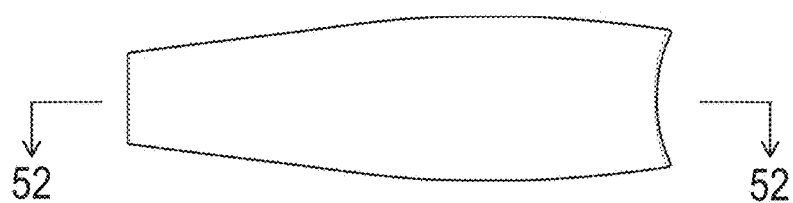
FIG. 51 shows a side view of the whistle illustrated in FIG. 50, in accordance with one or more embodiments.

FIGS. 46-49 depict an engineering prototype for a whistle embodiment having a fluidic flow controller; a controller which may dynamically limit back pressure on a user's respiratory system without mechanism, i.e. solely through fluidic interactions and static structure. FIGS. 46 and 47 depict perspective views of the whistle oriented, respectively, to portray the whistle's sound-emitting outlet tube 4600B, and vent exit tube 4600C. FIG. 48 depicts a front view of the whistle (i.e. mouthpiece inlet passageway 4600A facing the reader) which indicates the cross section of FIG. 49: A sectional view from the bottom of the whistle. This whistle comprises a mouthpiece 4600D having inlet passageway 4600A which transitions into a ring-like central cavity 4904, via an airflow guide surface region 4600F. Central cavity 4904 may be defined on one side by an inward-slanted sidewall-portion 4600E that meets vent exit tube 4600C at a sharp angle, and on the other side, by an outward-slanted sidewall portion 4600F that leads to a secondary central cavity 4600D with an outlet tube 4600B. A set of radially distributed struts (4902, 4903) suspend a teardrop element 4901 with continuous transitional surface 4901A at the center of ring-like central cavity 4904 and vent tube 4600C. Outlet tube 4600B, secondary cavity 4600D, central cavity 4904, teardrop-like element 4901, radially distributed struts 4902 and 4903, and vent exit tube 4600C may share a common central axis. Space between the tapered portion of teardrop element 4901 and outward-slanted sidewall portion 4600F may create a path from central cavity 4904 to secondary central cavity 4600D. Space between teardrop element 4901 and vent exit tube 4600C may create a path extending from central cavity 4904, through the radially distributed struts 4902, 4903 and out vent exit tube 4600C.

When a user exhales through the whistle depicted by FIGS. 46-49, expiratory airflow may enter inlet passageway 4600A, and be guided by transitional airflow guide surface region 4600F into an inward-spiraling motion within ring-like central cavity 4904. A portion of inward-spiraling airflow may pass from ring-like central cavity 4904, through the space between outward-slanted sidewall portion 4600F and the tapered portion of teardrop element 4901, and into secondary central cavity 4600D, where a vortex may be formed. The vortex may subsequently exit outlet tube 4600B, whereby the whistle's characteristic sound may be produced.

As airflow within ring-like central cavity 4904 spirals towards the central axis (i.e. towards possible exit paths 4600B and 4600C), the inward angle of sidewall portion 4600E in conjunction with the outward angle and smoothly continuous transitional surface of sidewall portion 4600F may cause airflow to prefer the airflow path towards outlet tube 4600B over the airflow path towards vent exit tube 4600C. This preferentiality may be the result of one or more of: Coanda adhesion to surface 4901A from airflow passing by 4600E, centrifugal force pushing airflow towards 4600F, and the relative dimensions of 4901, 4600C and 4600F.

At low airflow rates, airflow past 4600E and 4901A towards outlet tube 4600B may have the effect of drawing additional airflow in from exit 4600C, thus resulting in the airflow exiting outlet tube 4600B being greater than the airflow entering 4600A. This may have the beneficial effect of bolstering acoustic emissions and ensuring robust signal transmission to the mobile device at low airflow rates.

As a user's expiratory airflow into the whistle increases, however, airflow resistance may begin to build within secondary central cavity 4600D, creating a back-pressure resulting in the exit path through outlet 4600B becoming less and less attractive to airflow, relative to the exit path through vent exit tube 4600C. As a result, an increasing proportion of the user's expiratory airflow may exit vent exit tube 4600C. Thus, the whistle may dynamically allocate relative proportions of user's expiratory airflow between two exits (outlet tube 4600B, and vent exit tube 4600C) through fluidic means, and may thereby: a) limit back-pressure exerted on a user's respiratory system during measurement, b) extend the effective measurement range of the whistle, c) improve the audibility/detectability of acoustic emissions at low flow rates while decreasing the probability of uncomfortable or painful acoustic intensities and/or frequencies at high flow rates, and d) reduce manufacturing cost, need for calibration and possibility of breakage, since no mechanism is required.

Many variations of the whistle embodiment presented in FIGS. 46-49 are possible. For example, instead of a cylindrical secondary central cavity 4600D, a combination of one or more convergent and/or divergent stages may be employed. In some embodiments, this might obviate the need for a dedicated cylindrical outlet tube. Dimensions may be varied, as could the number of struts to the flow-controlling aspect of the whistle, or other aspects. The struts may be shaped or oriented so as to either: a) enable the vent exit to function as a secondary sound source, potentially complementing the first aesthetically or serving as a signal (e.g. indicating that too much airflow is passing through the vent, etc.) or b) reduce or eliminate the vent's acoustic impact. The vent exit tube may be tapered inward, to facilitate cleaning of concave crevices. Aesthetic fillets and or chamfers may be added for comfort and cleanability. Portions of the whistle could be shaped or enclosed such that the outlet tube faces upwards rather than sideways while in use. Physically independent parts may be combined, or portions of a part could be separated into different functional parts. These and many other variations may beneficially serve to balance tradeoffs such as manufacturability, airflow resistance, sound quality and/or whistle size, without departing from the spirit of the invention.

Returning to a detailed discussion of various embodiments of the whistle, FIGS. 50-52B depict perspective, side, and top-sectional views, respectively, of a whistle embodiment with a mechanical flow controller operating on the same principle as the flow controller with the flex obstructor shown in FIGS. 30-31. The whistle of FIGS. 50-52B may include an inlet 202, an airflow guide 204, a hollow main tube 206, an outlet tube 210, and an outlet 212. The airflow guide 204 may be situated within the whistle's hollow main tube 206 between inlet 202 and outlet 212. Vanes 204C of airflow guide 204, together with the inner wall of the main tube 206, define several airflow passageways or channels. The whistle comprises a housing 5201 with an internal wall 5201A, which supports main tube 206, as well as a pair of umbrella valve flex obstructors 5204, which cover a plurality of vent holes 5202. The internal wall 5201A, umbrella valve flex obstructors 5204 and vent holes 5202 together may form the whistle's flow controller.

Figure 52A:
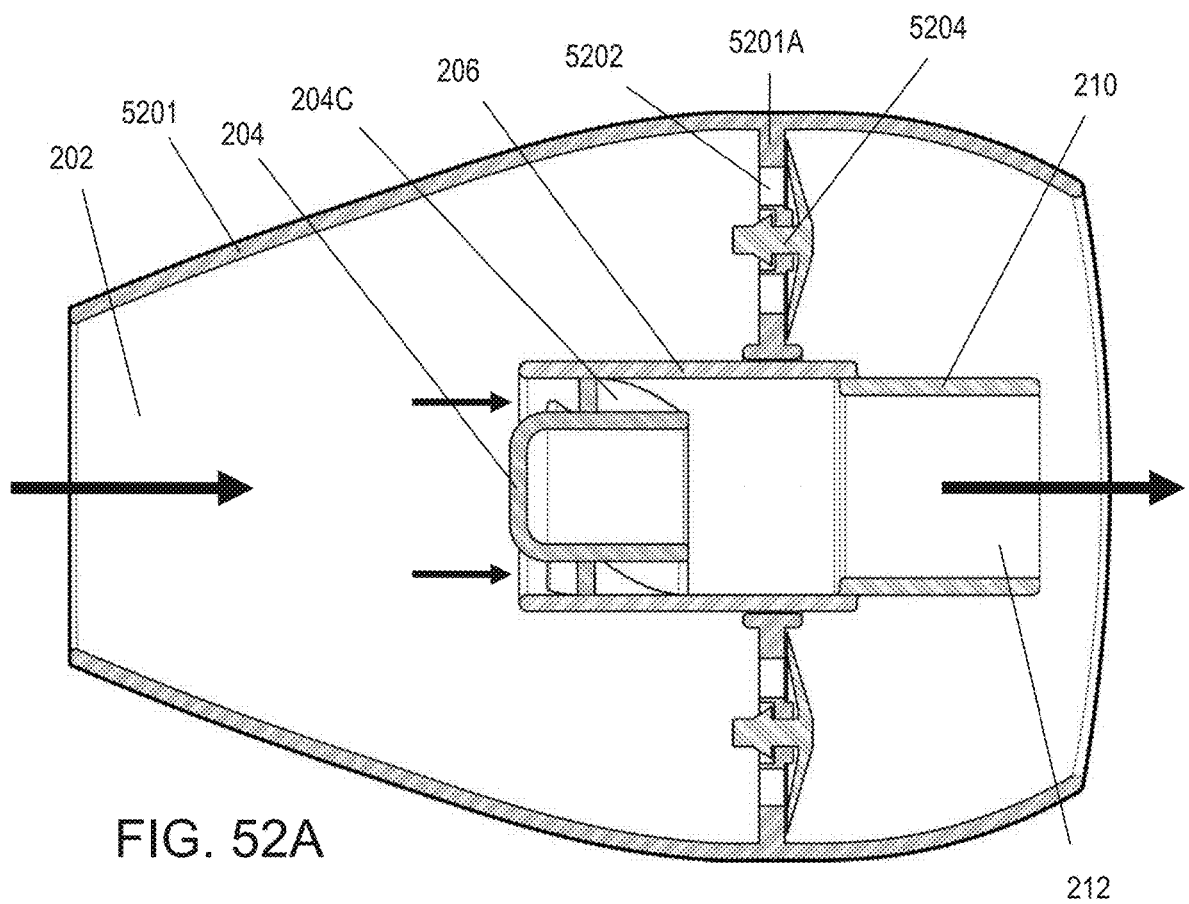
FIG. 52A shows a sectional top view of the whistle illustrated in FIG. 50, in accordance with one or more embodiments.
Figure 52B:
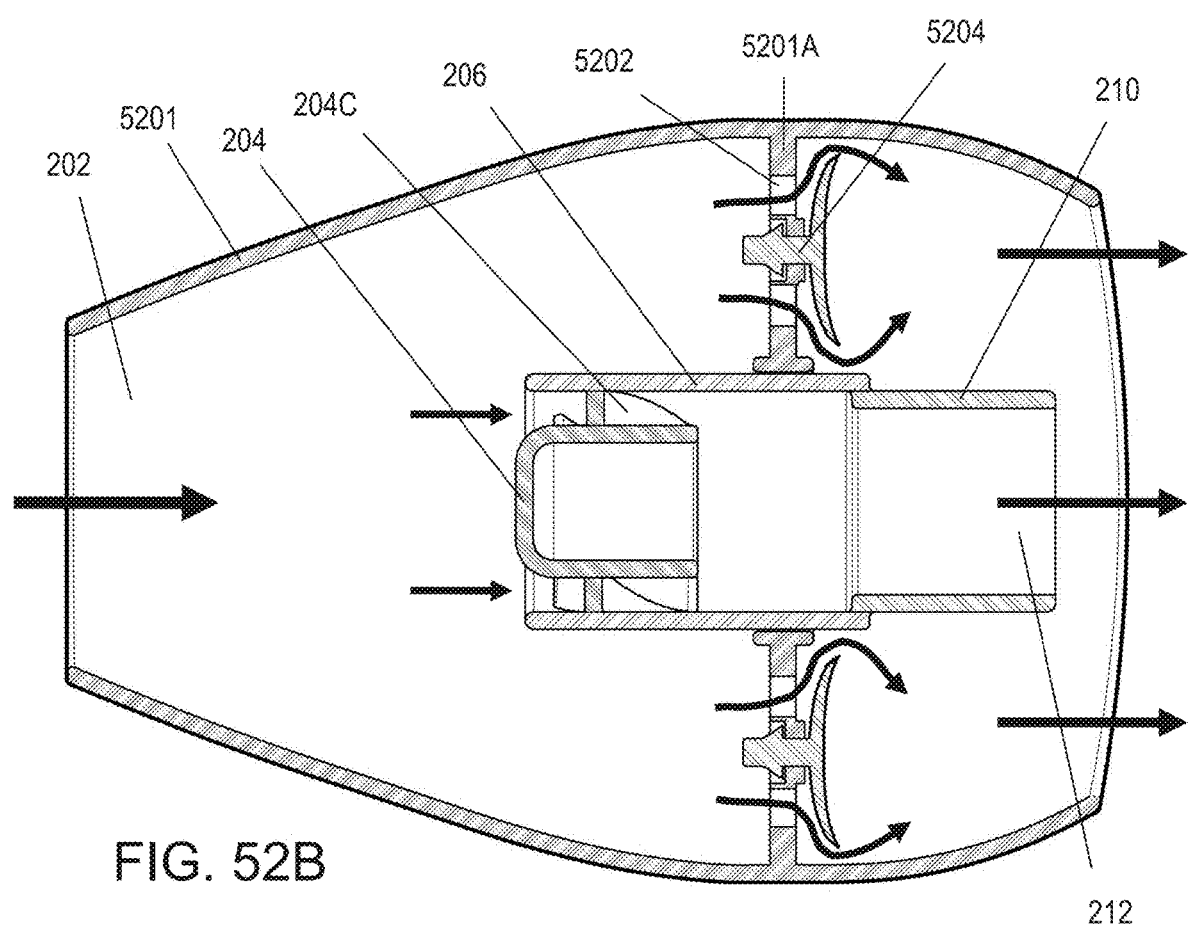
FIG. 52B shows a sectional top view of the whistle illustrated in FIG. 50, in accordance with one or more embodiments.

Before a user's exhalation enters inlet 202, umbrella valve flex obstructors 5204 may be in their closed position, and so may prevent airflow through vent holes 5202. As a user begins to exhale (see FIG. 52A), expiratory airflow may enter the whistle through inlet 202, and be guided into a swirling vortex within main tube 206 by airflow guide 204. The vortex may exit outlet tube 210, and thus produce an acoustic emission or the whistle's characteristic sound. As a user continues to exhale, and airflow may increase through inlet 202, an increasing amount of airflow resistance may develop along the airflow path leading from inlet 202 through outlet tube 210; this increasing amount of airflow resistance may result in an increase in back-pressure at the entrance of main tube 206. This increase in back-pressure at the entrance of main tube 206 may, in turn, result in increasing outward pressure on the umbrella valve flex obstructors 5204, via vent holes 5202. If the user exhales forcefully enough, the outward pressure on the umbrella valve flex obstructors 5204 through vent holes 5202 may cause the obstructors 5204 to flex outward as illustrated in FIG. 52B, which may allow or increase airflow through vent holes 5202. The more pressure on obstructors 5204, the more airflow exits through vent holes 5202. In this way, the whistle's flow controller (i.e. 5201A, 5204, 5202) may dynamically allocate proportions of a user's expiratory airflow into the whistle between outlet tube 206 on the one hand, and vent holes 5202 on the other, and may thereby: a) limit back-pressure exerted on a user's respiratory system during measurement, b) extend the effective measurement range of the whistle, and c) improve the audibility/detectability of acoustic emissions at low flow rates while decreasing the probability of uncomfortable or painful acoustic intensities and/or frequencies at high flow rates. Note that, while FIGS. 50-52B illustrate a whistle a "straight through" design, the whistle could alternately or additionally comprise a "perpendicular" design (e.g. incorporating structural elements analogous to those illustrated within FIGS. 13, 18, 40, etc.), while still having one exit leading from the interior of the whistle housing out into the outside world, which may be advantageous in reducing errors, due to fingers covering over outlet(s), etc.

Figure 53:
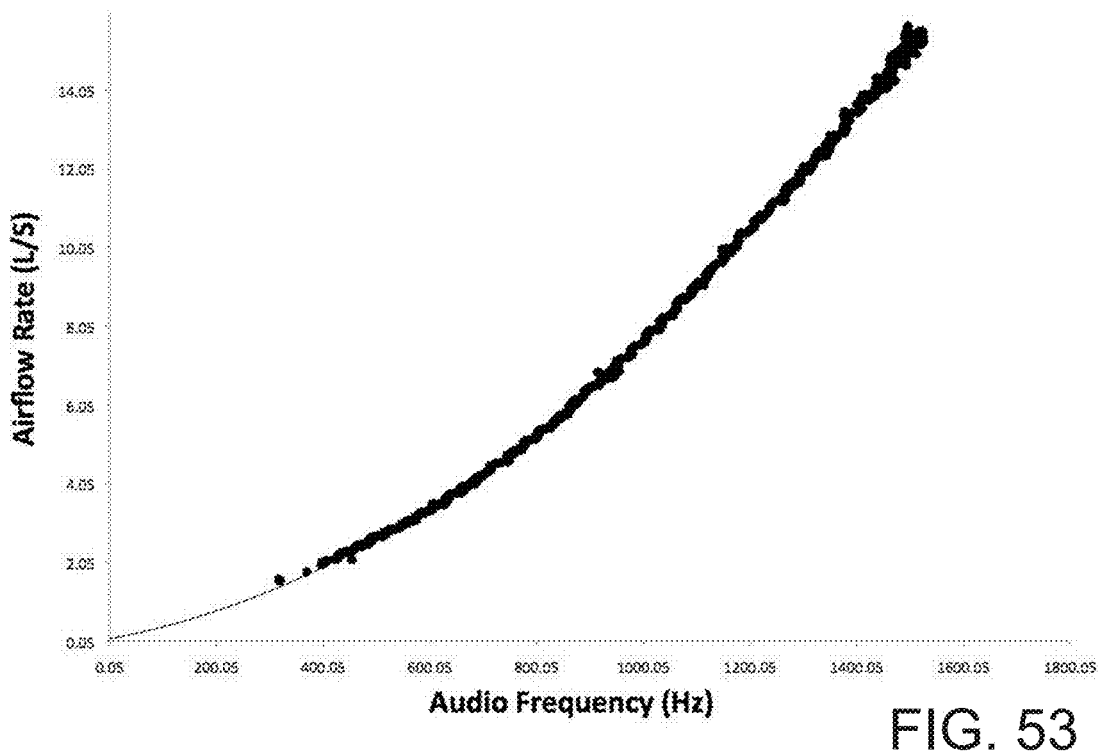
FIG. 53 shows an experimentally derived plot of the characteristic relationship between input airflow rate and output acoustic frequency for a prototype whistle similar to the whistle illustrated in FIGS. 50-52B, in accordance with one or more embodiments.
Figure 54:
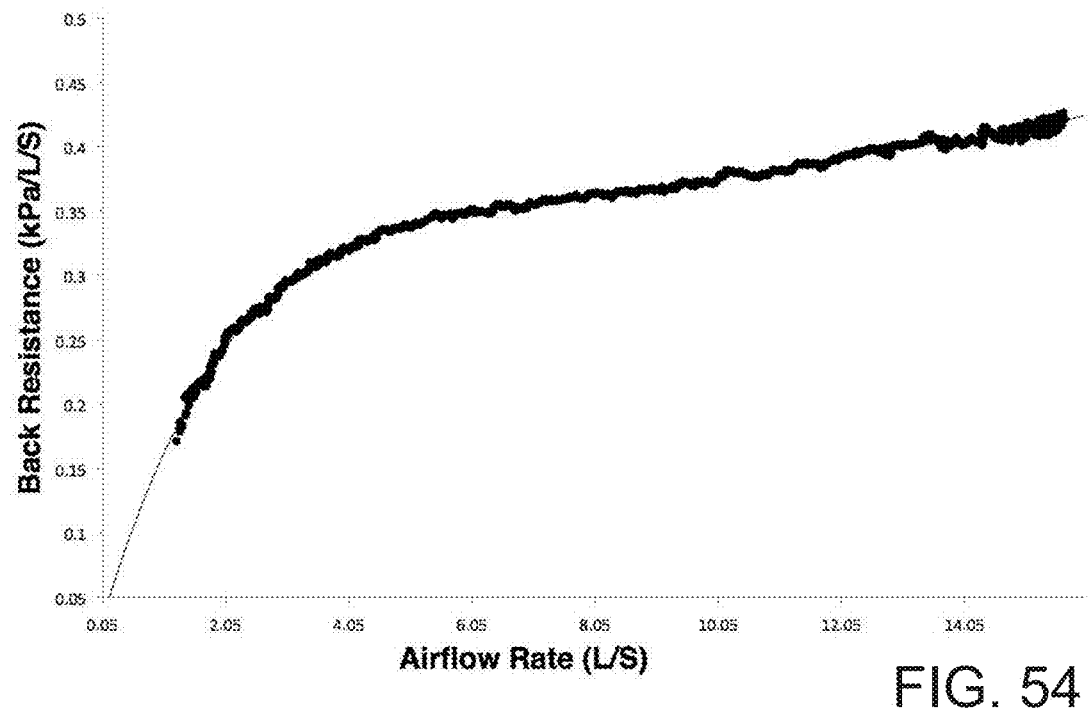
FIG. 54 shows an experimentally derived plot of back pressure, as a function of input airflow rate, for a prototype whistle similar to the whistle illustrated in FIGS. 50-52B, in accordance with one or more embodiments.

FIGS. 53-54 depict experimental results obtained from a whistle similar to the whistle illustrated by FIGS. 50-52B. FIG. 53 illustrates a relationship between an airflow rate provided to the whistle and an acoustic frequency generated by the whistle for the various airflow rates.

As illustrated in FIG. 53, the whistle may be designed or configured such that the resulting relationship between an airflow rate provided to the whistle and a frequency of the acoustic signal emitted by the whistle is non-linear. This non-linear relationship may allow for a wider effective measurement range with a standard microphone and or mobile device than may be possible if the relationship is linear or substantially linear. In addition, a whistle configured to create this non-linear relationship between airflow rate and frequency may result in a reduction of back-pressure created within the whistle at high airflow rates.

At low airflow rates In FIG. 53, small changes in airflow rate result in relatively large changes in frequency; this helps to ensure that, at low airflow rates, small changes in airflow rate may be measureable (i.e. as large, identifiable changes in frequency). In FIG. 53 at high airflow rates, large changes in airflow rate result in relatively small changes in frequency. This helps to ensure that, at high airflow rates, a frequency emitted by the whistle does not rise past a point where it can no longer be reliably received and or processed by a mobile device and or microphone (due to, for instance, limitations related to analog or digital bandwidth, sampling frequency, sample frame length, processing rate, etc.). In such ways, the non-linearities of the relationship illustrated in FIG. 53 serve to broaden the "sweet spot" of the system's effective measurement range.

A whistle without a flow controller may result in a substantially linear relationship between the airflow rate and the frequency of the acoustic signal emitted from the whistle. Therefore, any detection of frequency emissions outside of the measurement "sweet spot" may result in inaccurate spirometric results. While a whistle having a substantially linear relationship between airflow rate and frequency may have advantages such as ease of manufacture and calibration, cost of manufacturing, etc., the range in which accurate measurements may be determined may be reduced and the spirometric measurements may be more influenced by back-pressure because the generated back-pressure may be higher in whistles that have linear or substantially linear relationships between the airflow rate and the frequency of the acoustic signal.

Alternatively, a whistle including a flow controller such as the whistle illustrated in FIGS. 50-52B, may modify the relationship between the airflow rate and the frequency such that the change in frequency per unit change in flow rate is higher at low airflow rates and lower at high flow rates, as illustrated in FIG. 53. By modifying the relationship between airflow rate and frequency, it results in a wider effective measurement range with a standard microphone than if the relationship was linear. Specifically, by implementing a whistle having the non-linear relationship between airflow rate and frequency emission with a standard microphone allows for effectively magnifying the differences in the relationship between airflow and frequency at low airflow rates and effectively compressing the differences in the relationship between airflow and frequency at high airflow rates, such that frequencies beyond a mobile device's software or hardware processing capabilities may not fall within a desired measurement range.

As illustrated in FIG. 53, changes in acoustic frequency per unit change in airflow rate at smaller airflow rate values may produce greater changes in frequency values than at larger airflow rate values. For example, when an airflow having a first rate of approximately 2.05 L/S is provided, an acoustic emission having an audio frequency of approximately 400.05 Hz is generated. When an airflow having a second rate of approximately 4.05 L/S is provided, an acoustic emission having an audio frequency of approximately 675.05 Hz is generated. When an airflow having a third rate of approximately 12.05 L/S is provided, an acoustic emission having an audio frequency of approximately 1275.05 Hz is generated and when an airflow having a fourth rate of approximately 14.05 L/S is provided, an acoustic emission having an audio frequency of approximately 1450.05 Hz. Thus, the rate of change in frequency of acoustic emissions between the smaller airflow rates of the first airflow rate and the second airflow rate (e.g., 675.05−400.05=275 Hz) is greater than the rate of change in frequency of acoustic emissions between the larger airflow rates of the third airflow rate and the fourth airflow rate (e.g., 1450.05−1275.05=125 Hz).

Likewise, a change in slope between different audio frequency values may vary with the airflow rate. For example, the slope between two audio frequencies of acoustic emissions detected in the lower end of the frequency range may have a smaller slope than the slope between two audio frequencies of the acoustic emissions detected in the higher end of the frequency range. In some embodiments, the slope between two detected audio frequencies may be used to determine an airflow rate.

FIG. 54 illustrates a flow controller's reductive effect on back pressure. As illustrated in FIG. 54, the plotted curve has a declining slope as airflow rate increases. For example, referring to FIGS. 52A, 52B, when a greater proportion of expiratory airflow from a user is routed through vent holes 5202, the back resistance decreases even though the airflow rate continues to increase.

Figure 55:
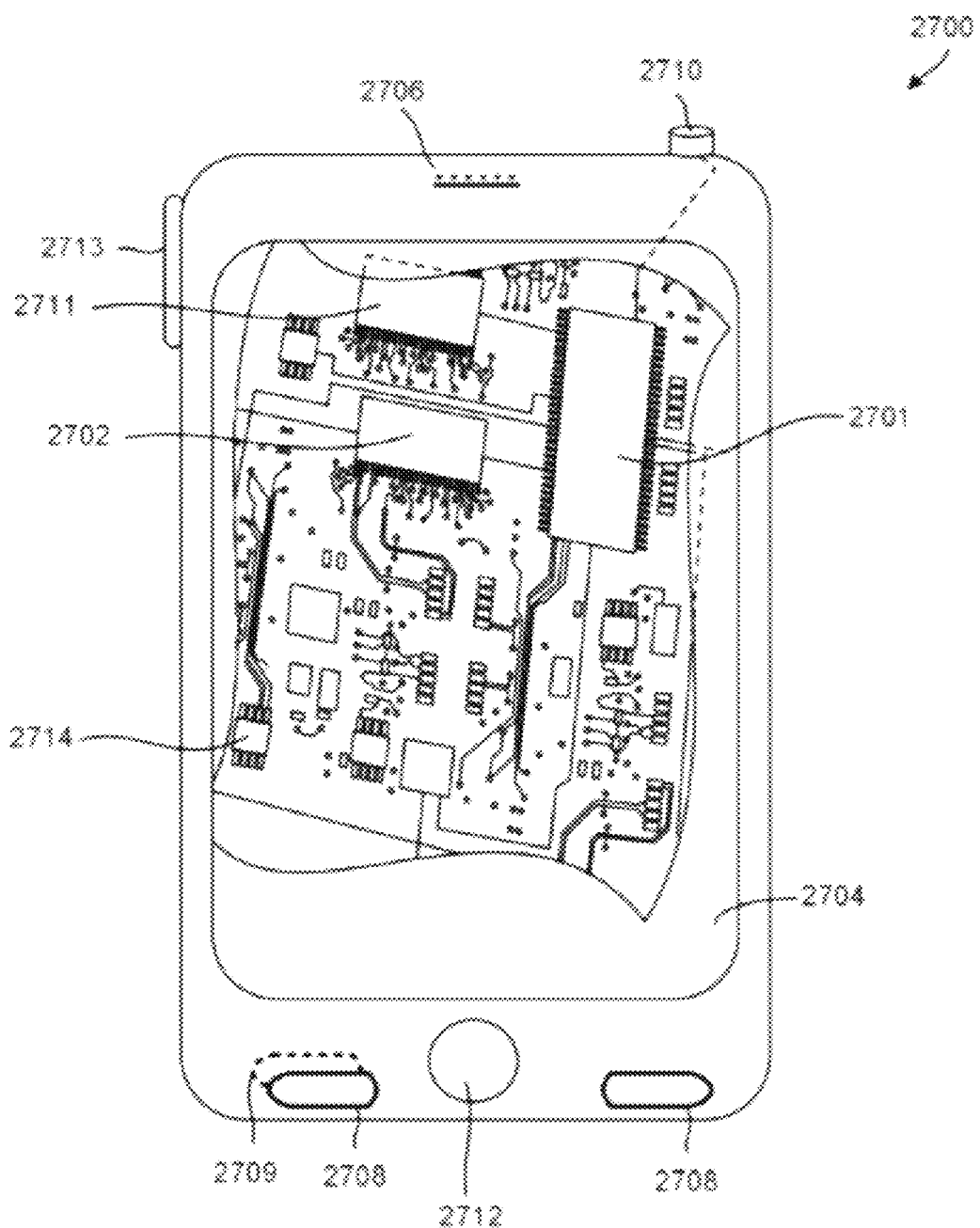
FIG. 55 is a component block diagram illustrating a hand-held mobile electronic device that is suitable for use in accordance with the various embodiments.

Moving on to a discussion on the mobile device, various embodiments may be implemented on or comprise a variety of hand-held mobile electronic devices, an example of which is illustrated in FIG. 55. In the example illustrated in FIG. 55, the hand-held mobile electronic device 2700 includes a processor 2701 coupled to internal memory 2702, a display 2704, a speaker 2706, one or more front-side microphones 2708 and/or microphone arrays for capturing directional sounds, and one or more back-side microphones 2709 and/or microphone arrays for capturing directional sounds present behind the hand-held mobile electronic device 2700.

Additionally, the hand-held mobile electronic device 2700 may include an antenna 2710 for sending and receiving electromagnetic radiation, which may be connected to a wireless data link and/or cellular telephone transceiver 2711 coupled to the processor 2701. The hand-held mobile electronic device 2700 may also include menu selection buttons 2712, rocker switches 2713 or other similar user interface elements for receiving user inputs or for initiating the process of sampling sounds. The user interface elements may be implemented as hard key buttons, soft key buttons, as a touch keys, a resistive or capacitive (e.g. "multitouch") touchpad, or any other way of receiving user input for initiating the sampling of sounds, digitizing the sampled sounds, storing of the digitized sounds in a memory, etc.

The hand-held mobile electronic device 2700 may also include a sound encoding/decoding (CODEC) circuit 2714, which digitizes sound received from a microphone 2708 into data packets suitable for wireless transmission and decodes received sound data packets to generate analog signals that are provided to the speaker 2706 to generate sound. Also, one or more of the processor 2701, wireless transceiver 2711 and CODEC 2714 may include a digital signal processor (DSP) circuit (not shown separately).

Figure 56:
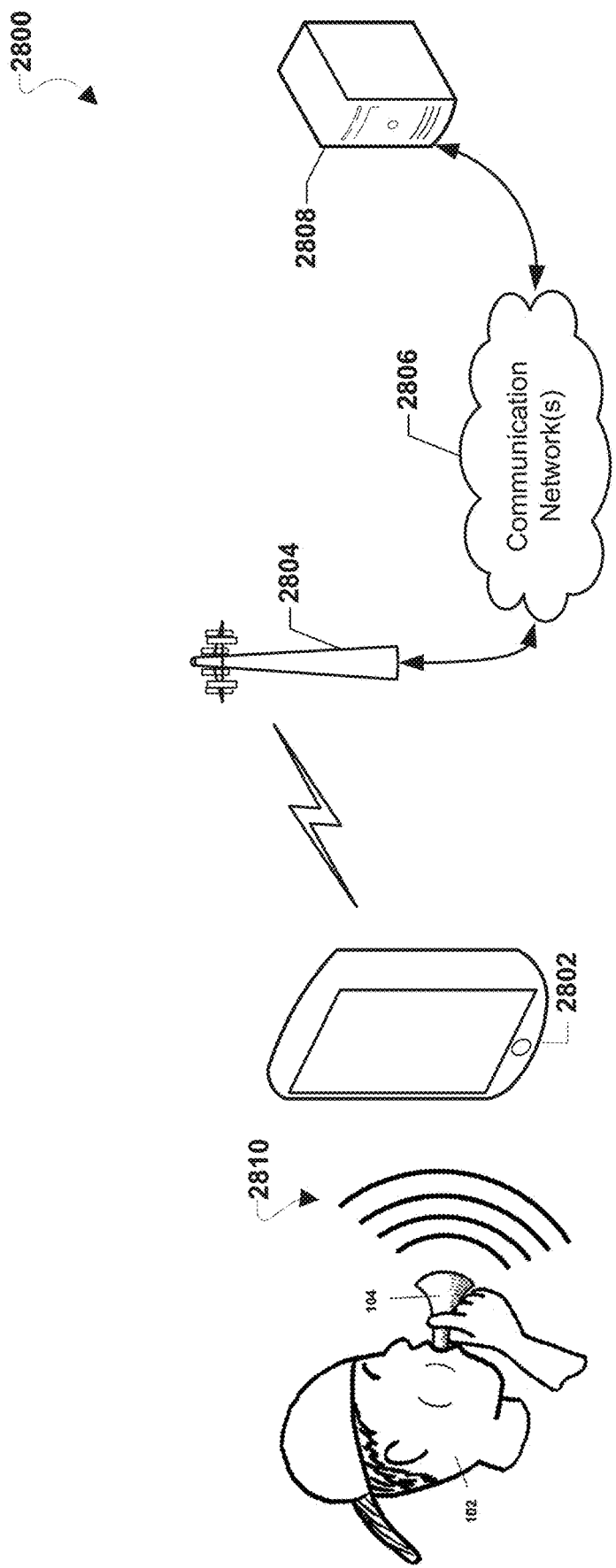
FIG. 56 is a component block diagram of a communication system suitable for use with various embodiments.

Various embodiments may be implemented within a variety of communication systems, an example of which is illustrated in FIG. 56. The communication system 2800, may include a mobile electronic device 2802 (e.g., mobile electronic device 108), a base station 2804, one or more communication network(s) 2806, and a server 2808.

The base station 2804 may provide a wireless communication link to the mobile electronic device 2802 to facilitate communication of wireless signals between the base station 2804 and the mobile electronic device 2802. The base station 2804 may include one or more wired and/or wireless communications connections to the one or more communication networks 2806. While the base station 2804 is illustrated in FIG. 56 as being a tower, base station 2804 may be any network access node including a communication satellite, etc. The one or more communication networks 2806 may provide access to other remote base stations over the same or another wired and/or wireless communications connection. In addition, the one or more communication networks 2806 may provide access to a remote server 2808. The mobile electronic device 2802 may be configured to communicate with the remote server 2808 for exchanging various types of communications and data, including information associated with acoustic emissions 2810 generated when a user 102 provides an airflow to a whistle 104, spirometric measurement information, etc.

The mobile electronic device 2802 may include one or more communication interfaces configured to allow the mobile electronic device 2802 to wirelessly communication with the one or more communication networks 2806 via the base station 2804. For example, the one or more communication interfaces of the mobile electronic device 2802 may implement a relatively short-range wireless communication protocol such as Wi-Fi, ZigBee, Bluetooth, or IEEE 802.11, or a long-rage wireless communication protocol such as a cellular protocol including 3GPP Long Term Evolution (LTE), Global System for Mobility (GSM), Code Division Multiple Access (CDMA), Wideband Code Division Multiple Access (WCDMA), Worldwide Interoperability for Microwave Access (WiMAX), Time Division Multiple Access (TDMA), and other mobile telephony communication technologies. Alternatively, the mobile electronic device 2802 may include one or more ports configured to allow the mobile electronic device 2802 to connect with the one or more communication networks 2806 and/or another electronic device via a wired cable or plug.

The server 2808 may be configured to process and/or store information associated with the acoustic emissions 2810 generated by the whistle 104, spirometric measurement information, etc. In some embodiments, the mobile electronic device 2802 may detect the acoustic emissions 2810 and determine spirometric measurements using information associated with the acoustic emissions 2810. Alternatively, one or more of the operations associated with spirometric measurements may be performed by the server 2808. For example, the mobile electronic device 2802 may detect the acoustic emissions 2810 and then transmit the information associated with the acoustic emissions 2810 to the server 2808 via the one or more communication network(s) 2806. In some embodiments, the mobile electronic device 2802 may perform one or more preprocessing operations on the acoustic emissions 2810 prior to transmitting the data to the server 2808. Alternatively, the mobile electronic device 2802 may transmit raw acoustic emissions 2810 to the server 2808 such that the server 2808 performs all of the data processing and spirometric measurements. In addition, the server 2808 may be configured to store the spirometric measurement information such that other electronic devices may communicate with the server 2808 to access the information.

The foregoing method descriptions and the process flow diagrams are provided merely as illustrative examples and are not intended to require or imply that the blocks of the various embodiments must be performed in the order presented. As will be appreciated by one of skill in the art the order of blocks in the foregoing embodiments may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an" or "the" is not to be construed as limiting the element to the singular.

The foregoing whistle device descriptions and diagrams are similarly provided merely as illustrative examples. It should be understood that, in the various embodiments, certain physical parts described herein may be combined (for instance, fabricating two functional or logical parts as one physical part) or separated (for instance, by molding one functional or logical part as two physical parts). As such, nothing in the specification should be used to limit the claims to a specific arrangement of physical parts unless expressly recited as such in the claims.

The various illustrative logical blocks, modules, circuits, and algorithm blocks described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The foregoing descriptions described in connection with the embodiments disclosed herein reference the terms "frequency" and "period". It should be known by one skilled in the art that frequency and period have a well-defined relationship; a frequency can be specified given a period, and vice-versa. As such, nothing in the specification should be used to limit the claims to a specific usage of the term "frequency" or "period", unless expressly recited in the claims.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein.

The invention claimed is:

1. An acoustic device for spirometric measurement, comprising:
   an inlet conduit configured to receive an airflow;
   a walled cavity in communication with the inlet conduit, wherein an inner surface of the walled cavity is configured to guide at least a portion of the airflow;
   an outlet configured to receive at least a portion of the airflow and transduce at least a portion of kinetic energy of the received airflow into an acoustic emission including one or more frequency values within a range of frequency values, wherein the one or more frequency values included in the acoustic emission vary with a rate at which the airflow is provided to the inlet conduit; and
   a flow controller configured to modify at least a portion of the airflow provided to the inlet conduit such that a rate of change in the one or more frequency values included in the acoustic emission varies inversely with a rate of the airflow provided to the inlet conduit.

2. The acoustic device of claim 1, wherein the flow controller includes at least one or more of a valve, a vent, an obstructor, a force exerting element, a rotational constraint, a sliding constraint, a flexing constraint, or a joint.

3. The acoustic device of claim 2, wherein the flow controller includes at least one or more of a pressure relief valve, a spillover valve, an umbrella valve, a duckbill valve, an elastomeric valve, a fluidic valve, a valve including no moving parts, an opening leading to an exterior of the acoustic device, a passageway leading to the exterior of the acoustic device, a flexible obstructor, a spring, a pivot, a hinge, a linear sliding constraint, a plug, a magnet, or a compressible gas reservoir.

4. The acoustic device of claim 1, wherein the flow controller is a mechanical flow controller.

5. The acoustic device of claim 1, wherein the flow controller comprises a fluidic flow controller.

6. The acoustic device of claim 1, wherein the flow controller is configured to modify at least a portion of the airflow provided to the inlet conduit via a static structure in conjunction with fluidic interactions.

7. The acoustic device of claim 1, wherein the flow controller is a manually configurable flow controller.

8. The acoustic device of claim 1, further comprising at least one or more of a visual indicator, a human readable identifier, or a machine readable identifier corresponding to at least one characteristic or parameter of the acoustic device.

9. The acoustic device of claim 1, wherein the range of frequency values includes at least one of an ultrasonic frequency and an audible frequency.

10. The acoustic device of claim 1, further comprising:
a second outlet in fluid communication with the walled cavity,
wherein the second outlet is configured to emit a second acoustic emission having one or more frequency values within the range of frequency values based on the rate at which the airflow is provided to the inlet conduit.

11. The acoustic device of claim 1, further comprising an inhaler dispenser.

12. The acoustic device of claim 11, further comprising a dosage counter.

13. An acoustic device for spirometric measurement, comprising:
an inlet conduit configured to receive an airflow;
a walled cavity in fluid communication with the inlet conduit, wherein an inner surface of the walled cavity is configured to guide at least a portion of the airflow;
an acoustic outlet configured to receive at least a portion of the airflow and transduce at least a portion of kinetic energy of the received airflow into an acoustic emission including a frequency, wherein the frequency of the acoustic emission varies in response to a rate at which the airflow is provided to the inlet conduit;
a flow controller in fluid communication with at least one of the inlet conduit, the walled cavity, and the acoustic outlet, the flow controller including a pressure relief valve; and
a vent outlet,
wherein the flow controller is configured to modify the airflow provided to the inlet conduit such that at least a portion of the airflow provided to the inlet conduit is directed to at least one of a first route that passes through the acoustic outlet and a second route that passes through the vent outlet; and
wherein the flow controller is configured to modify at least a portion of the airflow provided to the inlet conduit such that a rate of change in the one or more frequency values included in the acoustic emission varies inversely with a rate of the airflow provided to the inlet conduit.

14. The acoustic device of claim 13, wherein at least one or more of the inlet conduit, the walled cavity, or the acoustic outlet includes the flow controller.

15. The acoustic device of claim 13, wherein at least a portion of the flow controller contacts one or more surfaces spaced apart from the inlet conduit, the walled cavity, and the acoustic outlet.

16. The acoustic device of claim 13, wherein the flow controller includes at least one or more of a spillover valve, an umbrella valve, a duckbill valve, a spring-actuated valve, an elastomeric valve, a fluidic valve, or a valve including no moving parts.

17. The acoustic device of claim 13, further comprising at least one or more of:
an inhaler dispenser; or
a dosage counter.

* * * * *